US012201833B2

(12) United States Patent
Edgerton et al.

(10) Patent No.: US 12,201,833 B2
(45) Date of Patent: Jan. 21, 2025

(54) TRANSCUTANEOUS NEUROMODULATION SYSTEM AND METHODS OF USING SAME

(71) Applicant: The Regents of The University of California, Oakland, CA (US)

(72) Inventors: Victor Reggie Edgerton, Los Angeles, CA (US); Yury P. Gerasimenko, Los Angeles, SD (US); Parag Gad, Woodland Hills, CA (US); Nicholas A. Terrafranca, Laguna Nigel, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/142,318

(22) Filed: May 2, 2023

(65) Prior Publication Data

US 2024/0001116 A1  Jan. 4, 2024

Related U.S. Application Data

(63) Continuation of application No. 17/140,896, filed on Jan. 4, 2021, now Pat. No. 11,638,820, which is a
(Continued)

(51) Int. Cl.
*A61N 1/36* (2006.01)
*A61N 1/04* (2006.01)
*A61N 1/06* (2006.01)

(52) U.S. Cl.
CPC ....... *A61N 1/36003* (2013.01); *A61N 1/0456* (2013.01); *A61N 1/06* (2013.01);
(Continued)

(58) Field of Classification Search
None
See application file for complete search history.

(56) References Cited

U.S. PATENT DOCUMENTS 3,543,761 A  12/1970  Bradley
3,662,758 A   5/1972  Glover
(Continued)

FOREIGN PATENT DOCUMENTS

JP  2002-200178      7/2002
JP  2008-067917 A    3/2008
(Continued)

OTHER PUBLICATIONS

Office Action for Canadian Patent Application No. 2,824,782 issued on Nov. 29, 2017.
(Continued)

*Primary Examiner* — Ankit D Tejani
(74) *Attorney, Agent, or Firm* — K&L Gates LLP

(57) ABSTRACT

A neuromodulation system, device, and method are disclosed. In an embodiment, a neuromodulation system includes a processor, a signal generator, a first electrode, and a second electrode. The processor in cooperation with the signal generator, the first electrode, and the second electrode are configured to deliver a transcutaneous stimulation to a mammal. The transcutaneous stimulation is configured by the processor for inducing voluntary movement in the mammal. The first electrode is positioned transcutaneously on a spinal cord and/or spinal cord dorsal roots of the mammal. Additionally, the second electrode is placed transcutaneously on or over at least one of the spinal cord and/or the spinal cord dorsal roots, a muscle, a nerve, or on or near a target end organ or bodily structure of the mammal. The second electrode is in communication with the first electrode through a hardwire or wireless connection.

20 Claims, 37 Drawing Sheets

Related U.S. Application Data continuation of application No. 16/153,472, filed on Oct. 5, 2018, now Pat. No. 10,881,853, which is a continuation of application No. 14/925,791, filed on Oct. 28, 2015, now Pat. No. 10,092,750, which is a continuation-in-part of application No. 14/357,481, filed as application No. PCT/US2012/064874 on Nov. 13, 2012, now Pat. No. 9,393,409.

(60) Provisional application No. 62/069,590, filed on Oct. 28, 2014, provisional application No. 61/559,025, filed on Nov. 11, 2011.

(52) U.S. Cl.
CPC ........ *A61N 1/36025* (2013.01); *A61N 1/3616* (2013.01); *A61N 1/36171* (2013.01)

(56) References Cited

U.S. PATENT DOCUMENTS

| | | |
|---|---|---|
| 3,724,467 A | 4/1973 | Avery et al. |
| 4,044,774 A | 8/1977 | Corbin et al. |
| 4,102,344 A | 6/1978 | Conway et al. |
| 4,141,365 A | 2/1979 | Fischell et al. |
| 4,285,347 A | 8/1981 | Hess |
| 4,340,063 A | 7/1982 | Maurer |
| 4,379,462 A | 4/1983 | Borkan et al. |
| 4,414,986 A | 11/1983 | Dickhudt et al. |
| 4,538,624 A | 9/1985 | Tarjan |
| 4,549,556 A | 10/1985 | Tajan et al. |
| 4,800,898 A | 1/1989 | Hess et al. |
| 4,934,368 A | 6/1990 | Lynch |
| 5,002,053 A | 3/1991 | Garcia-Rill et al. |
| 5,031,618 A | 7/1991 | Mullett |
| 5,081,989 A | 1/1992 | Graupe |
| 5,121,754 A | 6/1992 | Mullett |
| 5,344,439 A | 9/1994 | Otten |
| 5,354,320 A | 10/1994 | Schaldach |
| 5,374,285 A | 12/1994 | Vaiani et al. |
| 5,417,719 A | 5/1995 | Hull et al. |
| 5,562,718 A | 10/1996 | Palermo |
| 5,643,330 A | 7/1997 | Holsheimer et al. |
| 5,733,322 A | 3/1998 | Starkebaum |
| 5,983,141 A | 11/1999 | Sluijter et al. |
| 6,066,163 A | 5/2000 | John |
| 6,104,957 A | 8/2000 | Alo et al. |
| 6,122,548 A | 9/2000 | Starkebaum et al. |
| 6,308,103 B1 | 10/2001 | Gielen |
| 6,319,241 B1 | 11/2001 | King et al. |
| 6,470,213 B1 | 10/2002 | Alley |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,819,956 B2 | 11/2004 | DiLorenzo |
| 6,839,594 B2 | 1/2005 | Cohen |
| 6,871,099 B1 | 3/2005 | Whitehurst et al. |
| 6,892,098 B2 | 5/2005 | Ayal |
| 6,895,280 B2 | 5/2005 | Meadows |
| 6,895,283 B2 | 5/2005 | Erickson et al. |
| 6,937,891 B2 | 8/2005 | Leinders |
| 6,950,706 B2 | 9/2005 | Rodriguez |
| 6,975,907 B2 | 12/2005 | Zanakis |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,110,820 B2 | 9/2006 | Tcheng |
| 7,127,287 B2 | 10/2006 | Duncan |
| 7,127,296 B2 | 10/2006 | Bradley |
| 7,127,297 B2 | 10/2006 | Law et al. |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Campen |
| 7,239,920 B1 | 7/2007 | Thacker et al. |
| 7,251,529 B2 | 7/2007 | Greenwood-Van |
| 7,252,090 B2 | 8/2007 | Goetz |
| 7,313,440 B2 | 12/2007 | Miesel et al. |
| 7,330,760 B2 | 2/2008 | Heruth et al. |
| 7,337,005 B2 | 2/2008 | Kim |
| 7,377,006 B2 | 2/2008 | Kim |
| 7,415,309 B2 | 8/2008 | McIntyre |
| 7,463,928 B2 | 12/2008 | Lee |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt |
| 7,584,000 B2 | 9/2009 | Erickson |
| 7,590,454 B2 | 9/2009 | Garabedian et al. |
| 7,603,178 B2 | 10/2009 | North et al. |
| 7,628,750 B2 | 12/2009 | Cohen |
| 7,660,636 B2 | 2/2010 | Castel et al. |
| 7,697,995 B2 | 4/2010 | Cross et al. |
| 7,729,781 B2 | 6/2010 | Swoyer et al. |
| 7,734,340 B2 | 6/2010 | De Ridder |
| 7,734,351 B2 | 6/2010 | Testerman |
| 7,769,463 B2 | 8/2010 | Katsnelson |
| 7,797,057 B2 | 9/2010 | Harris |
| 7,801,601 B2 | 9/2010 | Maschino et al. |
| 7,813,803 B2 | 10/2010 | Heruth et al. |
| 7,890,182 B2 | 2/2011 | Parramon et al. |
| 7,949,395 B2 | 5/2011 | Kuzma |
| 7,949,403 B2 | 5/2011 | Palermo |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,108,052 B2 | 1/2012 | Boling |
| 8,131,358 B2 | 3/2012 | Moffitt |
| 8,155,750 B2 | 4/2012 | Jaax |
| 8,170,660 B2 | 5/2012 | Dacey |
| 8,190,262 B2 | 5/2012 | Gerber |
| 8,195,304 B2 | 6/2012 | Strother et al. |
| 8,239,038 B2 | 8/2012 | Wolf |
| 8,260,436 B2 | 9/2012 | Gerber et al. |
| 8,311,644 B2 | 11/2012 | Moffitt |
| 8,332,029 B2 | 12/2012 | Glukhovsky et al. |
| 8,346,366 B2 | 1/2013 | Arle |
| 8,352,036 B2 | 1/2013 | Dimarco |
| 8,355,791 B2 | 1/2013 | Moffitt |
| 8,355,797 B2 | 1/2013 | Caparso et al. |
| 8,364,273 B2 | 1/2013 | De Ridder |
| 8,369,961 B2 | 2/2013 | Christman |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishmamur |
| 8,805,542 B2 | 8/2014 | Tai |
| 10,881,853 B2 | 1/2021 | Edgerton |
| 2002/0055779 A1 | 5/2002 | Andrews |
| 2002/0111661 A1 | 8/2002 | Cross et al. |
| 2002/0188332 A1* | 12/2002 | Lurie .............. A61N 1/39044 607/48 |
| 2003/0032992 A1 | 2/2003 | Thacker |
| 2003/0078633 A1 | 4/2003 | Firlik et al. |
| 2004/0044380 A1 | 3/2004 | Buringa |
| 2004/0122483 A1 | 6/2004 | Nathan et al. |
| 2004/0133248 A1 | 7/2004 | Frei et al. |
| 2004/0138518 A1 | 7/2004 | Rise et al. |
| 2004/0172097 A1 | 9/2004 | Brodard et al. |
| 2004/0181263 A1 | 9/2004 | Blazer et al. |
| 2005/0004622 A1 | 1/2005 | Cullen et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0231186 A1 | 10/2005 | Barrera et al. |
| 2005/0246004 A1 | 11/2005 | Cameron et al. |
| 2006/0041295 A1 | 2/2006 | Osypka |

(56) References Cited

U.S. PATENT DOCUMENTS

| | | |
|---|---|---|
| 2006/0089696 A1 | 4/2006 | Olsen et al. |
| 2006/0100671 A1 | 5/2006 | Ridder |
| 2006/0122678 A1 | 6/2006 | Olsen et al. |
| 2006/0142822 A1 | 6/2006 | Tulgar |
| 2006/0149337 A1 | 7/2006 | John |
| 2006/0195153 A1 | 8/2006 | DiUbaldi et al. |
| 2006/0239482 A1 | 10/2006 | Hatoum |
| 2006/0241356 A1 | 10/2006 | Flaherty |
| 2007/0016097 A1 | 1/2007 | Farquhar et al. |
| 2007/0049814 A1 | 3/2007 | Muccio |
| 2007/0060954 A1 | 3/2007 | Cameron et al. |
| 2007/0060980 A1 | 3/2007 | Strother et al. |
| 2007/0083240 A1 | 4/2007 | Peterson et al. |
| 2007/0156179 A1 | 7/2007 | S.E. |
| 2007/0179534 A1 | 8/2007 | Firlik et al. |
| 2007/0191709 A1 | 8/2007 | Swanson |
| 2007/0233204 A1 | 10/2007 | Lima et al. |
| 2007/0265691 A1 | 11/2007 | Swanson |
| 2008/0009927 A1 | 1/2008 | Vilimis |
| 2008/0046049 A1 | 2/2008 | Skubitz et al. |
| 2008/0051851 A1 | 2/2008 | Lin |
| 2008/0103579 A1 | 5/2008 | Gerber |
| 2008/0140152 A1 | 6/2008 | Imran et al. |
| 2008/0140169 A1 | 6/2008 | Imran |
| 2008/0183224 A1 | 7/2008 | Barolat |
| 2008/0208287 A1 | 8/2008 | Palermo |
| 2008/0221653 A1 | 9/2008 | Agrawal |
| 2008/0228250 A1 | 9/2008 | Mironer |
| 2008/0234791 A1 | 9/2008 | Arle et al. |
| 2008/0294226 A1 | 11/2008 | Moffitt et al. |
| 2009/0112281 A1 | 4/2009 | Miyazawa et al. |
| 2009/0204173 A1 | 8/2009 | Fang et al. |
| 2009/0270960 A1 | 10/2009 | Zhao et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Haggers |
| 2010/0004715 A1 | 1/2010 | Fahey |
| 2010/0023103 A1 | 1/2010 | Elborno |
| 2010/0125313 A1 | 5/2010 | Lee et al. |
| 2010/0137938 A1 | 6/2010 | Kishawi et al. |
| 2010/0152811 A1 | 6/2010 | Flaherty |
| 2010/0185253 A1 | 7/2010 | Dimarco et al. |
| 2010/0217355 A1 | 8/2010 | Tass et al. |
| 2010/0241191 A1 | 9/2010 | Testerman |
| 2010/0274312 A1 | 10/2010 | Alataris |
| 2010/0312304 A1 | 12/2010 | York et al. |
| 2011/0034977 A1 | 2/2011 | Janik et al. |
| 2011/0054567 A1 | 3/2011 | Lane |
| 2011/0054568 A1 | 3/2011 | Lane |
| 2011/0077660 A1 | 3/2011 | Janik et al. |
| 2011/0130804 A1 | 6/2011 | Lin et al. |
| 2011/0160810 A1 | 6/2011 | Griffith |
| 2011/0184489 A1 | 7/2011 | Nicolelis et al. |
| 2011/0218590 A1 | 9/2011 | Degiorgio et al. |
| 2011/0218594 A1 | 9/2011 | Doron |
| 2011/0224665 A1 | 9/2011 | Crosby et al. |
| 2011/0224753 A1 | 9/2011 | Palermo |
| 2011/0224757 A1 | 9/2011 | Zdeblick et al. |
| 2011/0237921 A1 | 9/2011 | Askin et al. |
| 2012/0035684 A1 | 2/2012 | Thompson et al. |
| 2012/0059432 A1 | 3/2012 | Emborg et al. |
| 2012/0071950 A1 | 3/2012 | Archer |
| 2012/0109251 A1 | 5/2012 | Lebedev |
| 2012/0123293 A1 | 5/2012 | Shah et al. |
| 2012/0136408 A1 | 5/2012 | Grill et al. |
| 2012/0165899 A1 | 6/2012 | Gliner |
| 2012/0172946 A1 | 7/2012 | Altaris et al. |
| 2012/0179222 A1 | 7/2012 | Jaax |
| 2012/0232615 A1 | 9/2012 | Barolat |
| 2012/0277834 A1 | 11/2012 | Mercanzini et al. |
| 2012/0330391 A1 | 12/2012 | Bradley et al. |
| 2013/0030501 A1 | 1/2013 | Feler et al. |
| 2013/0035745 A1 | 2/2013 | Ahmed et al. |
| 2013/0085361 A1 | 4/2013 | Mercanzini et al. |
| 2013/0096640 A1 | 4/2013 | Possover |
| 2013/0123568 A1 | 5/2013 | Hamilton et al. |
| 2013/0253299 A1 | 9/2013 | Weber |
| 2013/0253611 A1 | 9/2013 | Lee |
| 2014/0031895 A1* | 1/2014 | Rahimi ............ A61N 1/36021 607/46 |
| 2014/0163640 A1 | 6/2014 | Edgerton et al. |
| 2014/0180361 A1 | 6/2014 | Burdick |
| 2014/0316484 A1 | 10/2014 | Edgerton |
| 2014/0316503 A1 | 10/2014 | Tai |
| 2015/0217120 A1 | 8/2015 | Nandra et al. |
| 2015/0231396 A1 | 8/2015 | Burdick et al. |
| 2016/0030748 A1 | 2/2016 | Edgerton et al. |
| 2016/0121109 A1 | 5/2016 | Edgerton et al. |
| 2016/0175586 A1 | 6/2016 | Edgerton et al. |
| 2016/0220813 A1 | 8/2016 | Edgergton et al. |
| 2016/0310739 A1 | 10/2016 | Burdick et al. |
| 2017/0157389 A1 | 6/2017 | Tai et al. |
| 2018/0353755 A1 | 12/2018 | Edgerton et al. |
| 2019/0374777 A1* | 12/2019 | Burdick ............ A61N 1/36071 |

FOREIGN PATENT DOCUMENTS

| | | |
|---|---|---|
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2001102533 | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |
| WO | 1997/047357 A1 | 12/1997 |
| WO | 2003/026735 A2 | 4/2003 |
| WO | 2003/092795 A1 | 11/2003 |
| WO | 2004/087116 A2 | 10/2004 |
| WO | 2005/051306 A2 | 6/2005 |
| WO | 2005/087307 A2 | 9/2005 |
| WO | 2007/081764 A2 | 7/2007 |
| WO | 2007/107831 A2 | 9/2007 |
| WO | 2008/070807 A3 | 6/2008 |
| WO | 2008/109862 A2 | 9/2008 |
| WO | 2008/121891 A1 | 10/2008 |
| WO | 2009/042217 A1 | 4/2009 |
| WO | 2009/111142 A2 | 9/2009 |
| WO | 2010/114998 A1 | 10/2010 |
| WO | 2010/124128 A1 | 10/2010 |
| WO | 2011/005607 A1 | 1/2011 |
| WO | 2012/094346 A2 | 7/2012 |
| WO | 2012/100260 A2 | 7/2012 |
| WO | 2012/129574 A2 | 9/2012 |
| WO | 2013/071307 A1 | 5/2013 |
| WO | 2013/071309 A1 | 5/2013 |
| WO | 2014/144785 A1 | 9/2014 |
| WO | 2015/106286 A1 | 7/2015 |

OTHER PUBLICATIONS

Office Action for Australian Patent Application No. 2017221868 issued on Jan. 23, 2018.
Office Action for Canadian Patent Application No. 2,825,550 issued on Jan. 24, 2018.
US Office Action for U.S. Appl. No. 15/096,014 mailed on Sep. 14, 2017.
US Office Action for U.S. Appl. No. 14/925,791 mailed on Jul. 20, 2017.
U.S. Appl. No. 16/189,655, filed Nov. 13, 2018.
Office Action for Chinese Patent Application No. 201610987062.5 mailed on Sep. 30, 2018 (original and translation enclosed).
US Office Action for U.S. Appl. No. 15/713,456 mailed on Oct. 24, 2018.

(56) References Cited

OTHER PUBLICATIONS

Japanese Office Action Appl. No. 2017-198155 mailed Aug. 1, 2019—2 pages.

* cited by examiner

C

Outcome Measures
Correlations

NL-PCA

Multimodal
EMG and Kinematic Patterns
(PC1, PC2 and PC3)

PC LOADING MATRIX

|  | PC1 | PC2 | PC3 |
|---|---|---|---|
| VL | 0.56 | -0.58 | -0.39 |
| HM | 0.56 | 0.06 | -0.38 |
| TA | 0.52 | -0.09 | 0.73 |
| Sol | 0.49 | -0.54 | 0.37 |
| MG | 0.64 | -0.22 | -0.17 |
| Hip Disp | 0.66 | 0.54 | -0.18 |
| Knee Disp | 0.56 | 0.68 | 0.18 |
| Variance | 32.8 | 20.6 | 15.2 |

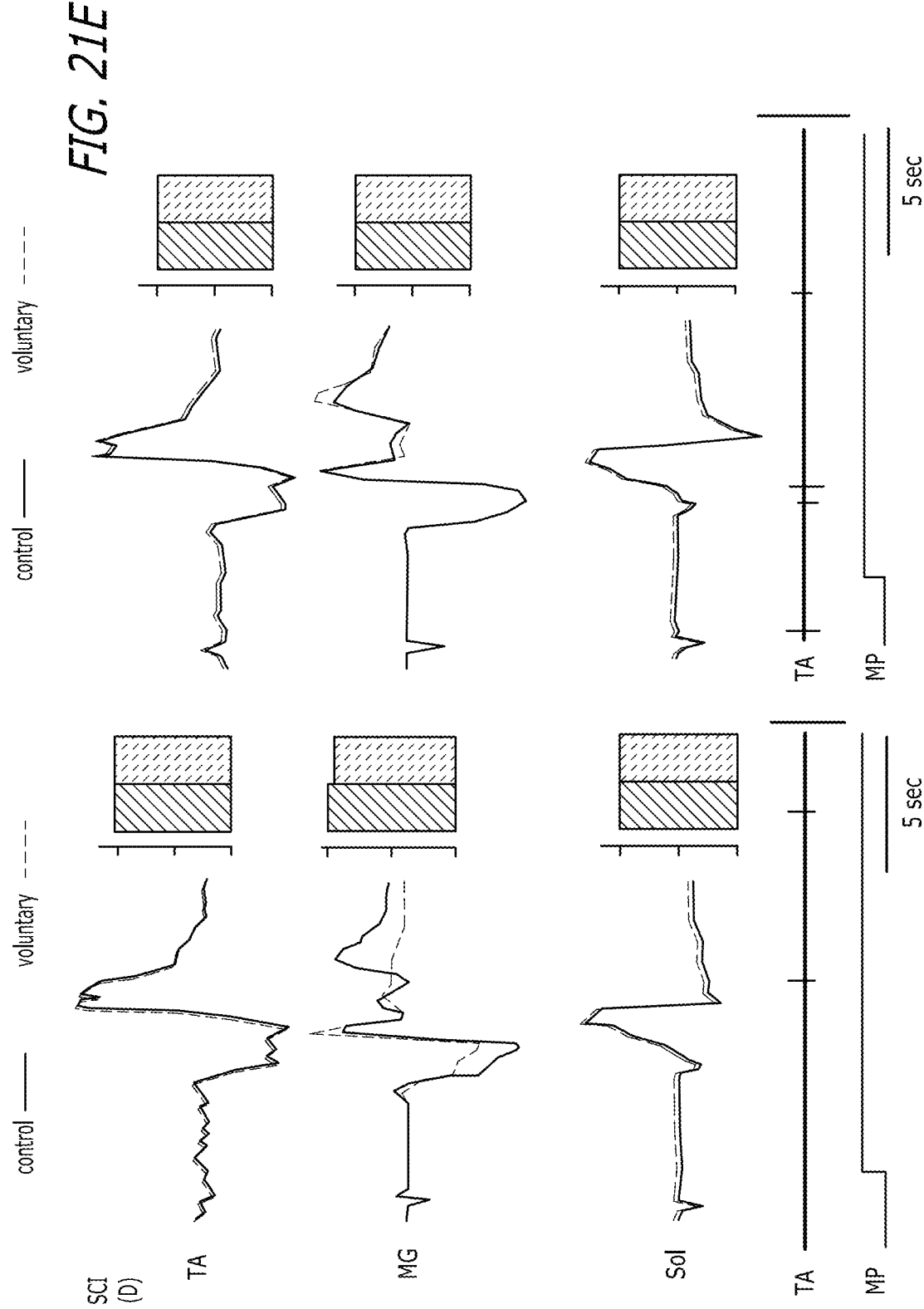

TRANSCUTANEOUS NEUROMODULATION SYSTEM AND METHODS OF USING SAME

PRIORITY CLAIM

The present application is a continuation of U.S. patent application Ser. No. 17/140,896, filed Jan. 4, 2021, now U.S. Pat. No. 11,638,820, which is a continuation of Ser. No. 16/153,472, filed Oct. 5, 2018, now U.S. Pat. No. 10,881,853, which is a continuation of U.S. patent application Ser. No. 14/925,791, filed Oct. 28, 2015, now U.S. Pat. No. 10,092,750, which claims priority to U.S. Provisional Patent Application No. 62/069,590, filed Oct. 28, 2014, the entire disclosure of which are incorporated herein by reference.

U.S. patent application Ser. No. 14/925,791 is also a continuation-in-part of U.S. patent application Ser. No. 14/357,481, filed May 9, 2014, now U.S. Pat. No. 9,393,409, which is a national stage entry of International Patent Application PCT/US2012/064874, filed Nov. 13, 2012, which claims priority to and benefit to U.S. Provisional Patent Application No. 61/559,025, filed Nov. 11, 2011, the entire disclosure of each of which are incorporated herein by reference.

SUMMARY

Described herein generally are neuromodulation systems used with or on a mammal (e.g., a human) having a spinal cord with at least one selected dysfunctional spinal or neural circuit or other neurologically derived source of function or movement control in a portion of the subject's (e.g., mammal) body. The systems can be transcutaneous systems and can induce voluntary movement in a mammal with a spinal cord injury.

In one embodiment, the neuromodulation systems can include: a processor; a signal generator; and at least one electrode. The electrode(s) can be transcutaneous electrodes. In other embodiments, in addition to transcutaneous electrodes, one or more implantable electrodes can be included in the system. In some embodiments, the processor, in cooperation with the signal generator and the at least one electrode are configured to deliver a stimulation to a mammal, the stimulation including a monophasic or biphasic signal and an overlapping high frequency pulse thereby inducing voluntary movement.

Methods of using the herein described systems are also disclosed. The methods can include: applying a stimulation including a biphasic signal and an overlapping high frequency pulse to a mammal using a transcutaneous neuromodulation system thereby inducing the voluntary movement. In some embodiments, the stimulation can be monopolar or bipolar.

In some embodiments, the voluntary movement is of a foot, a toe, a knee, a leg, a neck, a shoulder, an arm, a hand, a finger, a waist or a combination thereof. In other embodiments, the voluntary movement comprises at least one of standing, stepping, a walking motor pattern, sitting down, laying down, reaching, grasping, pulling and pushing, taking a breath, chewing or swallowing.

In one embodiment, the biphasic signal is a 0.5-100 Hz signal that can be delivered at 0.5-200 mA. The overlapping high frequency pulse can be a 10 kHz pulse or a 5 kHz pulse.

The stimulation can be applied over a cervical portion of the spinal cord or the brainstem. The delivered signal can also be applied paraspinally over at least one of a cervical-thoracic portion, a thoracic portion, a thoracic-lumbar portion, lumbar portion, a lumbosacral portion and a sacral portion of the spinal cord. Further still, the delivered signal is applied to a T11-T12 vertebrae.

In some embodiments, the systems can be used on or for mammals, such as humans, having a neurodegenerative brain injury or disease. The neurodegenerative brain injury or disease can be a brain injury associated with a condition selected from Parkinson's disease, Huntington's disease, Alzheimer's, ischemia, stroke, dystonia, amyotrophic lateral sclerosis (ALS), primary lateral sclerosis (PLS) or other neurological disorders such as cerebral palsy.

In some embodiments, the delivered stimulation can be referred to as transcutaneous electrical spinal cord stimulation (tESCS) or painless cutaneous enabling motor control (pcEmc) and are used interchangeably herein. The stimulation can be applied in the region of the T11-T12 vertebrae with a frequency of 5-40 Hz and may elicit voluntary step-like movements in healthy subjects with their legs suspended in a gravity-neutral position. Amplitude of evoked step-like movements may increase with increasing tESCS or pcEmc frequency. Frequency of evoked step-like movements may not depend on the frequency of tESCS or pcEmc.

In some embodiments, tESCS or pcEmc can be used as a noninvasive method in rehabilitation of spinal pathology. By way of non-limiting examples, application of tESCS or pcEmc activates spinal networks (SNs), in part via the dorsal roots and the gray matter of the spinal cord. When activated, the SNs may (a) enable voluntary movement of muscles involved in at least one of standing, stepping, reaching, grasping, voluntarily changing positions of one or both legs, breathing, swallowing, chewing, coughing, speech control, voiding the patient's bladder, voiding the patient's bowel, postural activity, and locomotor activity; (b) enable or improve autonomic control of at least one of cardiovascular function, body temperature, and metabolic processes; (c) help facilitate recovery of at least one of an autonomic function, sexual function, vasomotor function, and cognitive function; and/or (d) help to resolve and/or block pain and spasm, and improve or restore sensory function.

The paralysis may be a motor complete paralysis or a motor incomplete paralysis. The paralysis may have been caused by a spinal cord injury classified as motor complete or motor incomplete. The paralysis may have been caused by an ischemic or traumatic brain injury. The paralysis may have been caused by an ischemic brain injury that resulted from a stroke or acute trauma. By way of another example, the paralysis may have been caused by a neurodegenerative brain injury. The neurodegenerative brain injury may be associated with at least one of Parkinson's disease, Huntington's disease, Alzheimer's, dystonia, ischemia, stroke, amyotrophic lateral sclerosis (ALS), primary lateral sclerosis (PLS), and cerebral palsy. In another embodiment, the paralysis may have been caused or induced by a reaction to a drug, a prescribed or holistic medication, vitamin, or mineral supplement. In one example embodiment, the paralysis may have been caused or induced by a reaction to an anesthetic drug.

In one example embodiment, a neuromodulation system may be configured to apply electrical stimulation to a portion of a spinal cord of the subject. The electrical stimulation may be applied by at least one electrode that is applied to the skin surface of the subject. Such an electrode may be positioned on at least one of a thoracic region, a cervical region, a lumbosacral region, a sacral region of the spinal cord, and/or the brainstem. Electrical stimulation may be delivered at 1-40 Hz at 1-200 mA. The electrical stimulation may include at least one of tonic stimulation and intermittent stimulation. The electrical stimulation may include simultaneous or sequential stimulation of different regions of the spinal cord.

In one example embodiment, where the paralysis was caused by a spinal cord injury at a first location along the spinal cord, the electrical stimulation may be applied by an electrode that is on the spinal cord of the patient at a second location below the first location along the spinal cord relative to the patient's brain. In other words, the at least one electrode can be placed below a site of spinal injury.

In one embodiment, the systems and methods described herein may include stimulation and/or recording of a second or multiple electrode(s) placed on or over a muscle, nerve, on or near a target end organ or bodily structure. In some embodiments, this second or multiple electrode(s) may be placed transcutaneously or can be implanted. The additional electrode(s) can be in communication with the first electrode through a connection to the first electrode control module by means of either a hardwire or wireless connection. In another embodiment, the second electrode or multiple electrode(s) may be implanted within the subject in various locations and to various depths on, over or near a muscle, nerve, or target end organ.

In one embodiment, methods may include administering one or more active agents or drugs to the patient. In one embodiment, the active agent or drug can be a neuropharmaceutical agent. The neuropharmaceutical agent(s) may include at least one of a serotonergic drug, a dopaminergic drug, a noradrenergic drug, a monoaminergic drug, GABAergic drug, and glycinergic drugs. By way of non-limiting examples, the neuropharmaceutical agents may include at least one of 8-OHDPAT, Way 100.635, Quipazine, Ketanserin, SR 57227A, Ondanesetron, SB 269970, Buspirone, Methoxamine, Prazosin, Clonidine, Yohimbine, SKF-81297, SCH-23390, Quinpirole, and/or Eticlopride.

The neuropharmaceutical agent may be administered orally, or by intramuscular, intravenous, or intrathecal injection. In other embodiments, the neuropharmaceutical agent may be administered rectally or topically such as a transdermal liquid, cream, or ointment. In embodiments, the agent can be administered via a drug pump and the administrative pump may be in communication and under control of the electric stimulator control module.

The electrical stimulation may be defined by a set of parameter values, and activation of the selected spinal circuit may generate a quantifiable result. In one example embodiment, the neuromodulation system is configured to repeat and use electrical stimulation having different sets of parameter values to obtain quantifiable results generated by each repetition. Thereafter, a machine learning method may be executed by at least one computing device. The machine learning method can build a model of a relationship between the electrical stimulation applied to the spinal cord and the quantifiable results generated by activation of the at least one spinal circuit. A new set of parameters may be selected based on the model. By way of a non-limiting example, the machine learning method may implement a Gaussian Process Optimization or a "Dueling Bandit" machine learning paradigm.

In one example embodiment, the neuromodulation system can be configured to enable at least one function selected from a group consisting of postural and/or locomotor activity, voluntary movement of leg position, when not bearing weight, improved ventilation, swallowing, speech control, voluntary voiding of the bladder and/or bowel, return of sexual function, autonomic control of cardiovascular function, body temperature control, and normalized metabolic processes, in a human subject having a neurologically derived paralysis. In one embodiment, the neuromodulation system can be configured to enable voluntary movement or voluntary bodily functions.

Methods can include stimulating a subject's spinal cord using at least one surface electrode and may include simultaneously subjecting the subject to physical training that exposes the subject to relevant postural proprioceptive signals, locomotor proprioceptive signals, and supraspinal signals while being stimulated with tESCS or pcEmc. In other embodiments, the methods may also include the delivery of a drug. At least one of the stimulation and physical training modulates, provokes or incites in real time the electrophysiological properties of spinal circuits in the subject so the spinal circuits are activated by at least one of supraspinal information and proprioceptive information derived from the region of the subject where the selected one or more functions are facilitated.

The region where the selected one or more functions are facilitated may include one or more regions of the spinal cord that control: (a) lower limbs; (b) upper limbs and brainstem for controlling speech; (c) the subject's bladder; and/or (d) the subject's bowel and/or other end organ. The physical training may include standing, stepping, sitting down, lying down, reaching, grasping, stabilizing sitting posture, stabilizing standing posture, practicing speech, swallowing, chewing, deep breathing, and coughing.

The surface electrode may include an array of one or more electrodes stimulated in a monopolar biphasic configuration. Such a surface electrode may be placed over at least one of a lumbar, a lumbosacral or sacral portion of the spinal cord, a thoracic portion of the spinal cord, a cervical portion of the spinal cord, and/or the brainstem.

The stimulation may include continuous stimulation and/or intermittent stimulation. The stimulation may include simultaneous or sequential stimulation of different spinal cord regions. Optionally, the stimulation pattern may be under control of the subject.

The physical training may include inducing a load bearing positional change in the region of the subject where locomotor activity is to be facilitated. In other embodiments, the physical training may include inducing a load bearing positional change in the region of the subject where voluntary locomotor activity is to be facilitated. The load bearing positional change in the subject may include standing, stepping, reaching, and/or grasping. The physical training may include robotically guided training.

In one example embodiment, a method includes placing an electrode on the patient's spinal cord, positioning the patient in a training device configured to assist with physical training that is configured to induce neurological signals derived from the portion of the patient's body having motor dysfunction, and applying electrical stimulation to a portion of a spinal cord of the patient.

Another exemplary embodiment is a system that includes a training device configured to assist with physically training the patient, at least one surface electrode array configured to be applied on the patient's spinal cord, and a stimulation generator connected to the electrode. When undertaken, the physical training induces neurological signals derived from the portion of the patient's body having the motor dysfunction. The stimulation generator is configured to apply electrical stimulation to the electrode. In some embodiments, the system can induce voluntary movements as described herein.

In another embodiment, the stimulation or stimulator generator connected to the at least one electrode is also configured to communicate with an exercise device. The stimulation or stimulator generator can also be configured to receive, transmit and/or store data thereby creating a closed loop system. When undertaking physical training, the stimulator can auto adjust the stimulation parameters based on the interpretation of the data collected.

Additional features and advantages are described herein, and will be apparent from the following Detailed Description and figures.

BRIEF DESCRIPTION OF THE DRAWINGS

FIG. 2A: Subject R: the cinematogramms of the joint movements of the right leg and the EMGs of the hip muscles of the right and left legs are shown. Under the EMG, there is a mark of the stimulus. At the right of the cinematogram and EMGs, there are vertical marks of the amplitude in angle degrees and mV, respectively. The duration of records is 40 s. FIG. 2B: Subject S: the EMGs of the hip and ankle muscles of the right leg and the goniograms of the knee joints of the right and left legs; the arrows at the top show the beginning and end of stimulation; the horizontal and vertical labels next to EMG, 10 s and 0.5 mV, respectively; the vertical mark to the right of the goniograms, 200 m V. H, hip; Kn, knee; Ank, ankle; RF, m. rectus femoris; BF, m. biceps femoris; T A, m. tibialis anterior; M G, m. gastrocnemius; (r), on the right; (1), on the left.

FIG. 14A illustrates the position of the legs of a paralyzed subject when in the gravity-neutral apparatus. FIG. 14B illustrates mean±SEM (n=5 subjects) angular displacements of the hip and knee at the Pre-Train and Post-Drug phases. Hamstring (HM), tibialis anterior (TA), and medial gastrocnemius (MG) raw EMG and angular displacement at the knee during leg movements in the presence of stimulation at T11, Co1, or T11+Co1 at the Pre-Train ($t_1$) and Post-Drug ($t_6$) phases is shown. Arrows indicate the time the stimulation is turned on. A "*" indicates that results are significantly different from Pre-Train at P<0.05.

FIG. 15B illustrates mean±SEM (n=5 subjects) knee angular displacements at the Pre-Train ($t_1$), Post-Train ($t_2$), and Post-Drug ($t_6$) phases under each condition described in (FIG. 15A) and (FIG. 15B). The dashed and dotted dashed horizontal lines indicate the mean voluntary effort at $t_1$ and $t_2$, respectively. The percentiles in $t_6$ reflect differences between $t_6$ and $t_1$ and $t_6$ and $t_2$, respectively. An "*" indicates a result that is significantly different from Vol; ‡, significantly different from Stim; An "" indicates a result that is significantly different from Vol at ($t_1$); ‡‡, significantly different from Vol+Stim at ($t_1$). An "" indicates a result that is significantly different from Vol at ($t_2$); ‡‡, significantly different from Vol+Stim at ($t_2$), all at P<0.05.

FIG. 16B illustrates a nonlinear principal component analysis (NL-PCA) to distill non-parametric multivariate kinematics cross-correlations into principal component (PC) patterns. PC loading matrix depicts the relationship between variables and the extracted PC patterns. Positive loadings are red and inverse loadings are blue. Loading weights were used to calculate PC scores. FIG. 16C illustrates three-way repeated measures ANOVA for testing the impact of Stim, Vol, and Vol+Stim on the improvement of the kinematics based on the PC1 score. FIG. 16C illustrates interaction of Stim by Drug modulation on the improvement of the kinematics based on the PC1 score: significance was assessed by factorial 3-way within subjects ANOVA followed by post-hoc one-way ANOVA and Tukey's test. An "*" represents a value significantly different from Vol; ‡, significantly different from Stim; ‡‡, significantly different from Pre-Train. ‡‡, significantly different from Post-Train, all at P<0.05.

FIGS. 17A-17O illustrate voluntary oscillatory limb activity at different phases of the study. FIG. 17A illustrates an example of VL and HM EMG activity and hip and knee displacements during voluntary leg oscillations without pcEmc for Subject 1 during the Pre-Train ($t_1$) and Post-Drug ($t_5$) phases.

FIG. 18A illustrates raw EMG from the TA and MG muscles under the influence of stimulation at T11, Co1, and T11+Co1 with and without voluntary effort to oscillate the legs (flexion-extension-flexion) when placed in a gravity-neutral position. FIG. 18B illustrates evoked potentials generated within the shaded areas in FIG. 18A without and with voluntary effort. The sequence of traces is triggered from the stimulation pulse with the lowest trace being the first and the top trace being the last response. FIG. 18C illustrates an overlay of multiple responses (T11, 0-33 ms and Co1, 0-200 ms) during flexion and extension without and with voluntary effort. FIG. 18D illustrates a schematic summary of the variations in 20-35 ms TA (Flexor-F) and MG (Extensor-E) responses (see FIG. 18B) reflects how spinally evoked potentials can be gated with voluntary input. The dotted lines reflect minimal or no evoked potential and the thin and thick solid lines indicate modest and high amplitude evoked potentials. Generally Co1 stimulation evoked more consistent responses in both muscles than T11 or T11+Co1 stimulation.

FIG. 19A illustrates an example of raw EMG and hip and knee angular displacements from the first and last 30 sec of conditioning without and with stimulation at T11. FIG. 19B illustrates scatter plots between filtered EMG activity of antagonistic muscle pairs (VL vs. HM, TA vs. Soleus and TA vs. MG) for the first 5 sec from each segment illustrated in FIG. 19A. FIG. 19C illustrates when NL-PCA was used to distill non-parametric multivariate kinematics cross-correlations into PC patterns. PC loading matrix depicts the relationship between variables and the extracted PC patterns. FIG. 19D illustrates three-way repeated measures ANOVA of the impact of Vol, Stim, and Vol+Stim using PC1 outcome as the endpoint. FIG. 19D illustrates the interaction of Stim by Conditioning modulation. ‡, significantly different from Stim; ‡‡, significantly different Pre-Cond, all at P<0.05.

FIGS. 21A-21F illustrate an electrophysiological assessment of injury severity. EMG from the TA, MG and soleus was recorded with and without a maximum voluntary effort to dorsiflex or plantarflex with pcEmc at T11. The histograms indicate peak-to-peak amplitudes of the evoked potentials in the absence of voluntary effort (dark) and in the presence of voluntary effort (light). FIG. 21a illustrates results from an uninjured subject. FIGS. 21B-21F illustrate SCI subjects identification in parentheses. MP, manual pulse to generate the dorsiflexion or plantarflexion effort. Electrophysiological assessment of injury severity. EMG from the TA, MG and soleus was recorded with and without a maximum voluntary effort to dorsiflex or plantarflex with pcEmc at T11. The histograms indicate peak-to-peak amplitudes of the evoked potentials in the absence of voluntary effort (dark) and in the presence of voluntary effort (light). MP is manual pulse to generate the dorsiflexion or plantarflexion effort.

DETAILED DESCRIPTION

Figure 1:
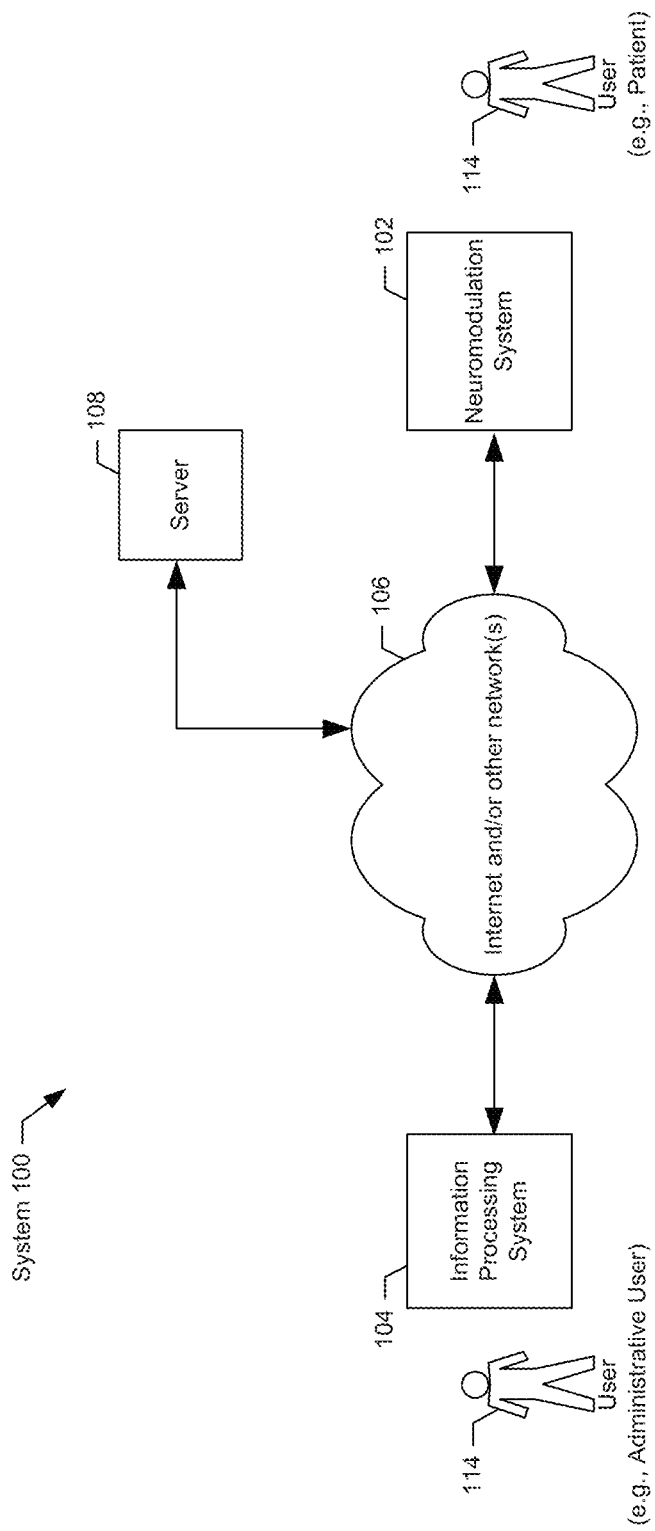
FIG. 1 is a high level block diagram of an example network communicating system, according to an example embodiment of the system disclosed herein.

The present disclosure relates in general to the field of neurological treatment and rehabilitation for injury and disease including traumatic spinal cord injury, non-traumatic spinal cord injury, stroke, movement disorders, brain injury, and other diseases or injuries that result in paralysis and/or nervous system disorder. Systems and devices are provided to facilitate recovery of posture, locomotion, and voluntary movements such as those of the arms, trunk, and legs, and recovery of autonomic, sexual, vasomotor, speech, swallowing, chewing, respiratory and cognitive function, in a human subject having spinal cord injury, brain injury, or any other neurological disorder.

Described herein generally are stimulation strategies and methods of pcEmc or tESCS and optionally a pharmacological enabling motor control (fEmc) strategy to neuromodulate the physiological state of the spinal cord in individuals with paralysis, for example, motor complete paralysis. The strategies can assist in regaining some voluntary locomotor-like leg movements after motor complete paralysis or other voluntary movements of body parts affected by spinal cord injury.

Systems for delivering stimulation are also described. The systems can electrically activate the spinal circuitry via electrodes placed on the skin overlying the spinal cord such as the lower thoracic and lumbosacral vertebrae.

The systems and methods can also include the administration of at least one drug. In some embodiments, the drug is a monoaminergic drug. In some embodiments, the monoaminergic drug can be administered in combination with stimulation (e.g., pcEmc+fEmc) to provide voluntarily movement, such as but not limited to step-like movements of the lower limbs. In some embodiments, the monoaminergic drug can be buspirone.

Further, the results provided herein demonstrate the presently described systems and methods' ability to bring about voluntary movement in a patient with motor complete paralysis. However, in some embodiments, there herein described systems and methods can bring about voluntary movement in a patient with motor incomplete paralysis.

These systems and methods can transform brain-spinal neuronal networks from a dormant to a functional state sufficiently to enable recovery of voluntary movement. In some embodiments, the systems and methods facilitate voluntary control of locomotor-like stepping with pcEmc or tESCS and optionally fEmc.

For example, in some embodiments, a single treatment session with pcEmc or tESCS and fEmc three minutes of passive movements can further facilitate voluntary outputs. Also, in some embodiments, spinally evoked motor potentials can be readily modulated voluntarily, providing functional and electrophysiological evidence of the re-establishment of connectivity among neural networks between the brain and the spinal cord.

The devices and methods described herein can re-engage descending input that projects to spinal locomotor networks after partial or complete motor paralysis. The present systems and methods can use pcEmc or tESCS and optionally fEmc. In some embodiments, pcEmc or tESCS and optionally fEmc are combined with training. When used with training, a re-engaging of descending input that projects to spinal locomotor networks can result. Thus, in some embodiments, inducement of voluntary movement of body parts can result.

The systems and methods can enable movement to occur voluntarily rather than being induced directly by stimulation. For example, pcEmc or tESCS optionally coupled with fEmc can enable the re-engagement of a progressively increasing complex neural network, providing the substrate for previously dormant circuitry to regain function. Although in some embodiments, some dysfunctional reorganization of the networks can occur after a spinal cord injury thereby limiting the recovery of coordinated movements, re-engagement may not be prevented. The quality of the recovered coordination reflects some aberrant and/or limited connectivity of the newly emerged descending control of the spinal networks.

In some embodiments, when combining pcEmc or tESCS and optionally fEmc with training, both animal and human results can show more normal levels of coordination and/or recruitment of motor pools. In some embodiments, the training can be extensive training. In some embodiments, more normal levels of coordination and/or recruitment of motor pools can be realized at least during movements such as stepping can be recovered.

In some embodiments, functional brain-to-spinal cord connectivity in completely paralyzed individuals can be facilitated with electrical and/or pharmacological neuromodulation when presented concomitantly with training of neural networks that control stepping-like movements.

In some embodiments, when combining pcEmc or tESCS and/or fEmc with training, the systems and methods can provide improvements in functional measures of spinal cord injury converting subjects from motor complete (AIS B) to motor incomplete (AIS C), such as within a relatively short period of time. For example, as described herein, in 5/5 individuals assumed to be completely paralyzed, two non-invasive interventions can facilitate recovery of voluntarily controlled sensorimotor function. Also, given anatomical and physiological incompleteness of spinal cord injuries typically diagnosed otherwise as "completely paralyzed" places some sense of urgency in resolving the uncertainty of the diagnosis and treatment strategies that should be followed after paralysis.

The present systems and methods can improve postural, locomotor, and other functions that are directly defined by the individual's mobility. For example improvements can be attained in autonomic function of multiple physiological systems, such as improved cardiovascular and bladder control, sexual function, and temperature regulation.

The systems described herein may be readily realized in a network communications system. A high level block diagram of an example network communications system 100 ("system 100") is illustrated in FIG. 1. In this example, system 100 includes neuromodulation system 102 and information processing system 104.

Information processing system 104 may include a variety of devices, such as desktop computers which typically include a user display for providing information to users and various interface elements as will be discussed in further detail below. Information processing system 104 may include a cellular phone, a personal digital assistant, a laptop computer, a tablet computer, or a smart phone. In some example embodiments, information processing system 104 may include any mobile digital device such as a smartphone, cellular phone, tablet, laptop computer, ultrabook computer, pager, or the like. Further, information processing system 104 may include smart phones based on various commercially available operating systems. In these embodiments, information processing system 104 is preferably configured to download, install and execute various application programs.

Information processing system 104 may communicate with neuromodulation system 102 via a connection to one or more communications channels 106 such as the Internet or some other data network, including, but not limited to, any suitable wide area network or local area network. It should be appreciated that any of the devices and systems described herein may be directly connected to each other instead of over a network. At least one server 108 may be part of network communications system 100, and may communicate with neuromodulation system 102 and information processing system 104.

Information processing system 104 may interact with a large number of users at a plurality of different neuromodulation systems 102. Accordingly, information processing system 104 may be a high end computer with a large storage capacity, one or more fast microprocessors, and one or more high speed network connections. Conversely, relative to an example high end information processing system 104, each neuromodulation system 102 may include less storage capacity, a single microprocessor, and a single network connection.

It should be appreciated that users as described herein may include any person or entity which uses the presently disclosed system and may include a wide variety of parties. For example, the users described herein may refer to various different entities, including patients, physicians, administrative users, mobile device users, private individuals, and/or commercial partners. It should also be appreciated that although the user in this specification is often described as a patient, the patient may be instead any of the users described herein.

Neuromodulation system 102 and/or servers 108 may store files, programs, databases, and/or web pages in memories for use by information processing system 104, and/or other information processing systems 104 or servers 108.

Neuromodulation system 102 and/or server 108 may be configured according to its particular operating system, applications, memory, hardware, etc., and may provide various options for managing the execution of the programs and applications, as well as various administrative tasks. Information processing system 104 and/or server 108 may interact via at least one network with at least one other information processing system 104 and/or server 108, which may be operated independently. Information processing systems 104 and servers 108 operated by separate and distinct entities may interact together according to some agreed upon protocol.

Figure 2:
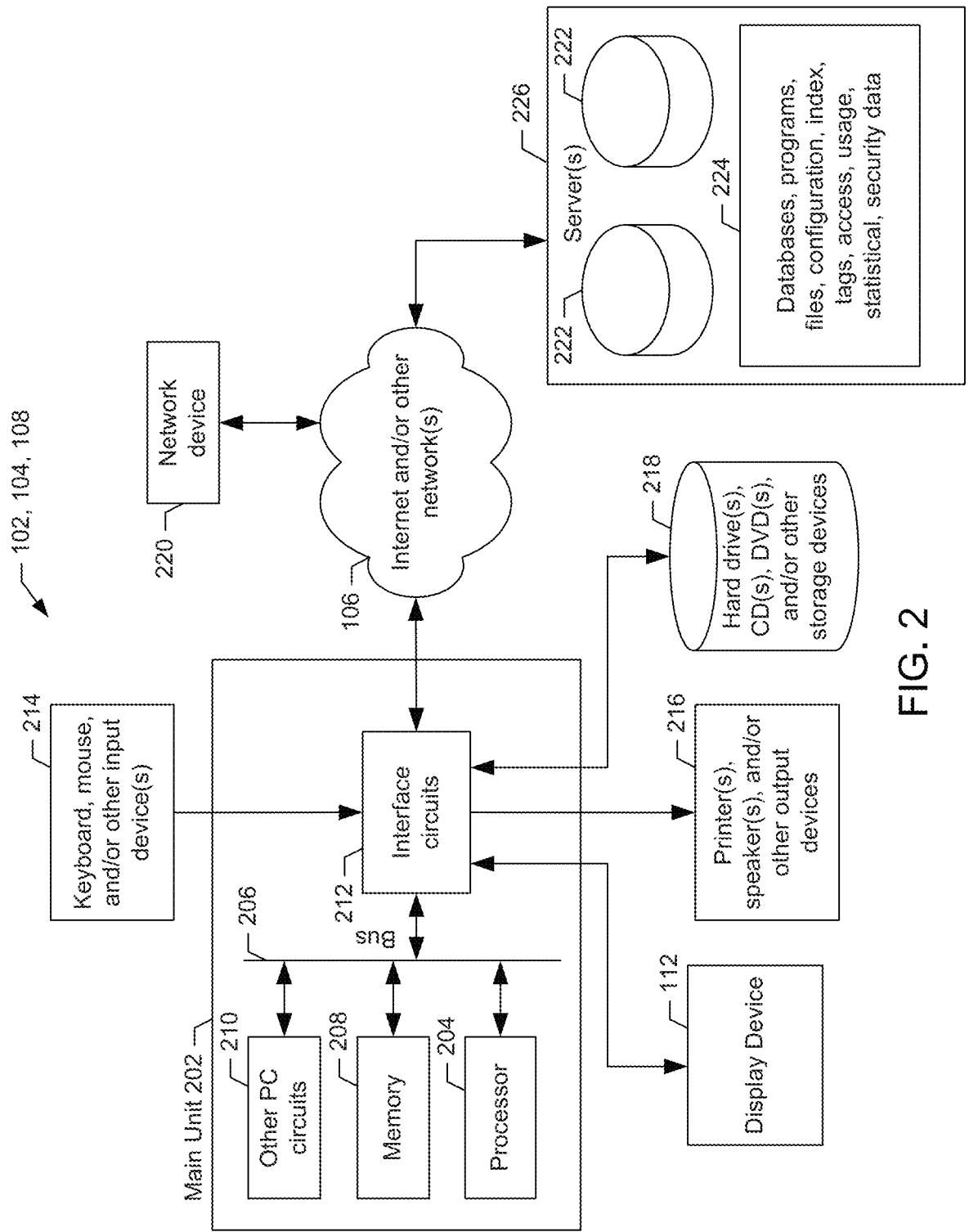
FIG. 2 is a detailed block diagram showing an example of a computing device, according to an example embodiment of the system disclosed herein.

A detailed block diagram of the electrical systems of an example computing device is illustrated in FIG. 2. The example computing device may include any of the devices and systems described herein, including neuromodulation system 102, information processing system 104 and server 108. In this example, the example computing devices may include main unit 202 which preferably includes at least one processor 204 electrically connected by address/data bus 206 to at least one memory device 208, other computer circuitry 210, and at least one interface circuit 212. Processor 204 may be any suitable processor. Processor 204 may include one or more microprocessors, central processing units (CPUs), computing devices, microcontrollers, digital signal processors, or like devices or any combination thereof. Memory 208 preferably includes volatile memory and non-volatile memory. Preferably, memory 208 stores software program(s) that interact with the other devices in system 100 as described below. This program may be executed by processor 204 in any suitable manner. In an example embodiment, memory 208 may be part of a "cloud" such that cloud computing may be utilized by neuromodulation system 102, information processing system 104 and server 108. Memory 208 may also store digital data indicative of documents, files, programs, web pages, etc. retrieved from computing devices 102, 103 and 104 and/or loaded via input device 214.

Interface circuit 212 may be implemented using any suitable interface standard, such as an Ethernet interface and/or a Universal Serial Bus (USB) interface. At least one input device 214 may be connected to interface circuit 212 for entering data and commands into main unit 202. For example, input device 214 may be at least one of a keyboard, mouse, touch screen, track pad, track ball, isopoint, image sensor, character recognition, barcode scanner, and a voice recognition system.

As illustrated in FIG. 2, at least one display device 112, printers, speakers, and/or other output devices 216 may also be connected to main unit 202 via interface circuit 212. Display device 112 may be a cathode ray tube (CRTs), a liquid crystal display (LCD), or any other suitable type of display device. Display device 112 may be configured to generate visual displays during operation of neuromodulation system 102, information processing system 102 and/or server 108. A user interface may include prompts for human input from user 114 including links, buttons, tabs, checkboxes, thumbnails, text fields, drop down boxes, etc., and may provide various outputs in response to the user inputs, such as text, still images, videos, audio, and animations.

At least one storage device 218 may also be connected to main device or unit 202 via interface circuit 212. At least one storage device 218 may include at least one of a hard drive, CD drive, DVD drive, and other storage devices. At least one storage device 218 may store any type of data, such content data, statistical data, historical data, databases, programs, files, libraries, pricing data and/or other data, etc., which may be used by neuromodulation system 102, information processing system 104 and/or server 108.

Neuromodulation system 102, information processing system 104 and/or server 108 may also exchange data with other network devices 220 via a connection to network 106. Network devices 220 may include at least one server 226, which may be used to store certain types of data, and particularly large volumes of data which may be stored in at least one data repository 222. Server 226 may include any kind of data 224 including user data, application program data, content data, statistical data, historical data, databases, programs, files, libraries, pricing data and/or other data, etc. Server 226 may store and operate various applications relating to receiving, transmitting, processing, and storing the large volumes of data. It should be appreciated that various configurations of at least one server 226 may be used to support and maintain system 100. In some example embodiments, server 226 is operated by various different entities, including private individuals, administrative users and/or commercial partners. Also, certain data may be stored in neuromodulation system 102, information processing system 104 and/or server 108 which is also stored on server 226, either temporarily or permanently, for example in memory 208 or storage device 218. The network connection may be any type of network connection, such as an Ethernet connection, digital subscriber line (DSL), telephone line, coaxial cable, wireless connection, etc.

Access to neuromodulation system 102, information processing system 104 and/or server 108 can be controlled by appropriate security software or security measures. A user's access can be defined by neuromodulation system 102, information processing system 104 and/or server 108 and be limited to certain data and/or actions. Accordingly, users of system 100 may be required to register with neuromodulation system 102, information processing system 104 and/or server 108.

As noted previously, various options for managing data located within neuromodulation system 102, information processing system 104 and/or server 108 and/or in server 226 may be implemented. A management system may manage security of data and accomplish various tasks such as facilitating a data backup process. The management system may update, store, and back up data locally and/or remotely. A management system may remotely store data using any suitable method of data transmission, such as via the Internet and/or other networks 106.

Figure 3:
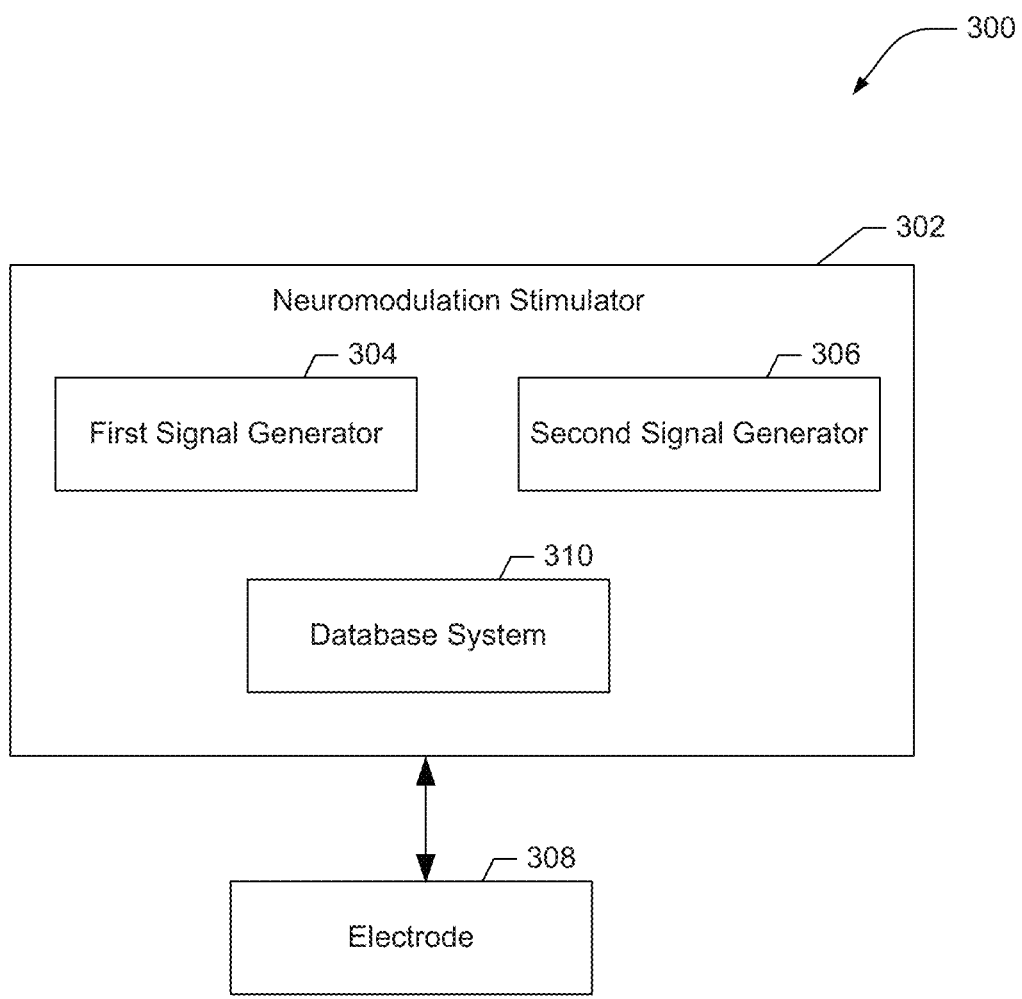
FIG. 3 is a block diagram of an example neuromodulation system in accordance with one example embodiment of the system disclosed herein.

FIG. 3 is a block diagram showing an example neuromodulation system 300. It should be appreciated that neuromodulation system 300 illustrated in FIG. 3 may be implemented as neuromodulation system 102.

As illustrated in FIG. 3, in this example, neuromodulation system 300 may include neuromodulation stimulator device 302 which is operatively connected to at least one electrode 308. Neuromodulation stimulator device 302 may be connected to at least one electrode 308 in any suitable way. In one example, neuromodulation stimulator device 302 is directly connected to at least one electrode 308. In another example, where at least one electrode 308 is implanted, neuromodulation stimulator device 302 is connected to at least one electrode 308 via a wireless connection.

Referring to FIG. 3, in this example, neuromodulation stimulator device 302 includes first signal generator 304, second signal generator 306 and database system 310. First signal generator 304, second signal generator 306 and database system 310 may include software and/or hardware components, such as a field programmable gate array (FPGA) or an application specific integrated circuit (ASIC), which performs certain tasks. First signal generator 304, second signal generator 306 and database system 310 may advantageously be configured to reside on an addressable storage medium and configured to be executed on one or more processors. Thus, first signal generator 304, second signal generator 306 and database system 310 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules.

Database system 310 may include a wide variety of data. For example, database system may include any of the following data: user data, application program data, content data, statistical data, historical data, databases, programs, files, libraries, pricing data and/or other data, etc.

In some example embodiments, at least one electrode 308 includes single or multiple arrays and may be placed on the skin overlying the spinal cord, spinal nerve(s), nerve root(s), ganglia, peripheral nerve(s), brain stem or target areas such as skeletal muscles.

In some embodiments, the at least one electrode is made of a conducting gel or reservoir of water soluble/salt solution. In some embodiments, the implantable electrodes are made of biocompatible material such as silicone and may be embedded with an inert metal such as gold or platinum wires.

Figure 4:
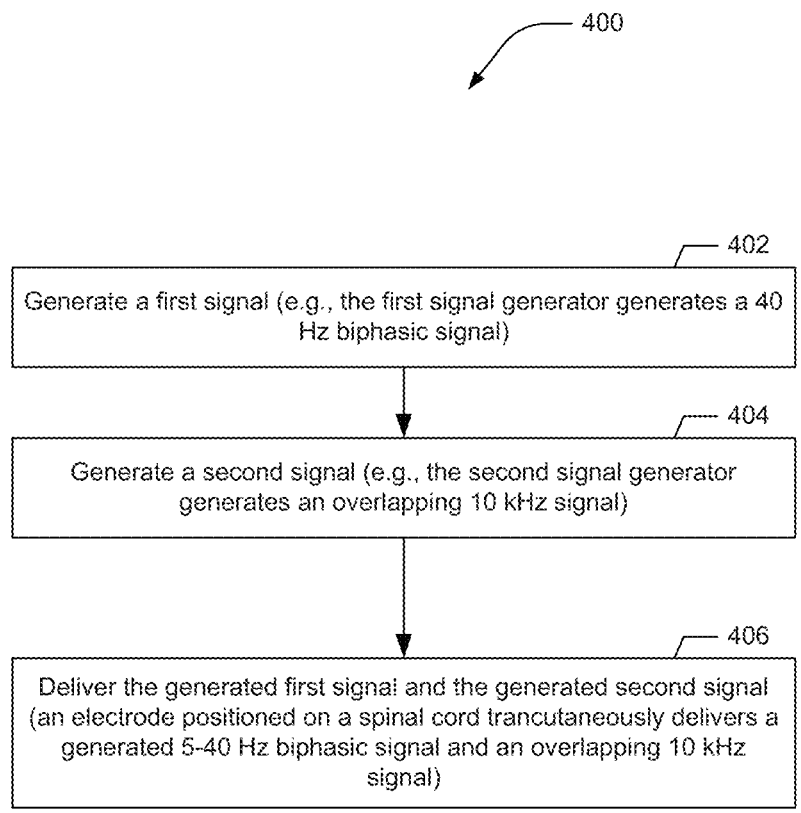
FIG. 4 is a flowchart illustrating an example procedure for delivering a generated first signal and a generated second signal.

As illustrated in FIG. 4, a flowchart of an example process 400 includes delivering a generated first signal and a generated second or overlapping signal. Process 400 may be embodied in one or more software programs which are stored in one or more memories and executed by one or more processors. Although process 400 is described with reference to the flowchart illustrated in FIG. 4, it should be appreciated that many other methods of performing the acts associated with process 400 may be used. For example, the order of many of the steps may be changed, some of the steps described may be optional, and additional steps may be included.

More specifically, in one example, the neuromodulation system generates a first signal, as indicated by block 402. For example, first signal generator 302 may generate a 40 Hz biphasic signal.

As indicated by block 404, the neuromodulation system generates a second signal. For example, second signal generator 304 may generate an overlapping 10 kHz signal.

As indicated by block 406, the neuromodulation system delivers the generated first signal and the generated second signal. For example, the neuromodulation system may transcutaneously deliver, via an electrode positioned on a spinal cord, the generated 40 Hz biphasic signal with the overlapping 10 kHz signal.

Figure 5A:
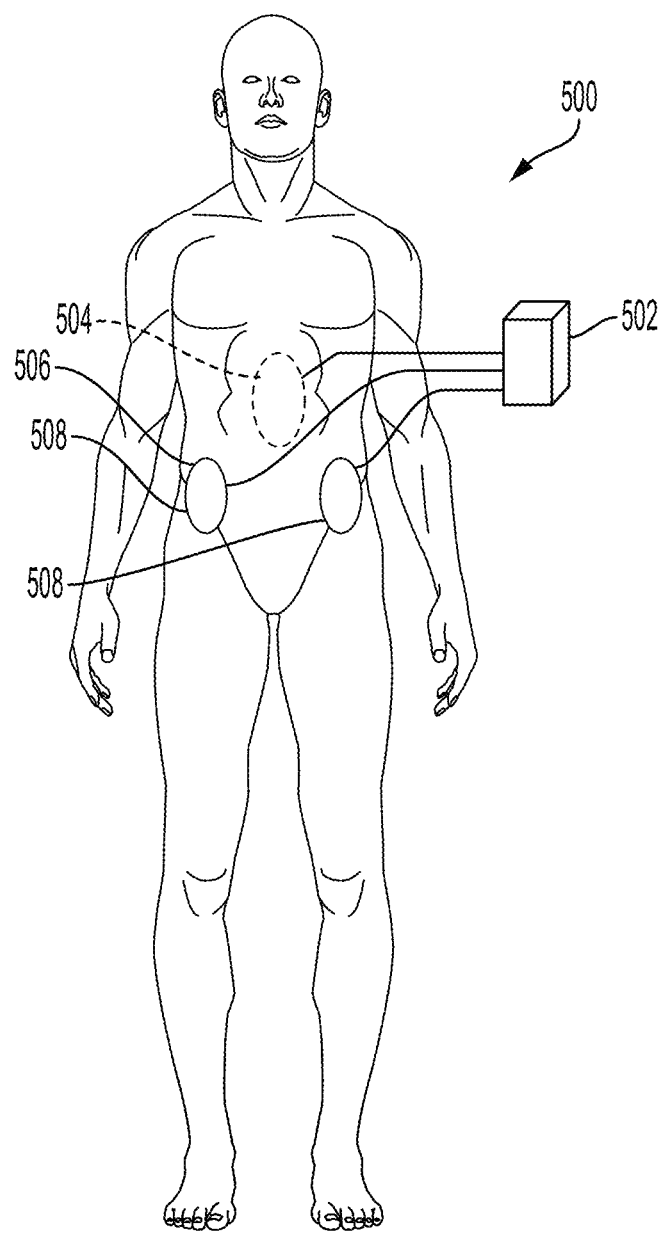
FIGS. 5A and 5B are diagrammatic views of an example neuromodulation system, illustrating an example arrangement or placement of a plurality of electrodes.
Figure 5B:
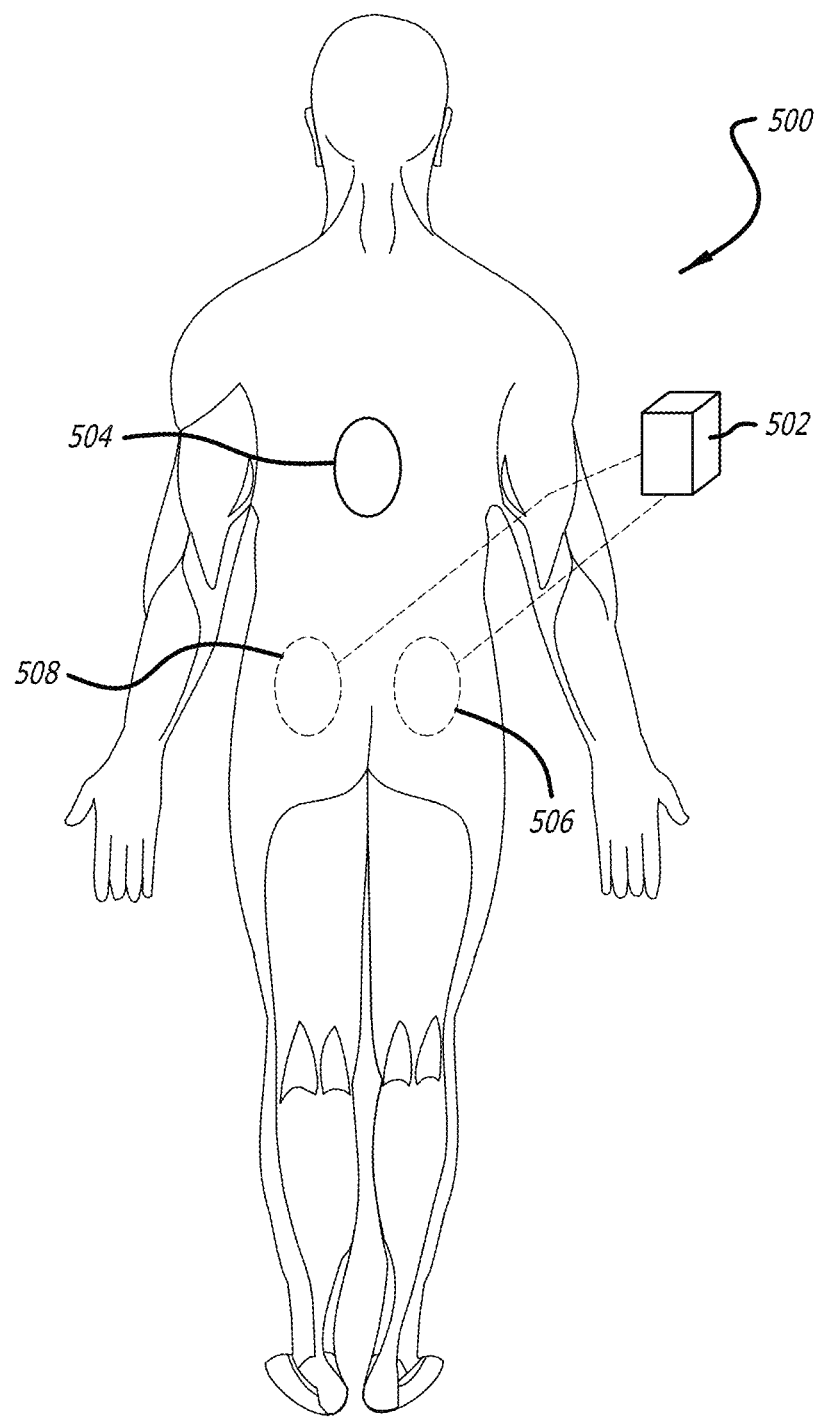

FIGS. 5A and 5B are diagrammatic views of an example neuromodulation system 500, illustrating an example arrangement or placement of a plurality of electrodes. In this example embodiment, neuromodulation system 500 includes trancutaneous electrical stimulator 502 which is operatively connected to at least one electrode or active electrode 504, first ground electrode 506 and second ground electrode 508. As best shown in FIG. 5B, in this example arrangement, active electrode 504 is disposed on the user's trunk. Such a configuration enables the neuromodulation system to deliver symmetrical activation.

Figure 6:
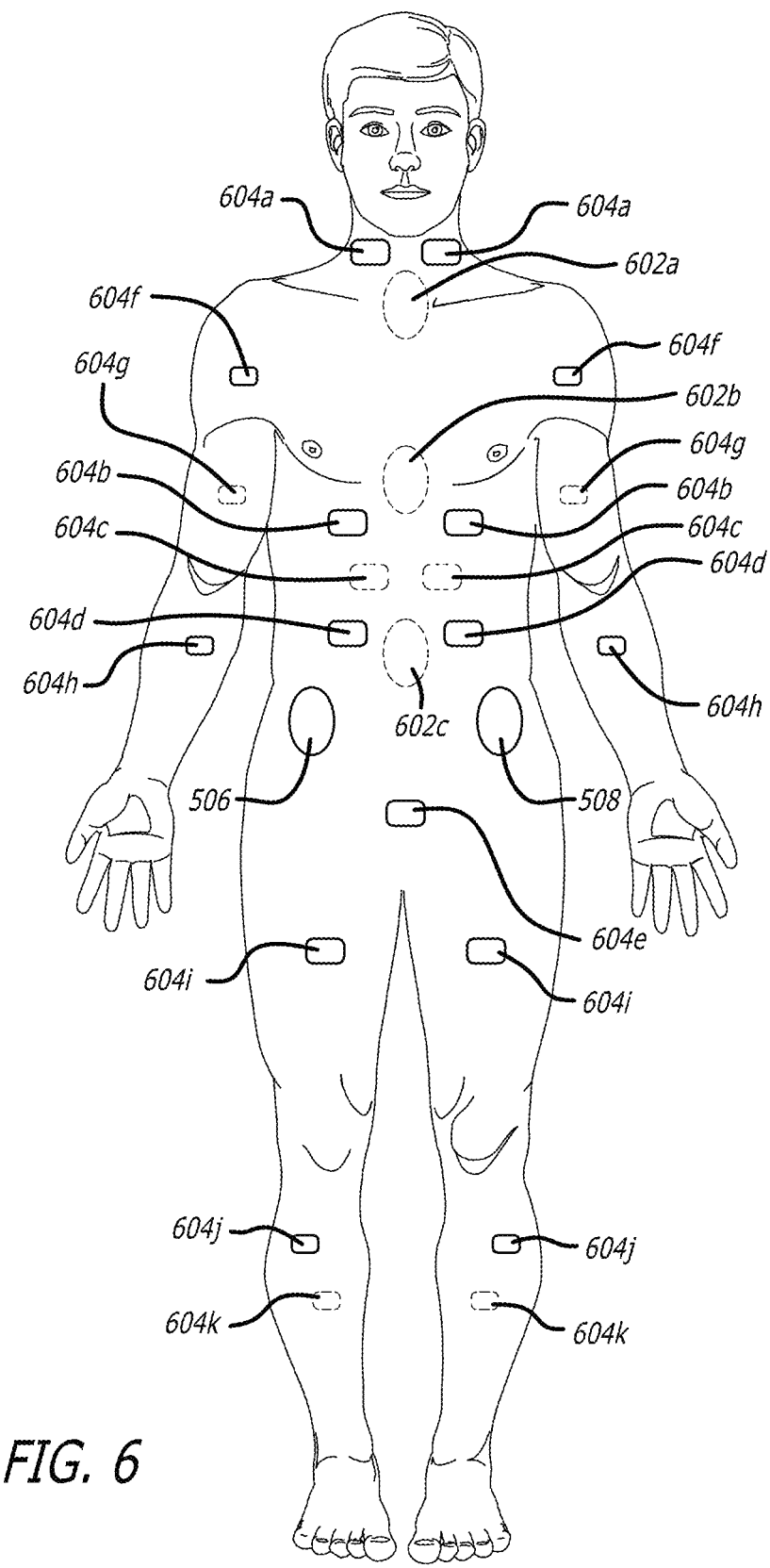
FIG. 6 is a diagrammatic view of alternative arrangements of different types of electrodes.

FIG. 6 is a diagrammatic view of alternative arrangements of different types of electrodes.

An active electrode may be placed in any suitable location. For example, as shown in FIG. 6, an active electrode may be placed overlying the user's neck, as shown by 602a, overlying the user's trunk, as shown by 602b, overlying the user's lower back, as shown by 602c, and/or overlying the base of a skull (i.e., the brainstem) (not shown).

As illustrated in FIG. 6, superficial electrodes may be positioned in a plurality of different locations. For example, superficial electrodes 604a are positioned overlying muscles of the neck or throat. Superficial electrodes 604b may be positioned overlying muscles of the diaphragm. Superficial electrodes 604c may be positioned overlying the kidney region. Superficial electrodes 604d may be positioned overlying the stomach region. Superficial electrode 604e may be positioned overlying the pubic region. Superficial electrodes 604f may be positioned overlying the shoulder or upper arm. Superficial electrodes 604g may be positioned overlying the biceps or upper arm. Superficial electrodes 604h may be positioned overlying the forearm. Superficial electrodes 604i may be positioned overlying the upper leg or thigh. Superficial electrodes 604j may be positioned overlying the lower leg or calf. Superficial electrodes 604k may be positioned overlying the lower leg or shin. Superficial electrodes 604a may be positioned overlying muscles of the neck or throat.

In one example embodiment, at least one electrode is configured to be implanted in a user. In this example, system 100 includes an electrical stimulator which wirelessly communicates with the at least one implanted electrode. In one example embodiment, the transcutaneous electrical stimulator causes the implanted electrode to deliver the generated first signal and the generated second signal. In some embodiments, the at least one implanted electrode is configured to record data and wirelessly transmit the recorded data to the electrical stimulator. In some embodiments, where the at least one electrode is implanted, the at least one electrode is configured to deliver the first generated signal and not the second generated signal. That is, in this example, the second generated signal is not needed.

In some embodiments, system 100 is configured to wirelessly communicate with adjunctive or ancillary equipment such as the footwear described in U.S. Pat. No. 7,726,206 which is hereby incorporated by reference in its entirety. The adjunctive or ancillary equipment may include at least one of a drug pump, drug delivery systems, physical therapy or skeletal support systems.

Figure 7:
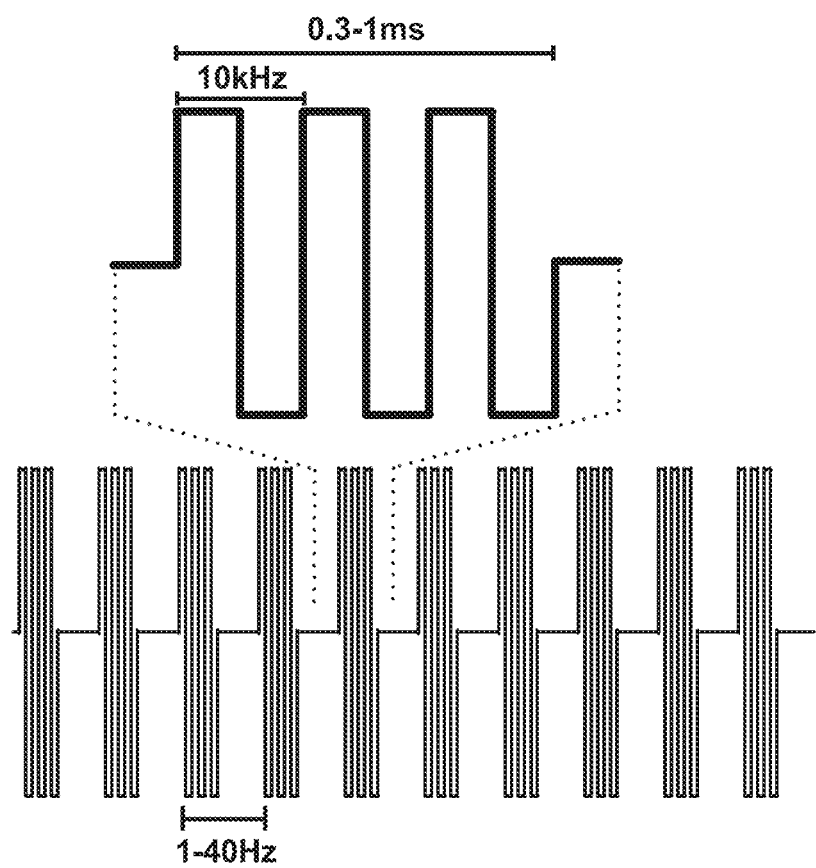
FIG. 7 is a diagrammatic view of an example signal which is delivered to a mammal.

As discussed above, in some embodiments, the neuromodulation system generates and delivers a first signal and a second signal. FIG. 7 illustrates one example of a signal which is delivered by the modulation system via at least one electrode. In this example, the signal is a 1-40 Hz bipolar rectangular stimulus with a duration between 0.3 and 1.0 ms, filled with a carrier frequency of 5-10 kHz. The signal illustrated in FIG. 7 may result in less skin impedance, and more comfortable and relatively painless treatment which yields greater compliance and better outcomes.

In one example embodiment, the neuromodulation system includes a transistor (e.g., a push-pull transistor) which is configured to set the voltage of the delivered signal. The signal may be coupled through a transformer to patient channels or electrodes. Using switches, the channels or electrodes are activated and the signal is applied. The neuromodulation system may include an opto-coupler current detection circuit. The signal may vary in duration, pulse frequency, pulse train duration and number of pulse trains.

In one example embodiment, for locomotion, the delivered signal is 30-40 Hz at 85-100 mA with an overlapping filling frequency of 10 kHZ.

The generated second or overlapping signal may have a frequency between 5 kHz and 10 kHz. In some embodiments, the generated second signal is adjustable between 5 kHz and 10 kHz.

In one example embodiment, the neuromodulation system is configured to deliver a bipolar rectangular stimulus with a pulse duration of 0.5 ms, filled with a carrier frequency of 10 kHz.

In one example embodiment, the neuromodulation system is configured to deliver biphasic stimuli filled with a carrier frequency of 10 kHz. In this example, the biphasic stimuli filled with a carrier frequency of 10 kHz may suppress the sensitivity of pain receptors of the subject. In another example embodiment, the neuromodulation system is configured to deliver biphasic stimuli filled with a carrier frequency of 5-10 kHz.

In some embodiments, the neuromodulation system sums the first generated signal and the second generated signal to generate a signal that is delivered to the electrode. In some embodiments, the neuromodulation system includes a frequency mixer configured to add or sum the first generated signal and the second generated signal.

In some embodiments, the neuromodulation system is configured to send different frequencies to two or more different electrodes which may be spatially separated on the surface of a patient's body.

In some embodiments, the neuromodulation system synchronizes the phasing between the first generated signal and the second generated signal at one point in time. In some embodiments, where the higher frequency is an integer multiple of the lower frequency, the neuromodulation system repeatedly synchronizes the phasing between the first generated signal and the second generated signal.

In one example embodiment, electrical stimulation is delivered at 1-100 Hz and at 30-200 mA.

In one example embodiment, electrical stimulation is delivered at 5-40 Hz and at one of 0-300 mA, 1-120 mA, 20-100 mA and 85-100 mA.

In one example embodiment, the frequency of the delivered signal is adjustable. In some embodiments, the frequency of the first generated signal is adjustable from 0.0-40 Hz.

In some embodiments, the pulse duration of the delivered signal is adjustable. In some embodiments, the pulse duration of at least one of the generated signals is adjustable from 0.5-3.0 ms.

In some embodiments, the amount of amplitude of the delivered signal is adjustable. In some embodiments, the amplitude is adjustable from 0-300 mA.

In some embodiments, the stimulation is continuous. In some embodiments, the stimulation is intermittent.

In some embodiments, the system enables ongoing identification of the optimal stimulation pattern, and allows for adjustment of the stimulating pattern by: (a) auto regulation; (b) direct manual control; or (c) indirect control though wireless technology.

In some embodiments, the neuromodulation system is configured to adjust stimulation and control parameters of the stimulator to levels that are safe and efficacious using parameters chosen to target specific neural components, or end organs and customized to each patient based on response to evaluation and testing.

In some embodiments, the system targets specific components of the nervous system with a desired predetermined stimulation parameter or series of stimulation parameters. In one example, in the case of locomotion, a monopolar electrode is placed over the paravertebral spaces of the thoracic vertebrae of T11-T12, with a reference electrode placed over the abdomen; the system is programmed to deliver 5-40 Hz signal at 85-100 mA with an overlapping high frequency pulse of 10 kHz.

In some embodiments, the neuromodulation system includes at least one sensor. In one example embodiment, the neuromodulation system determines stimulation parameters based on physiological data collected by the at least one sensor.

The at least one sensor may include at least one of an electromyography ("EMG") sensor, a joint angle (or flex) sensor, an accelerometer, a gyroscope sensor, a flow sensor, a pressure sensor, a load sensor, a surface EMG electrode, a foot force plate sensor, an in-shoe sensor, an accelerator, a motion capture system, and a gyroscope sensor attached to or positioned adjacent the body of the subject.

The stimulation parameters may identify a waveform shape, amplitude, frequency, and relative phasing of one or more electrical pulses delivered to one or more pairs of the plurality of electrodes.

The at least one sensor may be connected to the neuromodulation system in any suitable way. For example, the at least one sensor may be connected via wires or wirelessly.

In some embodiments, the neuromodulation system includes at least one recording electrode. The neuromodulation system may be configured to receive and record electrical signals received from the at least one recording electrode. The at least one recording electrode may be positioned on an electrode array. The electrode array may be considered a first electrode array, and the system may include a second electrode array. The at least one recording electrode may be positioned on at least one of the first electrode array and the second electrode array. In some embodiments, the neuromodulation system includes a recording subsystem which is configured to record signals from the at least one recording electrode. The recording subsystem may include amplifiers which may be implemented as low noise amplifiers with programmable gain.

In some embodiments, the neuromodulation system includes a plurality of muscle electrodes which cause muscle to move (e.g., contract) to augment the improved neurological function provided by the complex stimulation patterns alone. The neuromodulation system may deliver electrical stimulation to the plurality of muscle electrodes.

In some embodiments, the neuromodulation system includes a stimulator device operatively connected to the electrodes. The stimulator device may include a casing which is configured to house a signal generator and a control module. The signal generator may be configured to signal generate the signals discussed herein. The control module may be configured to control the signal generator. The casing may be made of molded plastic and may be made compact and portable for single patient use.

The neuromodulation system may be configured to determine a set of stimulation parameters by performing a machine learning method based on signals received from a sensor. In one example, the machine learning method implements a Gaussian Process Optimization or a Dueling Bandit machine learning algorithm or process.

In one example embodiment, the neuromodulation system includes a plurality of electrodes. In this example, the neuromodulation system delivers stimulation or generated signals via a selected one or more of the electrodes.

In some embodiments, the neuromodulation system may be configured with at least one of the following properties or features: (a) a form factor enabling the neurostimulator device to be worn; (b) a power generator with rechargeable battery; (c) a secondary back up battery; (d) electronic and/or mechanical components encapsulated in a package made from one or more synthetic polymer materials; (d) programmable and autoregulatory; (e) ability to record field potentials; (f) ability to operate independently, or in a coordinated manner with other implanted or external devices; and (g) ability to send, store, and receive data via wireless technology.

In some embodiments, the system is capable of open and closed loop functionality, with the ability to generate and record field potentials, evoked potentials and/or modulate membrane potentials of cells and neuronal circuits.

In some embodiments, the stimulator device includes a rechargeable battery or AC current. In some embodiments, the stimulator device includes a dual power source (e.g., back up battery). In some embodiments, the system includes a power generator with a rechargeable battery.

In some embodiments, the non-invasive neurostimulator or neuromodulation devices may be used to deliver therapy to patients to treat a variety of symptoms or conditions such as post traumatic pain, chronic pain, neuropathy, neuralgia, epilepsy, spasm, and tremor associated with and without Parkinson's disease.

Unless defined otherwise, technical and scientific terms used herein have the same meaning as commonly understood by one of ordinary skill in the art to which this disclosure belongs.

The term "motor complete" when used with respect to a spinal cord injury indicates that there is no motor function below the lesion, (e.g., no movement can be voluntarily induced in muscles innervated by spinal segments below the spinal lesion.

The term "monopolar stimulation" refers to stimulation between a local electrode and a common distant return electrode.

The term "autonomic function" refers to functions controlled by the nervous system that are controlled largely below the level of consciousness, and typically involve visceral functions. Illustrative autonomic functions include, but are not limited to control of bowel, bladder, and body temperature.

The term "sexual function" refers to the ability to sustain a penile erection, have an orgasm (male or female), generate viable sperm, and/or undergo an observable physiological change associated with sexual arousal.

The term "cognitive function" refers to awareness of one's surrounding environment and the ability to function effectively, behaviorally, and mentally in a given environment.

In some embodiments, transcutaneous electrical stimulation (tESCS) of the spinal cord can induce activation locomotor circuitry in a mammal (e.g., in a human or a non-human mammal). Further, tECS of the spinal cord can induce activation voluntary locomotor circuitry in a mammal (e.g., in a human or a non-human mammal).

Also, continuous tESCS at 5-40 Hz applied paraspinally over T11-T12 vertebrae at 40-70 mA can induce involuntary locomotor like stepping movements in subjects with their legs in a gravity-independent position. In other embodiments, continuous tESCS at 5-40 Hz applied paraspinally over T11-T12 vertebrae at 40-70 mA can induce voluntary locomotor like stepping movements in subjects with their legs in a gravity-independent position. An increase of frequency of tESCS from 5 to 30 Hz results in augmentation of the amplitude of evoked stepping movements. In chronic spinal cats (3 weeks after spinal cord transection at Th8) tESCS at L5 (a frequency of 5 Hz and intensity ranged from 3 to 10 mA) evoked EMG stepping pattern in hindlimb muscles in all (N=4) of tested animals, while locomotor-like movements produced by tESCS were not weight-bearing.

By non-limiting example, transcutaneous electrical stimulation can be applied to facilitate restoration of voluntary movement, locomotion, and other neurologic function in subjects suffering with spinal cord injury, as well as other neurological injury and illness. Successful application can provide a device for widespread use in rehabilitation of neurologic injury and disease.

The neuromodulation system may facilitate or induce voluntary movement in a mammalian subject (e.g., a human) having a spinal cord injury, brain injury, or other neurological disease or injury. In certain embodiments, the neuromodulation system is configured to stimulate the spinal cord of the subject using a surface electrode where the stimulation modulates the electrophysiological properties of selected spinal circuits in the subject so they can be activated by proprioceptive derived information and/or input from supraspinal. In some embodiments, stimulation may be accompanied by physical training (e.g., movement) of the region where the sensory-motor circuits of the spinal cord are located. In other embodiments, the stimulation includes a biphasic signal and an overlapping high frequency pulse.

In some embodiments, the neuromodulation system is configured to stimulate the spinal cord with electrodes that modulate the proprioceptive and supraspinal information which controls the lower limbs during standing and/or stepping and/or the upper limbs during reaching and/or grasping conditions. In some embodiments, proprioceptive and cutaneous sensory information can guide the activation of the muscles in a coordinated manner and in a manner that accommodates the external conditions, e.g., the amount of loading, speed, and direction of stepping or whether the load is equally dispersed on the two lower limbs, indicating a standing event, alternating loading indicating stepping, or sensing postural adjustments signifying the intent to reach and grasp.

Unlike approaches that involve specific stimulation of motor neurons to directly induce a movement, the neuromodulation system described herein enables spinal circuitry to control the movements. More specifically, the neuromodulation system described herein can exploit the spinal circuitry and its ability to interpret proprioceptive information and to respond to that proprioceptive information in a functional way. In some embodiments, this is in contrast to other approaches where the actual movement is induced/controlled by direct stimulation (e.g., of particular motor neurons).

In one example embodiment, a subject is fitted with one or more surface electrodes that afford selective stimulation and control capability to select sites, mode(s), and intensity of stimulation via electrodes placed superficially over, for example, the lumbosacral spinal cord and/or cervical spinal cord to facilitate movement of the arms and/or legs of individuals with a severely debilitating neuromotor disorder. The subject is provided the generator control unit and is fitted with an electrode(s) and then tested to identify the most effective subject specific stimulation paradigms for facilitation of movement (e.g., stepping and standing and/or arm and/or hand movement). Using these stimulation paradigms, the subject practices standing and stepping, reaching or grabbing, and/or breathing and speech therapy in an interactive rehabilitation program while being subject to spinal stimulation as described herein including a biphasic signal and an overlapping high frequency pulse.

Depending on the site/type of injury and the locomotor activity it is desired to facilitate, particular spinal stimulation protocols include, but are not limited to, specific stimulation sites along the lumbosacral, thoracic, and/or cervical spinal cord; specific combinations of stimulation sites along the lumbosacral, thoracic, and/or cervical spinal cord and/or brainstem; specific stimulation amplitudes; specific stimulation polarities (e.g., monopolar and bipolar stimulation modalities); specific stimulation frequencies; and/or specific stimulation pulse widths.

In some embodiments, the neuromodulation system is designed so that the patient can use and control it in the home environment In some embodiments, the approach is not to electrically induce a walking pattern or standing pattern of activation, but to enable/facilitate it so that when the subject manipulates their body position, the spinal cord can receive proprioceptive information from the legs (or arms) that can be readily recognized by the spinal circuitry. Then, the spinal cord knows whether to step or to stand or to do nothing. In other words, this enables the subject to begin stepping or to stand or to reach and grasp when they choose after the stimulation pattern has been initiated.

Moreover, the neuromodulation system described herein is effective in a spinal cord injured subject that is clinically classified as motor complete; that is, there is no motor function below the lesion. In some embodiments, the specific combination of electrode(s) activated/stimulated and/or the desired stimulation of any one or more electrodes and/or the stimulation amplitude (strength) can be varied in real time, e.g., by the subject. Closed loop control can be embedded in the process by engaging the spinal circuitry as a source of feedback and feed-forward processing of proprioceptive input and by voluntarily imposing fine tuning modulation in stimulation parameters based on visual, and/or kinetic, and/or kinematic input from selected body segments.

In some embodiments, the neuromodulation system is designed so that a subject with no voluntary movement capacity can execute effective voluntary movements such as, but not limited to standing and/or stepping and/or reaching and/or grasping. In addition, the approach described herein can play an important role in facilitating recovery of individuals with severe although not complete injuries.

In some embodiments, the neuromodulation system may provide some basic postural, locomotor and reaching and grasping patterns to a user. In some embodiments, the neuromodulation system may provide a building block for future recovery strategies. In some embodiments, a strategy of combining effective transcutaneous stimulation of the appropriate spinal circuits with physical rehabilitation and pharmacological intervention can provide practical therapies for complete SCI human patients. Such an approach may be enough to enable weight bearing standing, stepping and/or reaching or grasping or other movements. Such capability can give SCI patients with complete paralysis or other neuromotor dysfunctions the ability to participate in exercise, which is known to be highly beneficial for their physical and mental health. In some embodiments, the neuromodulation system may enable movement with the aid of assistive walkers. While far from complete recovery of all movements, even simple standing and short duration walking would increase these patients' autonomy and quality of life. The neuromodulation system described herein (e.g., transcutaneous electrical stimulation) can provide for a direct brain-to-spinal cord interface that could enable more lengthy and finer control of movements.

While the neuromodulation systems described herein are discussed with reference to complete spinal injury, it will be recognized that they can apply to subjects with partial spinal injury, subjects with brain injuries (e.g., ischemia, traumatic brain injury, stroke, and the like), and/or subjects with neurodegenerative diseases (e.g., Parkinson's disease, Alzheimer's disease, Huntington's disease, dystonia, amyotrophic lateral sclerosis (ALS), primary lateral sclerosis (PLS), cerebral palsy, and the like).

In some embodiments, the neuromodulation system may be used in conjunction with physical training (e.g., rigorously monitored (robotic) physical training) and optionally in combination with pharmacological techniques or other drug delivery. The neuromodulation system enables the spinal cord circuitry to utilize sensory input as well as newly established functional connections from the brain to circuits below the spinal lesion as a source of control signals. The approach is thus designed to enable and facilitate the natural sensory input as well as supraspinal connections to the spinal cord in order to control movements, rather than induce the spinal cord to directly induce the movement. That is, the neuromodulation system facilitates and enhances the intrinsic neural control mechanisms of the spinal cord that exist post-SCI, rather than replace or ignore them.

Processing of Sensory Input by the Lumbosacral Spinal Cord: Using Afferents as Source of Control In some embodiments, the neuromodulation exploits spinal control of locomotor activity. For example, the human spinal cord may receive sensory input associated with a movement such as stepping, and this sensory information can be used to modulate the motor output to accommodate the appropriate speed of stepping and level of load that is imposed on lower limbs. Moreover, the human lumbosacral spinal cord has central-pattern-generation-like properties. Thus, oscillations of the lower limbs can be induced simply by vibrating the vastus lateralis muscle of the lower limb, by transcutaneous stimulation, and by stretching the hip. The neuromodulation system exploits the fact that the human spinal cord, in complete or incomplete SCI subjects, can receive and interpret proprioceptive and somatosensory information that can be used to control the patterns of neuromuscular activity among the motor pools necessary to generate particular movements (e.g., standing, stepping, reaching, grasping, and the like). The neuromodulation system described herein facilitates and adapts the operation of the existing spinal circuitry that generates, for example, cyclic step-like movements via a combined approach of transcutaneous stimulation, physical training, and, optionally, pharmacology.

Facilitating Stepping and Standing in Humans Following a Clinically Complete Lesion Locomotion in mammals is attributed to intrinsic oscillating spinal neural networks capable of central pattern generation interacting with sensory information. These networks play critical roles in generating the timing of the complex postural and rhythmic motor patterns executed by motor neurons.

As indicated above, the neuromodulation system described herein can involve stimulation of one or more regions of the spinal cord in combination with locomotory activities. Spinal stimulation in combination with locomotor activity results in the modulation of the electrophysiological properties of spinal circuits in the subject so they are activated by Proprioceptive information derived from the region of the subject where locomotor activity is to be facilitated. Further, spinal stimulation in combination with pharmacological agents and locomotor activity results in the modulation of the electrophysiological properties of spinal circuits in the subject so they are activated by proprioceptive information derived from the region of the subject where locomotor activity is to be facilitated.

Locomotor activity of the region of interest can be accomplished by any of a number of methods known, for example, to physical therapists. By way of illustration, individuals after severe SCI can generate standing and stepping patterns when provided with body weight support on a treadmill and manual assistance. During both stand and step training of human subjects with SCI, the subjects can be placed on a treadmill in an upright position and suspended in a harness at the maximum load at which knee buckling and trunk collapse can be avoided. Trainers positioned, for example, behind the subject and at each leg assist as needed in maintaining proper limb kinematics and kinetics appropriate for each specific task. During bilateral standing, both legs can be loaded simultaneously and extension can be the predominant muscular activation pattern, although co-activation of flexors can also occur. Additionally, or alternatively, during stepping the legs are loaded in an alternating pattern and extensor and flexor activation patterns within each limb also alternated as the legs moved from stance through swing. Afferent input related to loading and stepping rate can influence these patterns, and training has been shown to improve these patterns and function in clinically complete SCI subjects.

Transcutaneous Stimulation of the Lumbosacral Spinal Cord

As indicated above, without being bound by a particular theory, it is believed that transcutaneous stimulation (e.g., over the thoracic spinal cord) in combination with physical training can facilitate recovery of stepping and standing in human subjects following a complete SCI.

Spinal cord electrical stimulation has been successfully used in humans for suppression of pain and spasticity. Recent efforts to optimize stimulation parameters have led to a number of research studies focusing on the benefits of transcutaneous spinal cord stimulation. The location of the electrode and its stimulation parameters can be important in defining the motor response. Use of surface electrode(s), as described herein, can facilitate selection or alteration of particular stimulation sites as well as the application of a wide variety of stimulation parameters.

The following non-limiting examples are offered for illustrative purposes.

Example 1

Transcutaneous Electrical Stimulation of the Spinal Cord: A Noninvasive Tool for the Activation of Stepping Pattern Generators in Humans A noninvasive method for activating the SN by means of transcutaneous electrical spinal cord stimulation (tESCS) is demonstrated in this Example. The method is based on our research that showed that a single dermal electric stimulus applied in the region of the T11-T12 vertebrae caused monosynaptic reflexes in the proximal and distal leg muscles in healthy subjects and in patients with clinically complete (ASIA A) spinal cord injury. Taking into consideration that eESCS affects the SN through mono and polysynaptic reflexes, we suggested that noninvasive tESCS can be an effective way to neuromodulate the SN.

Experiment

We examined six healthy adult male subjects (students and staff of the Velikie Luki State Academy of Physical Education and Sports). They had given their informed written consent to participate in the experiment. The experiment was approved by the Ethics Committee of the academy and met the requirements of the Helsinki Declaration.

The subjects lay on a couch on their left side, with their feet placed on separate boards that were attached to a hook in the ceiling of the experimental room with ropes, like swings. The right (upper) leg was supported directly in the region of the shank. The left (lower) leg was placed in a rotating frame attached to a horizontal board. Under these conditions, the subjects could move their legs through maximum amplitude: According to the instructions, the subjects lay quietly and neither counteracted nor facilitated the movements caused by electrical stimulation of the spinal cord.

The tESCS was performed using a KULON stimulator (St. Petersburg State University of Aerospace Instrumentation, St. Petersburg, Russia). The stimulation was administered using a 2.5 cm round electrode (Lead-Lok, Sandpoint, United States) placed midline on the skin between the spinous processes of T11 and T12 as a cathode and two 5.0×cm rectangular plates made of conductive plastic (Ambu, Ballerup, Germany) placed symmetrically on the skin over the iliac crests as anodes. The step-like movements were evoked by a bipolar rectangular stimulus with a duration of 0.5 ms, filled with a carrier frequency of 10 kHz; the intensity of stimulation ranged from 30 to 100 mA. The stimulation frequencies were 1, 5, 10, 20, 30, and 40 Hz; the duration of exposure ranged from 10 to 30 s. During the high-frequency stimulation within each stimulus, tESCS did not cause pain even when the amplitude was increased to 100 mA or more; allowing us to study in detail the dependence of the elicited movements on the amplitude and frequency of the stimulus.

The EMGs of the muscles of both legs (m. rectus femoris, m. biceps femoris, m. tibialis anterior, and m. gastrocnemius) were recorded by means of bipolar surface electrodes. EMG signals were recorded using an ME 6000 16-channel telemetric electroneuromyograph (Mega Win, Finland). Flexion-extension movements in the knee joints were recorded using a goniometer.

The Qualisy video system (Sweden) was used to record the kinematic parameters of leg movements. Light-reflecting markers were attached to the pivot points of the body, which coincided with the rotational axis in the shoulder, hip, knee, and ankle joints. The angular movements in the hip joint were calculated from the location of markers on the lateral epicondyle of the humorous, trochanter, and lateral epicondyle of the femur. The markers that were attached to the trochanter, lateral epicondyle of the femur, and lateral ankle were used to describe the movements in the knee joint. The movements in the ankle joint were estimated by means of the markers located on the lateral epicondyle of the femur, lateral ankle, and the big toe. The reconstruction of movements in one whole step cycle was performed by means of special software. In order to record the movements of the foot tip, the marker was fixed on the big toe of the right foot.

The recording of EMG was synchronized with the recording of stepping kinematical parameters. The average cycle duration and the amplitudes of angular movements were calculated from 10-12 cycles. The duration of a step cycle was calculated on the basis of the interval between two maximum values of angular movements in the hip, knee, and ankle joints. The phase shift between the hip and knee joints was calculated from the interval between the maximum values of angular movements in these joints.

The statistical treatment of the data was performed using a standard software package.

Results

Transcutaneous electrical spinal cord stimulation with a frequency of 5-40 Hz elicited involuntary leg movements in five out of six subjects. The threshold intensity of the stimulus that induced involuntary movements was 50-60 mA and was dependent on the frequency of stimulation. The tESCS at a frequency of 1 Hz caused reflex responses in the leg muscles with a threshold of 70-80 mA (FIG. 8a).

Figure 8:
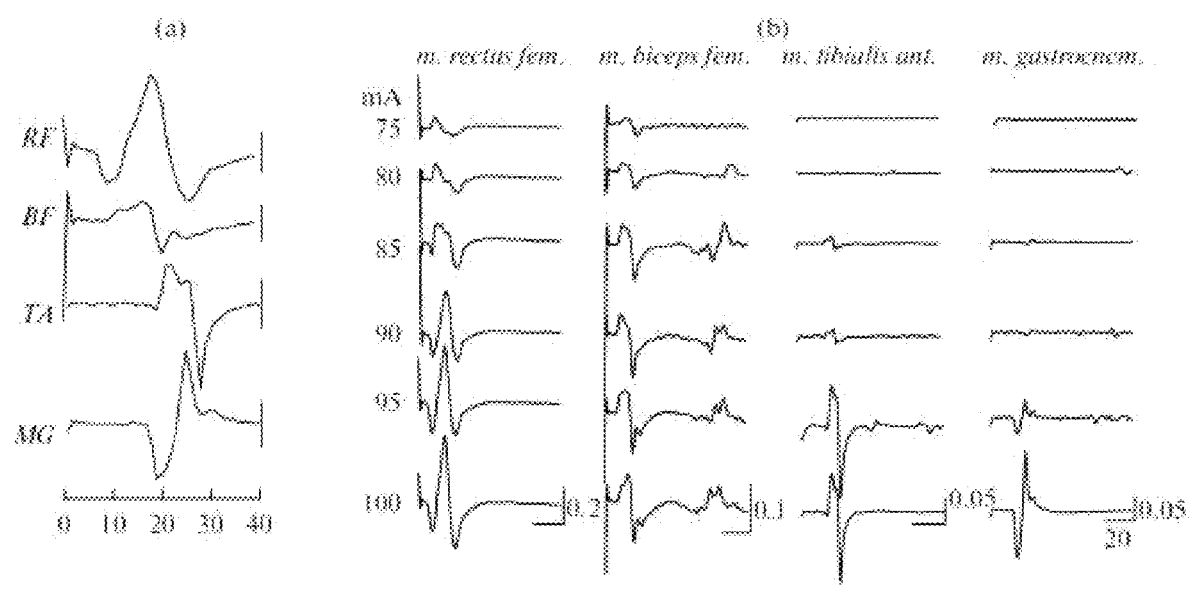
FIG. 8, panels a and b, show motor responses in the muscles of the right leg to the tESCS with a frequency of 1 Hz and an amplitude of 75-100 mA (showed at the left of the recordings). The responses in the m. rectus femoris and m. biceps femoris (RF and BF, respectively), as well as in the m. tibialis anterior and m. gastrocnemius (TA and MG, respectively) are shown. At the right bottom of the lower recording, there are marks of time in ms, the same for all the muscles, and marks of the amplitude in mV.

Original records of EMG responses in the muscles of the right leg to the tESCS at a frequency of 1 Hz and intensity of 75-100 mA are shown in FIG. 8. Increasing stimulus intensity resulted in an increase in the amplitude of responses. First, the hip muscles (m. rectus femoris and m. biceps femoris) were involved in the motor response; then, the shank muscles (m. tibialis anterior and m. gastrocnemius) were involved (FIG. 8b). The response to each stimulus is composed of the early monosynaptic responses (the same is shown in Courtine, Harkema, Dy, Gerasimenko, and Dyhre-Poulsen, supra) with a latency period of about 12-15 ms. Increasing stimulus intensity evoked responses in the biceps femoris muscle (flexor) with a latent period of a few tens of milliseconds, which were, apparently, polysynaptic. Thus, tESCS with a low frequency (1 Hz) elicited reflex responses in the leg muscles that contained mono and polysynaptic components.

Figure 9A:
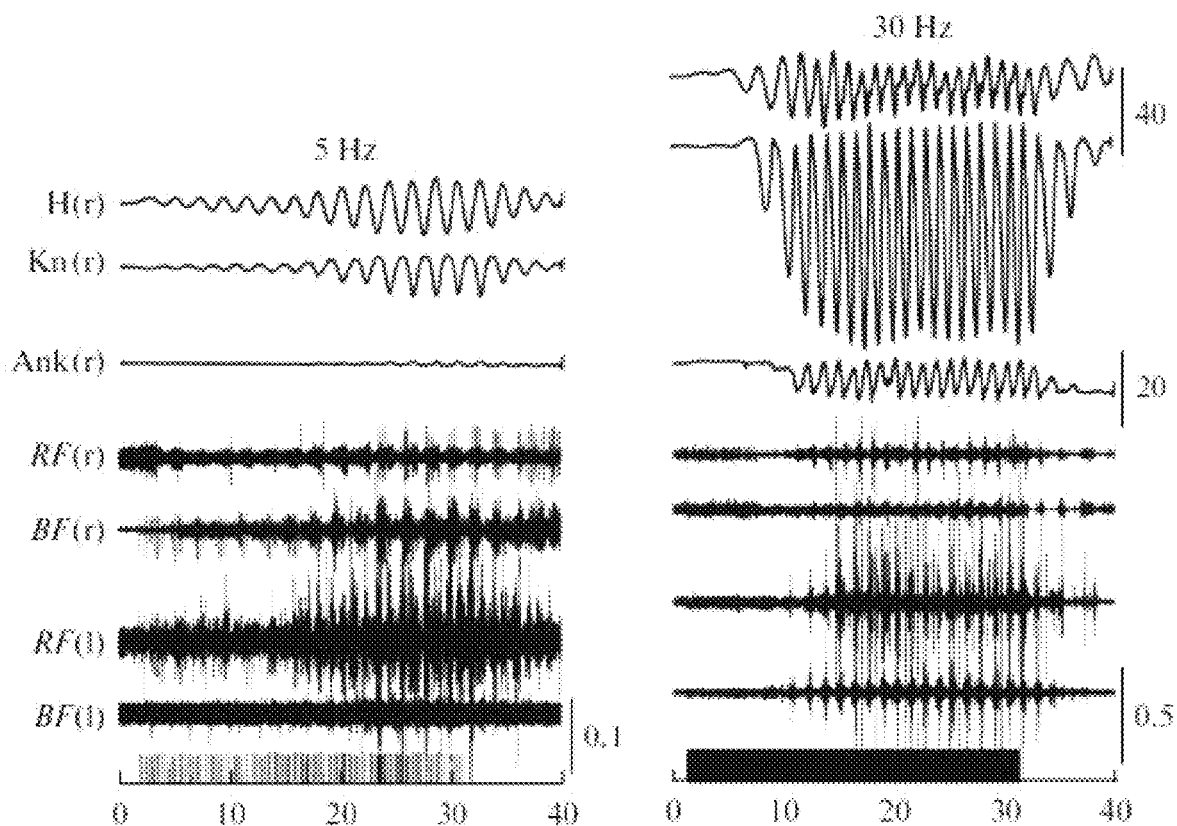
FIGS. 9A and 9B show electrical activity of the leg muscles and movements in the leg joints evoked by tESCS with frequencies of 5 and 30 Hz.
Figure 9B:
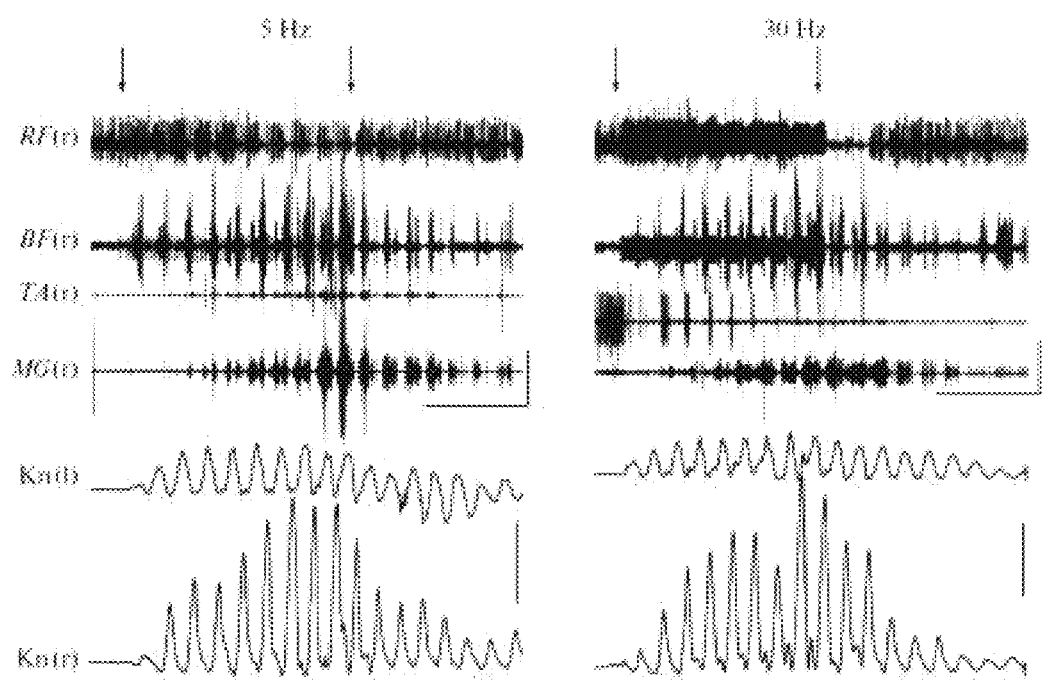

Transcutaneous electrical spinal cord stimulation at frequencies in the entire range from 5 to 40 Hz caused step-like movements in five subjects (FIG. 9). There was some variability in the ability of tESCS to evoke step-like movements at different frequencies of stimulation. In two subjects (R. and S.), step-like movements were evoked by tESCS at all the test frequencies in the range 5-40 Hz; in subjects K and G., they were recorded at frequencies of 5, 10, 20, and 30 Hz; and in subject B, they were recorded at frequencies of 5 and 30 Hz. The latent period of the starting of movements did not depend on the frequency of stimulation and was in the range of 0.2-2.5 s. The amplitude of movements in subjects S, G, and R at the beginning of stimulation gradually increased to the maximum, and after its termination it gradually decreased. In subjects K and V, the movements terminated against the background of ongoing tESCS, the duration of the stepping pattern was approximately 10-20 s. In subjects R and S, the movements continued during the whole period of stimulation and ended 2-4 s after its termination.

Pair wise comparison of the mean amplitudes of the movements of the hip, knee, and ankle joints calculated during the first and the last 15 s of stimulation at each of the frequencies used allowed us to determine the probability of the differences in the amplitudes of the induced movements at the beginning and at the end of the stimulation (see Table 1, below). Two rows of probabilities for subject C, calculated on the bases of two experiments show the different direction of the changes in the amplitudes at the beginning and end of stimulation. In the table, the cases when the amplitude of movements at the end of the stimulation was significantly greater than in the beginning are boldfaced; the cases when the amplitude of movements at the end of the stimulation was significantly lower than in the beginning are italicized. According to the data, the subjects were divided into two groups. In the first group (subjects R and S), step-like movements were evoked by the stimulation at the entire range of the frequencies studied (5-40 Hz), and the amplitude of movements, while growing at the beginning of stimulation, decayed after its termination. In the second group (subjects K and V), the movements were evoked with difficulty and with a limited set of frequencies. These differences could be related both to the individual characteristics of the electrical conductivity of the skin and to characteristics of the spinal connections.

Figure 10:
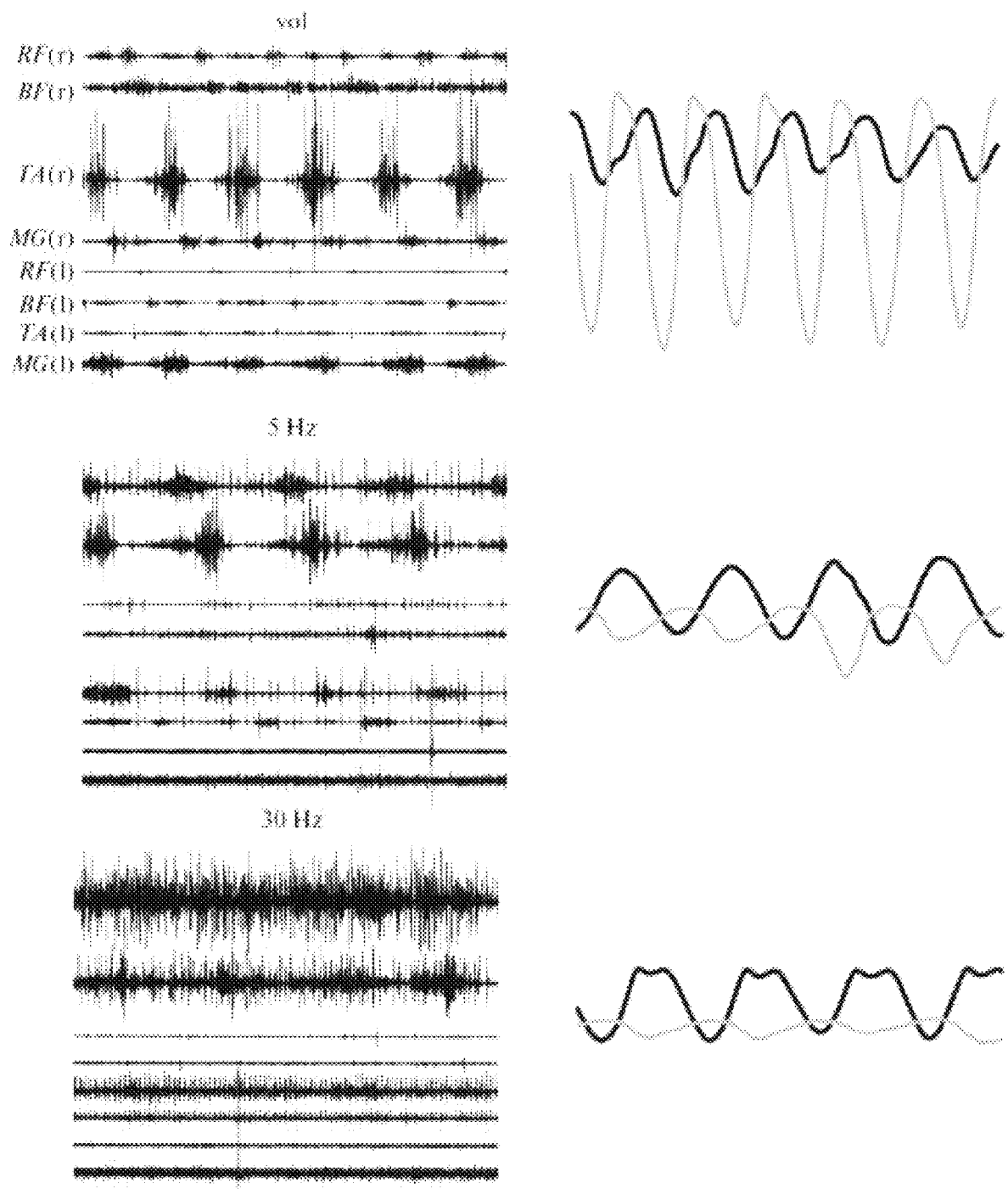
FIG. 10 EMGs (left) and trajectories of reflective markers attached to the right leg; kinematograms (right) recorded during voluntary stepping movements (vol) and movements caused by tESCS with frequencies of 5 and 30 Hz. The duration of records is 10 s. Black and gray lines show movements in the hip and knee joints, along with calibrations for changes in joint angles respectively. The remaining designations are the same as in FIG. 2.

The involuntary movements of the legs caused by tESCS fully complied with the characteristics of stepping movements (FIG. 10). Like voluntary stepping movements, the involuntary movements caused by tESCS surely contain the alternating contractions of the similar muscles of the left and right legs and the alternation of antagonist muscle activity in the hip and shin (rectus femoris and biceps femoris, gastrocnemius and tibial muscle of the shin). As clearly seen in the curves reflecting the motion of the hip and knee joints, the movements in these joints, both voluntary and evoked by tESCS, occurred with a phase shift (the motion in the knee ahead of the motion in the hip).

The table below shows the probability of similarity of the mean amplitudes of movements, measured in the first and the last 15 s during tESCS. For subject S., two different cases of stimulation are shown.

TABLE 1

| | | The Frequency of Stimulation | | | | |
|---|---|---|---|---|---|---|
| Subject | Joint | 5 Hz | 10 Hz | 20 Hz | 30 Hz | 40 Hz |
| S. (1) | H | 0.08 | 0.16 | 0.20 | 0.05 | 0.1 |
| | Kn | 0.003 | 0.26 | 0.41 | 0.03 | 0.0003 |
| | Ank | 0.08 | 0.07 | 0.18 | 0.20 | 0.07 |
| S. (2) | H | 0.01 | 0.0001 | 0.004 | 0.82 | 0.92 |
| | Kn | 0.04 | 0.0001 | 0.002 | 0.0004 | 0.12 |
| | Ank | 0.002 | 0.0006 | 0.002 | 0.001 | 0.08 |
| R. | H | 0.07 | 0.05 | 0.14 | 0.27 | *0.007* |
| | Kn | 0.0001 | 0.001 | 0.03 | 0.01 | 0.15 |
| | Ank | 0.02 | 0.008 | 0.003 | 0.47 | 0.68 |
| K. | H | 0.99 | | | *0.002* | |
| | Kn | *0.03* | | | *0.008* | |
| | Ank | 0.21 | | | *0.001* | |
| B. | H | *0.03* | 0.16 | 0.27 | 0.68 | |
| | Kn | 0.12 | 0.06 | *0.04* | *0.02* | |
| | Ank | *0.05* | 0.99 | 0.15 | *0.001* | |
| G. | H | *0.004* | 0.16 | 0.21 | 0.16 | |
| | Kn | *0.05* | 0.08 | 0.24 | 0.26 | |
| | Ank | *0.005* | *0.05* | 0.29 | *0.009* | |

Notes:
H, hip joint; Kn, knee joint; Ank, ankle joint.
The cases where p ≤ 0.05 are boldfaced and italicized.

Figure 11:
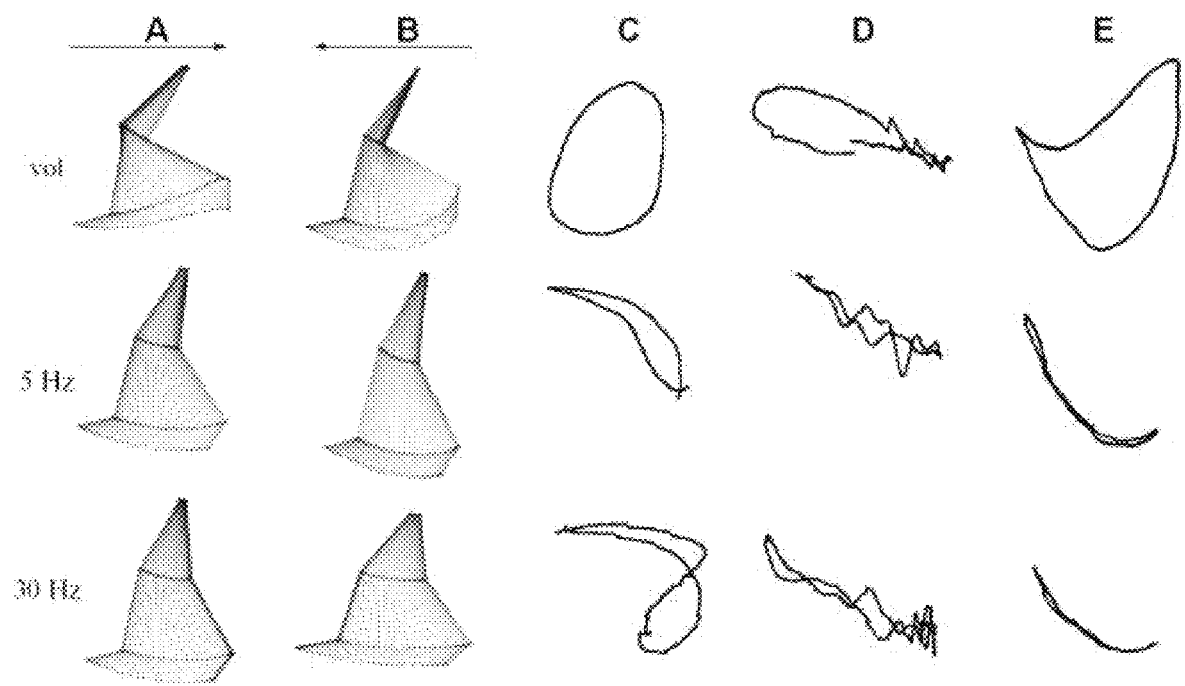
FIG. 11, panels A-E, show interarticular coordination during voluntary stepping movements (vol) and movements caused by tESCS with frequencies of 5 and 30 Hz. Reconstruction of the movements of the right leg during one stepping cycle obtained by processing the cinematograms of the (Panel A) forward and (Panel B) backward movements of legs, respectively; the coordination of movements in the (Panel C) hip and knee joints, (Panel D) knee and ankle joints; and (Panel E) the trajectory of a big toe. Subject R.

Stepping cycles in three joints of the right leg during voluntary stepping movements (FIG. 11a) and movements elicited by tESCS reconstructed based on the kinematic analysis and the trajectory of the tip of the foot (the big toe) are shown in FIG. 11. In step-like movements elicited by tESCS, as in voluntary stepping movements, the phase of carrying the leg forward and the phase of support during the backward leg movements were distinct (FIGS. 11a, 11b). During voluntary movements, the patterns of the knee and ankle joints are more complex than during the elicited movements. The coordination between the joints during the evoked movements is very different from that observed during voluntary movements (FIGS. 11c, 4d). The same is true for the movements of the distal region of the leg, resulting from the interaction of movements in all three joints, and recorded using a marker attached to the big toe (FIG. 11f). The trajectory of the terminal point in voluntary movements looked like an ellipse (FIG. 11f). The trajectory of the terminal point in the movements elicited by tESCS may be considered a confluent ellipse, with the leg moving forward and backward without significant vertical movements.

The frequency of step-like movements did not depend on the frequency of stimulation. The average periods of step-like movements in subjects R, S, K, B, and G were $2.72 \pm 0.14$, $2.39 \pm 0.55$, $2.42 \pm 0.15$, $3.22 \pm 0.85$, and $1.9 \pm 0.09$ s, respectively.

Figure 12:
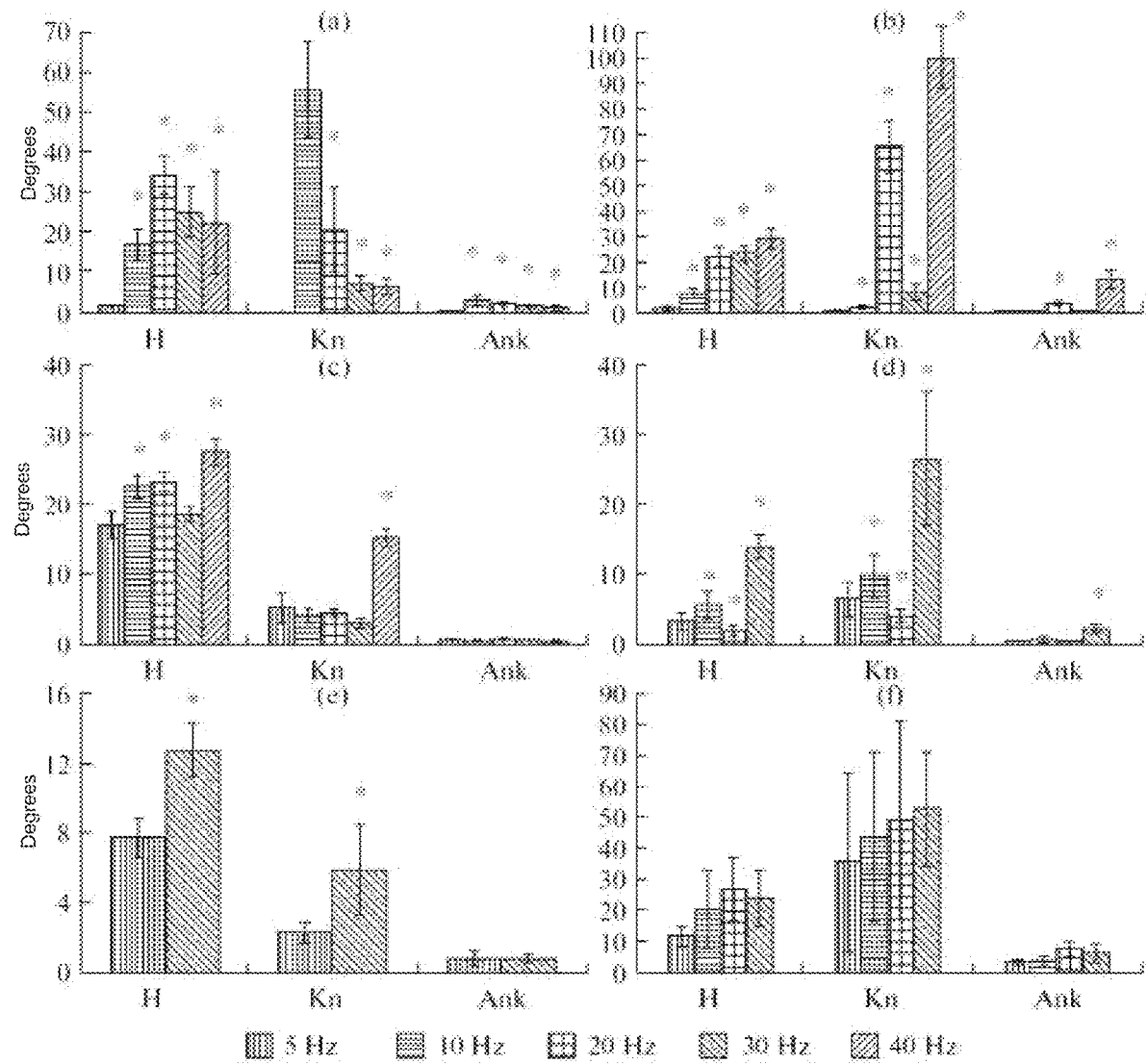
FIG. 12, panels a-f, show the average amplitude of movements in the hip (H), knee (Kn), and ankle (Ank) joints caused by tESCS with a frequency of 5-40 Hz recorded during the first 15 s after the start of stimulation. The ordinate shows angular degrees. (Panels a, b) Subject S, different strategies; (Panel b) subject R; (Panel c) subject B; (Panel d) subject E; (Panel e) subject G; (Panel f) subject K. Error bars, standard deviation. Asterisks, significant differences in amplitude recorded during tESCS with a frequency of 5 Hz, $p \geq 0.05$.

As mentioned above, the pair wise comparison of the mean amplitudes of the movements in the hip, knee, and ankle joints calculated in the first and the last 15 s of stimulation in different subjects, showed that, regardless of the stimulation frequency, the amplitude of movements may either increase or decrease significantly. At the beginning of stimulation, there was a tendency for the amplitude of movements to increase with increasing frequency of stimulation in all subjects for all joints (FIG. 12). However, at the end of stimulation, the amplitude of movements was independent of the stimulation frequency. In all joints, minimum movements were observed at a stimulation frequency of 5 Hz (FIGS. 12b, 12d). As an exception, only in one case, when subject S. was stimulated, the amplitude of movements in the hip joint increased with increasing stimulation frequency and the amplitude of movements in the knee and ankle joints decreased with increasing frequency [FIG. 12; table 1, subject S. (1)]. The trajectory of movement of the big toe of this subject, reflecting the amplitude of the whole leg's movement, is shown in FIG. 12a. In this case, the amplitude of movement of the tip of the foot at stimulation frequencies of 10, 20, 30, and 40 Hz was, respectively, 15.0, 19.9, 15.3, and 16.4 times greater than at 5 Hz. In the case shown in FIG. 12b, it was, respectively, 3.5, 9.4, 11.3, and 80.7 times greater than at 5 Hz. Thus, in this subject, with increasing frequency of stimulation, the amplitude of leg movements did not decrease in any of the cases; it was minimal at a frequency of 5 Hz.

Note that, in the cases shown in FIGS. 12b and 12d, an increase in frequency resulted in a significant increase in the amplitude of movements in the ankle joint. The possibility to control the movements in the ankle joint via the frequency of stimulation was an advantage of tECS, unlike the ankle joint which was not modulated in vibration-induced step-like movements. See Gorodnichev, Machueva, Pivovarova, Semenov, Ivanov, Savokhin, Edgerton, and Gerasimenko, supra.

Discussion

Transcutaneous electrical stimulation of the lumbar enlargement may strengthen the patterns of EMG activity in leg muscles in patients with complete or partial spinal cord lesions during assisted walking movements on a moving treadmill. However, voluntary step-like movements were never successfully evoked by means of transcutaneous stimulation in this category of patients before. It was observed that transcutaneous electrical stimulation applied to the rostral segments of the lumbar enlargement (in the region of the T11-T12 vertebrae) elicited involuntary step-like movements in healthy subjects with their legs suspended in a gravity-neutral position. This phenomenon was observed in five out of the six subjects studied. tESCS did not cause discomfort and was easily tolerated by subjects when biphasic stimuli filled with a carrier frequency of 10 kHz which suppressed the sensitivity of pain receptors were used.

Reflex Nature of the Responses Evoked by tESCS

A single transcutaneous electrical stimulation in the region of the T11-T12 vertebrae causes responses in leg muscles with a latency period corresponding to monosynaptic reflexes. It was assumed that these responses are due to the activation of large-diameter dorsal root afferents. The monosynaptic nature of these responses is confirmed by the fact that vibration of muscle tendons or paired stimulation suppresses the responses. We have previously shown that the responses to the second stimulus were suppressed in rats during epidural stimulation and in healthy humans during paired tESCS with a delay between the stimuli of 50 ms. This refractory period excludes the possibility of direct activation of the motor neurons in the ventral horn or ventral root activation. The monosynaptic nature of the responses was also shown during vibration tests. It is well known that vibration suppresses monosynaptic reflex pathways in homologous muscles. The suppression of responses caused by tESCS in shin muscles during the vibration of the Achilles tendon directly shows the monosynaptic nature of these responses. The similarity of modulations of the classical monosynaptic H-reflex and reflex responses caused by tESCS during walking in healthy subjects and in patients with spinal cord injuries also supports the monosynaptic nature of the responses to transcutaneous stimulation. In both cases, the amplitude of modulation of the reflexes was proportional and phase-dependent on the activation level of each muscle. All of the above data indicate the identity of the H-reflex and reflex responses induced by tESCS.

In the flexor muscles affected by tESCS, polysynaptic reflexes were sometimes recorded in addition to the monosynaptic component (FIG. 8). Earlier, we recorded polysynaptic reflexes in the flexor the intact and spinal animals during the single epidural stimulation. Data suggests that tESCS can activate mono and polysynaptic neuronal networks.

Characteristics of Transcutaneous Stimulation Eliciting Step-Like Movements

The previous experiments showed that the rostral segments of the lumbar spinal cord may play the role of triggers in initiating locomotor movements. In spinal patients and in spinal rats, step-like patterns of EMG activity were evoked by epidural stimulation of the L2 segment. In our experiments, we used transcutaneous electrical stimulation in the region of T11-T12 vertebrae, which corresponds to the cutaneous projection of the L2-L3 segments of the spinal cord. The electromagnetic stimulation of this region in healthy subjects with their legs supported externally can initiate walking movements. Data are consistent with the current concept on the structural and functional organization of the SN with distributed pacemaking and pattern-generating systems, in which the rostral lumbar segments of the spinal cord play the role of a trigger of the locomotor function.

The frequency of stimulation can be an important characteristic of the motor output. It was shown that step-like movements are evoked by stimulation frequencies in the range of 5-40 Hz. The amplitude of step-like movements induced by high-frequency stimulation (30-40 Hz) was usually higher than that of the movements induced by low frequency stimulation (5 Hz), although the duration of the stepping cycle varied slightly. The fact that a wide range of frequencies can effectively induce step-like movements is probably due to the functional state of the intact spinal cord and its pathways. For example, in spinal patients, the effective frequency range for the initiation of step-like movements using epidural stimulation was 30-40 Hz; in decerebrated cats, the frequency of 5 Hz was the most effective to elicit locomotion.

The intensity of transcutaneous electrical stimulation (50-80 mA) that causes step-like movements is approximately 10 times higher than the intensity of the epidural stimulation initiating walking movements in spinal patients. If the dorsal roots are the main target for both types of stimulation, the current may be strong to activate them by transcutaneous electrical stimulation. Thus, we conclude that the location, frequency, and intensity of stimulation can be the factors that determine the activation of the SN by tESCS.

The Origin of the Stepping Rhythm Evoked by tESCS

In most subjects, the involuntary step-like movements in the hip and knee joints were initiated by tESCS with a delay of 2-3 s after the start of stimulation. Typically, the amplitude of movements in the hip and knee joints increased smoothly and gradually with the subsequent involvement of the ankle joint (FIG. 9). A similar character of the initiation of involuntary step-like movements with gradual involvement of different motor pools of the leg muscles was also observed during the vibration of muscles and the epidural spinal cord stimulation. This suggests that transcutaneous electrical stimulation, as well as the epidural stimulation, affects the SN through the activation of the dorsal root afferents entering the spinal cord. In addition to the dorsal roots and dorsal columns, the direct stimulation of the spinal cord may also activate the pyramidal and reticulospinal tracts, ventral roots, motor neurons, dorsal horn, and sympathetic tracts. During the tESCS, the electric current spreads perpendicular to the spinal column with a high density under the paravertebral electrode. This stimulation apparently activates the dorsal roots immersed in the cerebrospinal fluid, but not the spinal cord neurons, which have a much lower conductivity. In some embodiments, tESCS consequently involves in activity the afferents of groups Ia and Ib with the largest diameter and, thus, the lowest threshold, then the afferents of the group II, and the spinal interneurons mediating polysynaptic reflexes. The presence of polysynaptic components in the evoked potentials in the flexor muscles (FIG. 8) confirms that they participate in the SPG. Thus, we can say that tESCS activates different spinal neuronal systems; however, the dorsal roots with their mono and polysynaptic projections to the motor nuclei are the main ones among them. The contribution of mono and polysynaptic components in the formation of the stepping rhythm caused by tESCS is not known.

In our studies, single pulse stimulation resulted in monosynaptic reflexes in the majority of the leg muscles investigated. However, the electromyographic trains evoked by continuous tESCS that induced involuntary step-like movements were not formed by the amplitude modulation of monosynaptic reflexes, as it was in spinal rats and during the spinal epidural stimulation of patients. Our data showed that the activity within electromyographic trains was not stimulus-dependent; i.e., EMG trains did not consist of separate reflex responses. Similar stimulus-independent EMG trains were observed during involuntary movements caused by spinal cord electromagnetic stimulation. In contrast, the step-like movements evoked by the epidural spinal stimulation in rats and spinal patients were stimulus-dependent. In the extensor muscles, the EMG trains consisted mainly of monosynaptic reflexes; in the flexor muscles, polysynaptic reflexes dominated in the EMG trains. It is not clear why single cutaneous and, respectively, single epidural spinal cord stimulation causes the same monosynaptic reflexes in healthy subjects and spinal patients; however, continuous stimulation elicits their step-like movements through different mechanisms. In healthy subjects, tESCS can increase the excitability of the neuronal locomotor network, being a trigger for its activation, in the same way as in the case of vibration-induced step-like movements.

In this study, a new noninvasive access to locomotor spinal neural networks in humans by means of tESCS has been described. A special design of the stimulator, which generated bipolar pulses filled with high-frequency carrier, allowed us to stimulate the spinal cord relatively painlessly and elicit involuntary step-like movements. The fundamental importance of our study consists in the new data in favor of the existence of SN in humans that can coordinate stepping patterns and the evidence of the possibility to engage this SN using noninvasive effects on the structures of the spinal cord. This increases prospects for widespread use of transcutaneous techniques in electrical spinal cord stimulation to study the mechanisms underlying the regulation of the locomotor behavior in healthy subjects and for the rehabilitation and motor recovery of patients after spinal cord injuries and after other neuromotor dysfunctions.

Example 2

Voluntary Movements

Figure 13:
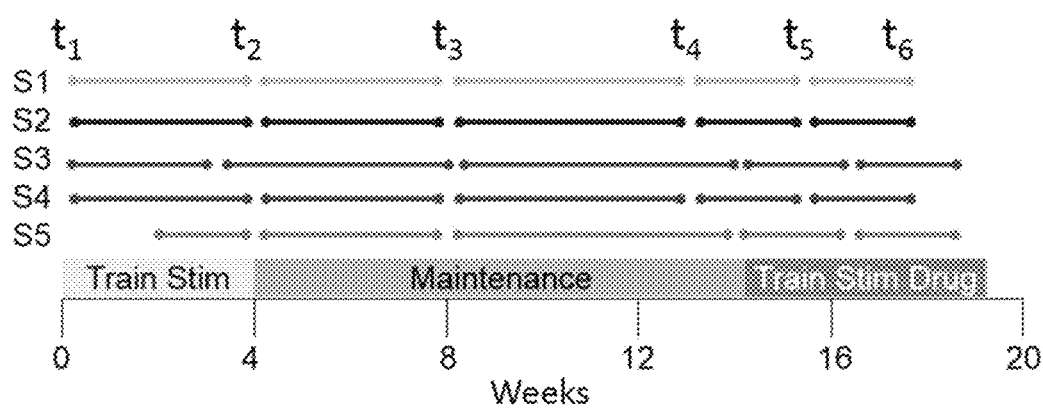
FIG. 13 illustrates an experimental timeline. The experimental plan is divided into three segments. During the first four weeks ($t_1$ to $t_2$, Train Stim) the subjects were trained with pcEmc at T11, Co1, and T11+Co1 plus conditioning. In the second phase ($t_2$-$t_4$, Maintenance) pcEmc tests were administered weekly using less intense stimulation at T11 or Co1, no simultaneous stimulation, and no conditioning procedures. This 10-week phase of the experimental protocol was designed to establish a stable functional baseline to more clearly differentiate the effects of pcEmc plus fEmc from pcEmc alone. The final four-week phase ($t_4$-$t_6$, Train Stim Drug) consisted of pcEmc plus conditioning as performed in the first phase with the addition of fEmc. S1-S5, Subjects 1-5.

We conducted a series of weekly training-testing sessions over a period of about 18 weeks (FIG. 13). Each session from $t_1$-$t_4$ consisted of stimulation at the level of T11, Co1, and the combination of the two sites with and without simultaneous voluntary effort to move the lower limb in a stepping motion. In addition, each session consisted of passively oscillating the limbs in a step-like fashion for three minutes without and three minutes with continuous stimulation. These passive perturbations conditioned each individual. From $t_2$-$t_4$, the same procedures were followed but without the conditioning perturbations. This reduced level of perturbation was designed to maintain and sustain a plateau performance prior to the initiation of the drug phase of the intervention.

Over the 18-week period, six recording sessions ($t_1$-$t_6$; FIG. 13) were performed of detailed assessments reflecting quality of stepping-like motions. In the first four weeks (4/5), subjects performed all four training-testing sessions, whereas subject 5 only two training-testing sessions at three and four weeks.

Figure 14A:
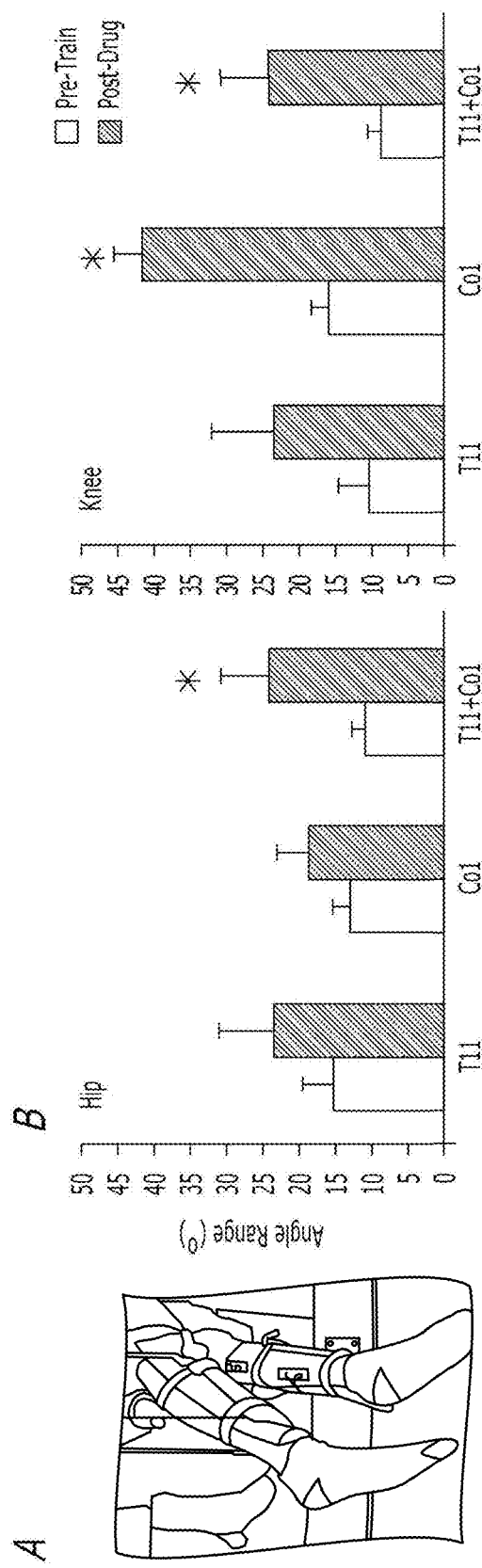
FIGS. 14A and 14B illustrate facilitation of stepping-like movements during non-invasive T11 and/or Co1 spinal cord stimulation.

To determine the effects of fEmc plus pcEmc the subjects were trained-tested weekly over a period of 4 weeks ($t_5$-$t_6$). To determine the potential for locomotor-like stepping all training and periodic testing ($t_1$-$t_6$) were performed in an apparatus designed to minimize gravitational effects (FIG. 14A).

Experimental design. The subjects were tested while lying on their left side with the upper leg supported directly in the area of the shank and the lower leg placed on a rotating brace attached to a horizontal board supported by vertical ropes secured to hooks in the ceiling. This arrangement allowed for the suspended legs to move in an anterior-posterior plane in a gravity-neutral position. For electrical stimulation at T11 and/or Co1 a specific stimulation or stimulation waveform can be and was used that does not elicit pain, even when used at energies required to transcutaneously reach the spinal cord. This stimulation can include a biphasic signal and an overlapping high frequency pulse. Painless transcutaneous electrical stimulation (pcEmc) was delivered using a 2.5 cm round electrode (Lead Lok, Sandpoint, United States) placed midline on the skin between spinous processes T11-T12 (simply T11) or over coccyx 1 (Co1) as a cathode and two 5.0×10.2 cm 2 rectangular plates made of conductive plastic (Ambu, Ballerup, Germany) placed symmetrically on the skin over the iliac crests as anodes.

Kinematics and EMG recordings. Leg movements were evoked by monopolar rectangular stimuli (1 ms duration) filled with a carrier frequency of 10 kHz and at an intensity ranging from 80 to 180 mA. The stimulation frequency was 30 Hz at T11 and 5 Hz at Co1. The duration of continuous exposure ranged from 10 to 180 s. Bipolar surface electrodes were placed bilaterally on the soleus, medial gastrocnemius (MG), tibialis anterior (TA), medial hamstring (HM), and vastus lateralis (VL) muscles. EMG signals were amplified differentially (bandwidth of 10 Hz to 10 kHz) and acquired at 10 KHz using a 16-channel hard-wired A/D board and customized LabVIEW software (National Instruments, Austin, TX) acquisition program. To minimize artifacts from the stimulation, the EMG signals were passed through a band-pass filter using a six-order band-pass Butterworth filter (30-200 Hz). The filtered EMG signals were analyzed off-line to compute the amplitude, duration, and timing of individual bursts.

Angular displacements at hip and knee joints in both legs were recorded with goniometers. Two procedural sequences were followed for each subject on a given day of testing. Each subject was tested weekly up to eighteen weeks. The subjects had access to visual feedback via a mirror placed so that movement of the legs could be observed.

Conditioning procedures. The conditioning procedure consisted of imposing passive movement of the legs in an oscillatory pattern for three minutes (conditioning) and then imposing a passive movement plus stimulation at T11, Co1 or T11+Co1 simultaneously for three minutes. The total time for each testing session was about 45 minutes. The same protocol was followed once a week for the first and last four weeks. Whether the conditioning treatment only within a single training session could facilitate the ability to generate knee oscillations without and with stimulation at $t_6$ (FIGS. 19A-19D) was also tested.

Figure 15A:
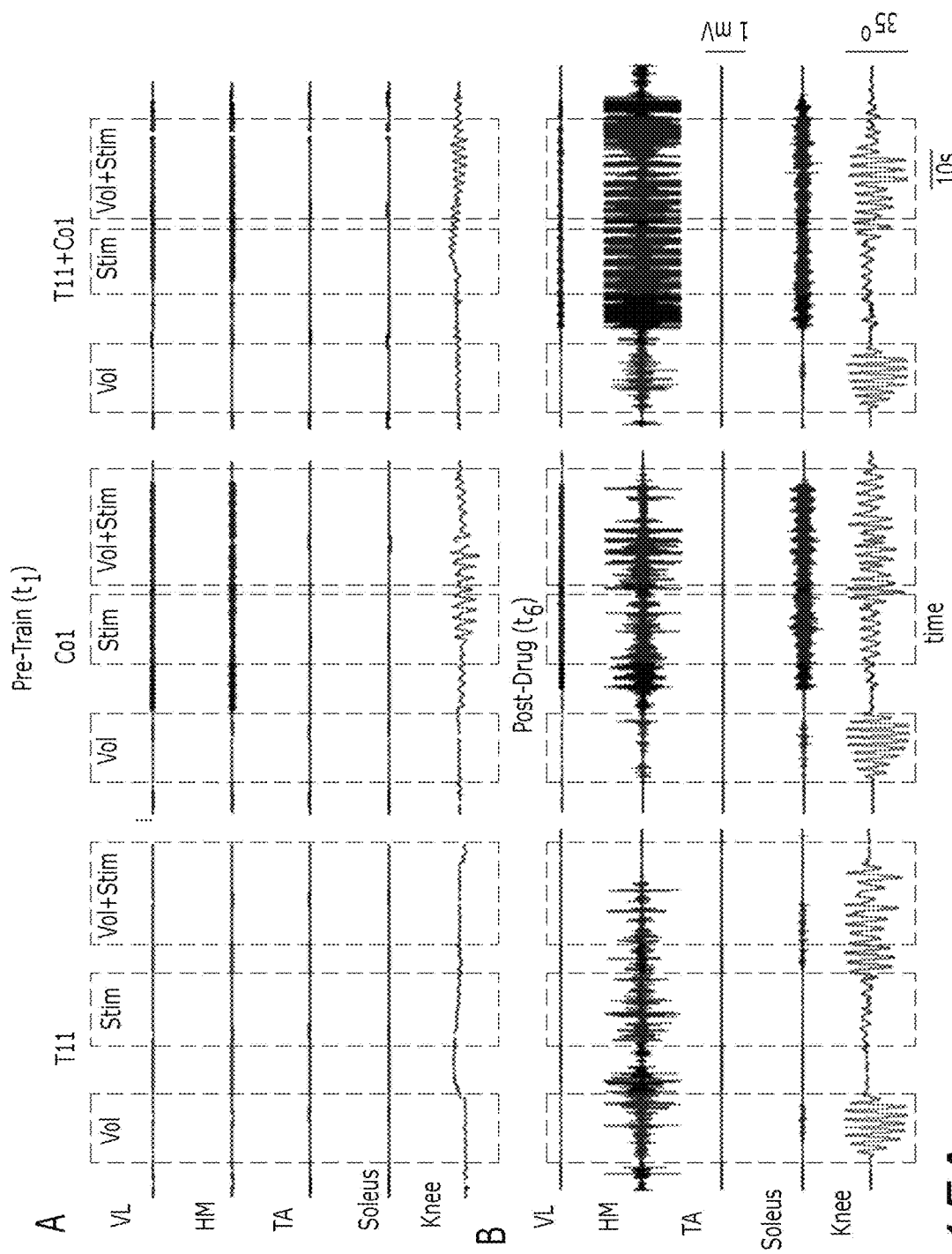
FIGS. 15A and 15B illustrate voluntary control of leg movements enabled by pcEmc, fEmc, and training. Vastus lateralis (VL), hamstrings (HM), tibialis anterior (TA), and soleus raw EMG and angular displacement at the knee during leg oscillations with a voluntary effort alone (Vol), stimulation at T11, Co1, or T11+Co1 alone (Stim), and Vol+Stim at the Pre-Train (FIG. 15a; $t_1$) and Post-Drug (FIG. 15B; $t_6$) phases.
Figure 15B:
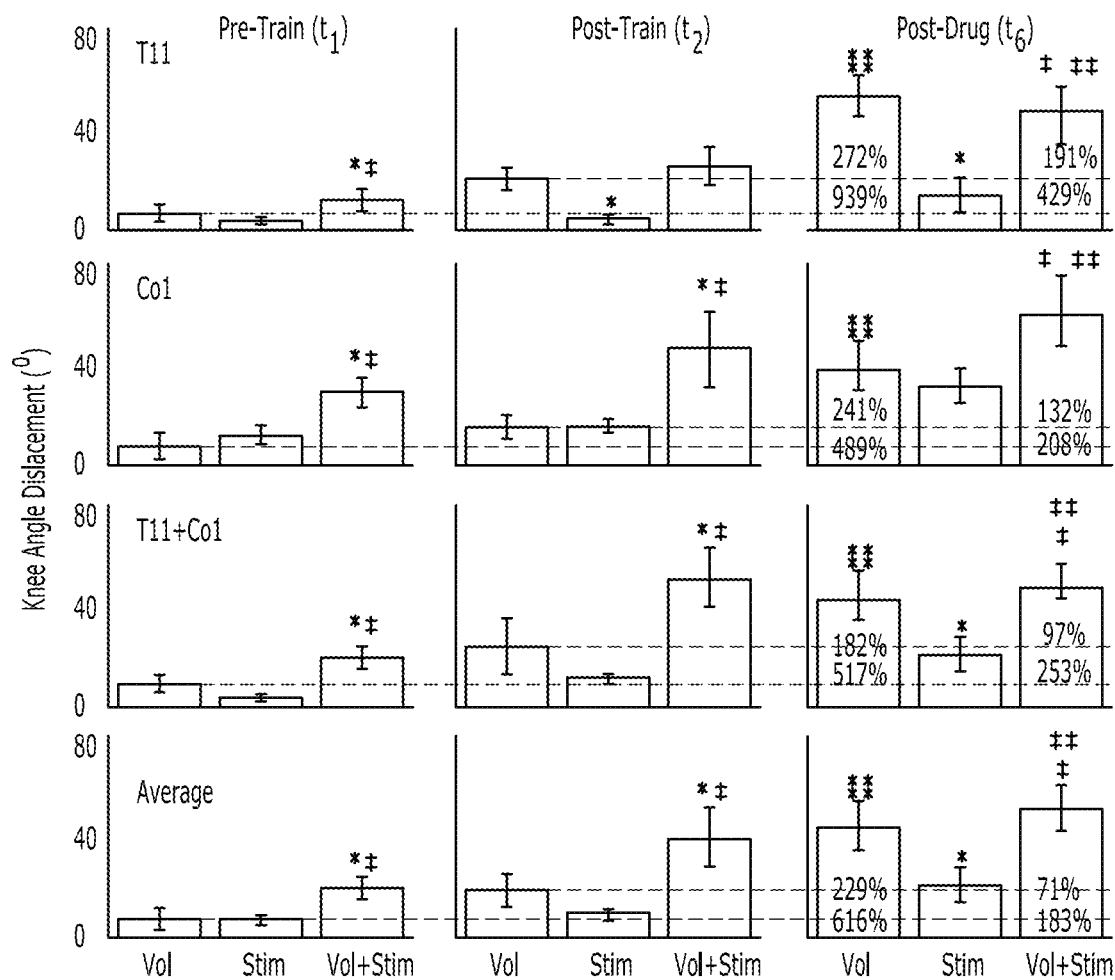

Drug treatment. All subjects were informed that they would receive either a placebo or the serotoninergic agonist buspirone. All subjects were given buspirone 7.5 mg orally twice daily for the last 4 weeks (FIG. 13 and FIG. 15B).

Clinical statement of the patients. The University of California, Los Angeles Institutional Review Board approved all procedures. Subjects were enrolled based on the enrollment criteria of traumatic cervical or thoracic injury, AIS B, greater than 1 year from injury, and stable motor function as documented by sequential clinical exams.

The clinical profiles of the subjects upon enrollment into this study are as follows: Subject 1 (S1) is a 42 year old male who suffered a T3-T4 SCI after a steer wrestling accident and was 24 months from initial injury. S2 is a 20 year old male who suffered a C5-C6 SCI sustained during a football game and was 36 months from initial injury; S3 is a 20 year old male who suffered a C6 SCI after a motor vehicle accident and was 36 months from initial injury; S4 is a 19 year old male who suffered a C7 SCI during a swimming accident and was 24 months from injury; and S5 is a 56 year old male who suffered a T3-T4 SCI after a bicycle accident and was 72 months from injury. Magnetic resonance imaging was obtained in all subjects to confirm the location and extent of the injury (FIG. 8).

Electrophysiological assessment of the patients. Transcranial magnetic motor evoked potential (MEP) tests and lower extremity somatosensory evoked potential (SEP) tests were obtained in all subjects. For MEP, all subjects demonstrated absence of lower extremity muscle activity upon stimulation at the cortical level and no conduction was observed through the level of impairment. For SEP, subjects demonstrated absence of cortical peaks bilaterally with no evidence of conduction across the known spinal cord injury.

Figure 20:
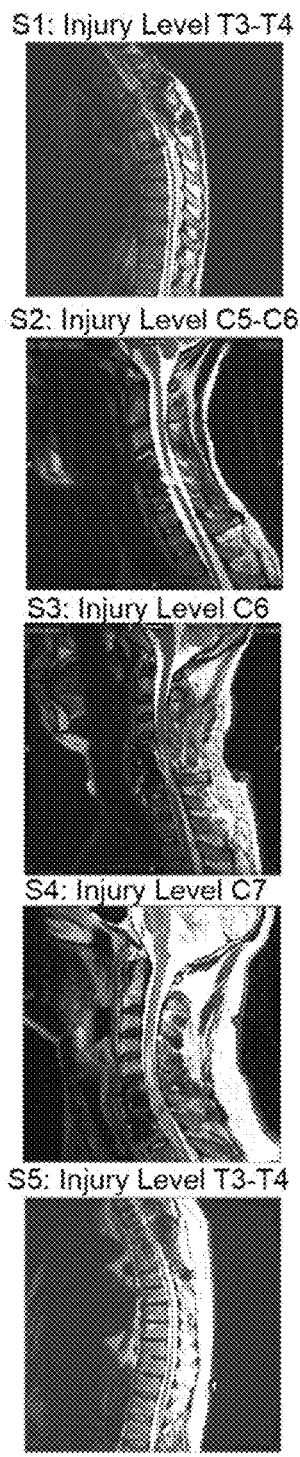
FIG. 20 illustrates MRI images of the five SCI subjects. Sagittal MRI showing the approximate location (spinal cord segment) of the cervical or thoracic spinal cord injury in each subject: S1—injury level T3-T4, S2—injury level C5-C6, S3—injury level C6, S4—injury level C7, and S5—injury level T3-T4. Normal tissue at the injury site is replaced by a high or mixed intensity signal representing a glial scar. Spinal cord tissue distal and proximal to the injury site appears intact without any evidence of progressive post-traumatic syrinx formation or ongoing compressive lesion. Some image artifact from the instrumentation distorting the spinal cord image can be visualized.
Figure 21A:
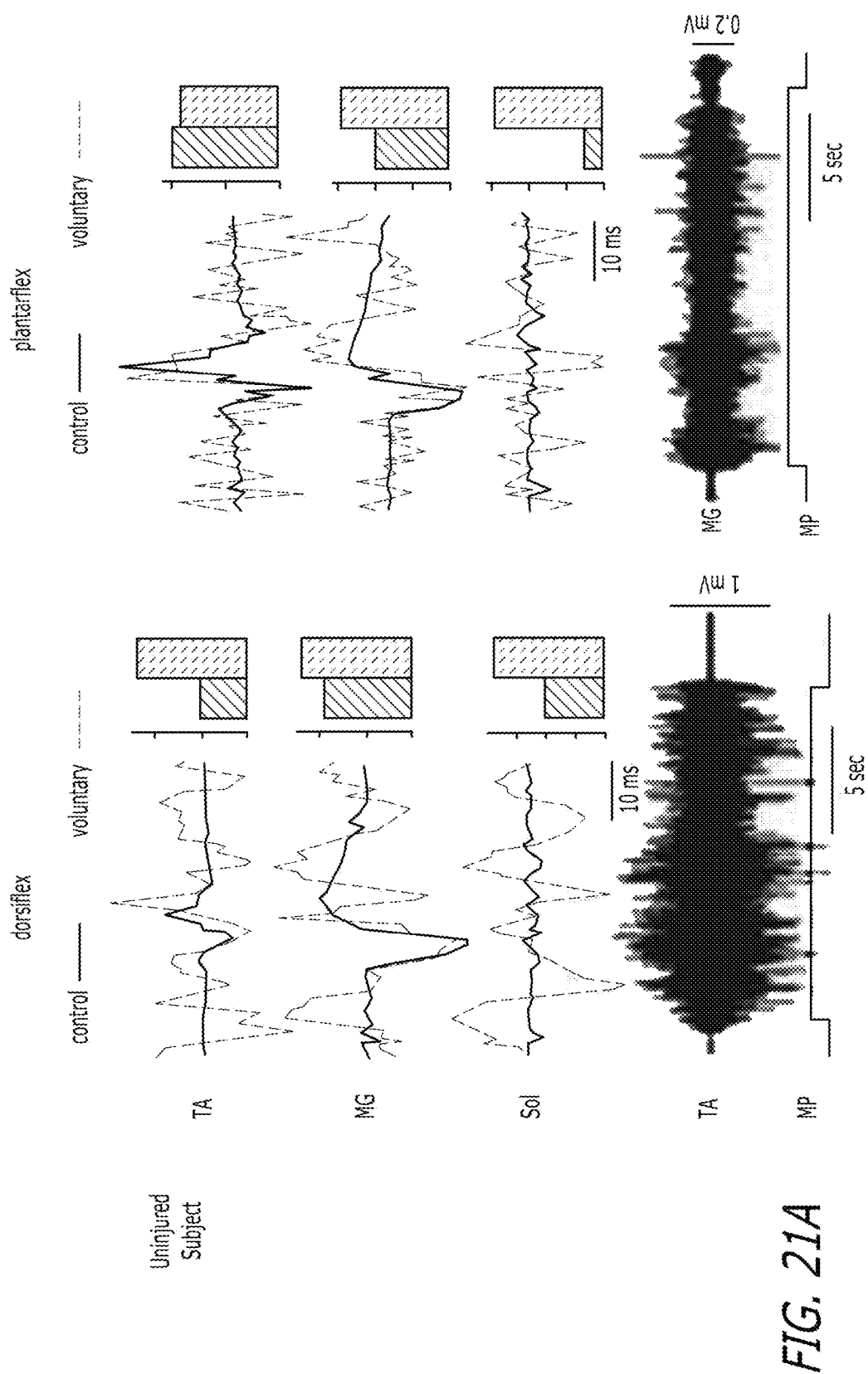
Figure 21B:
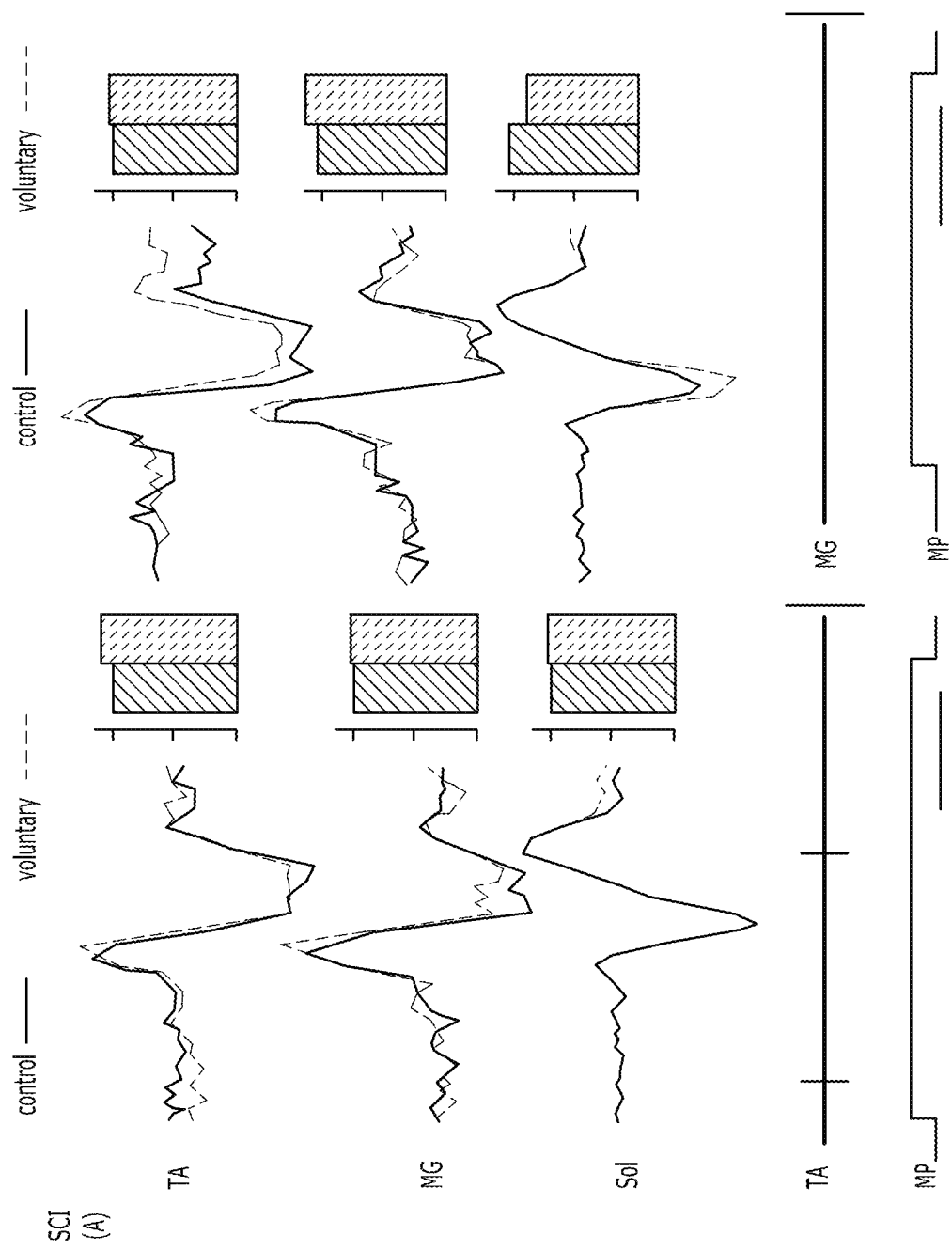
Figure 21C:
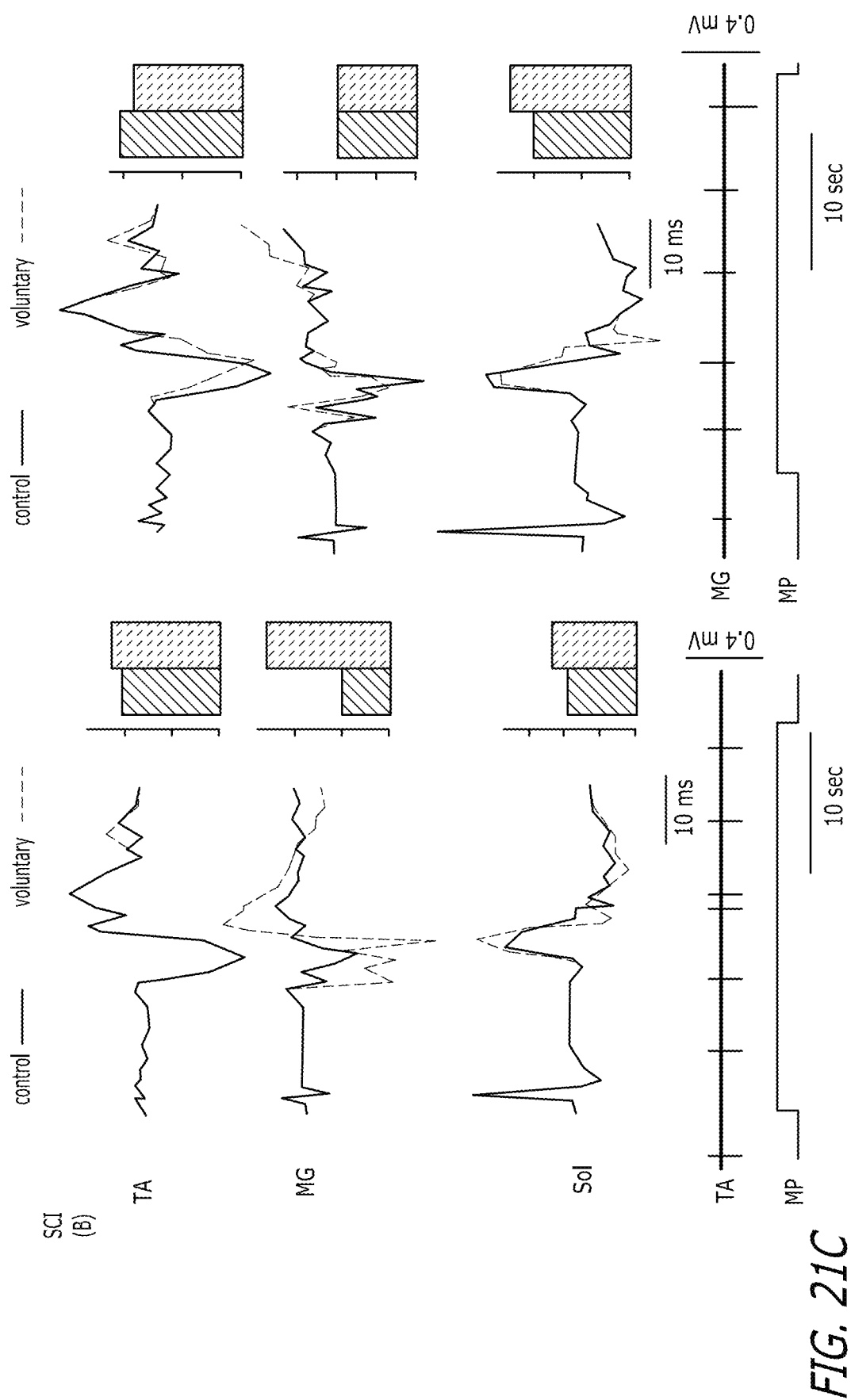
Figure 21D:
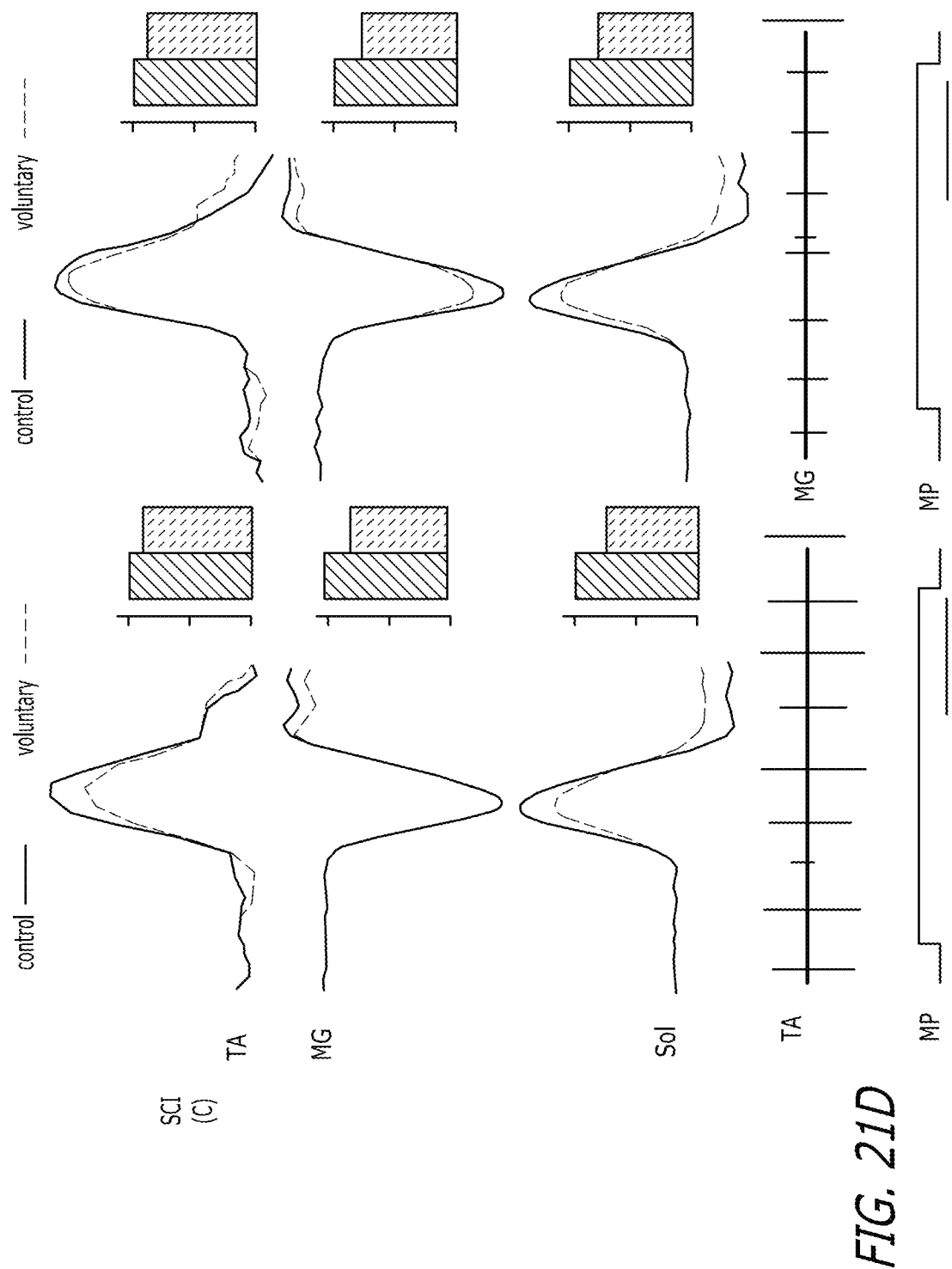
Figure 21F:
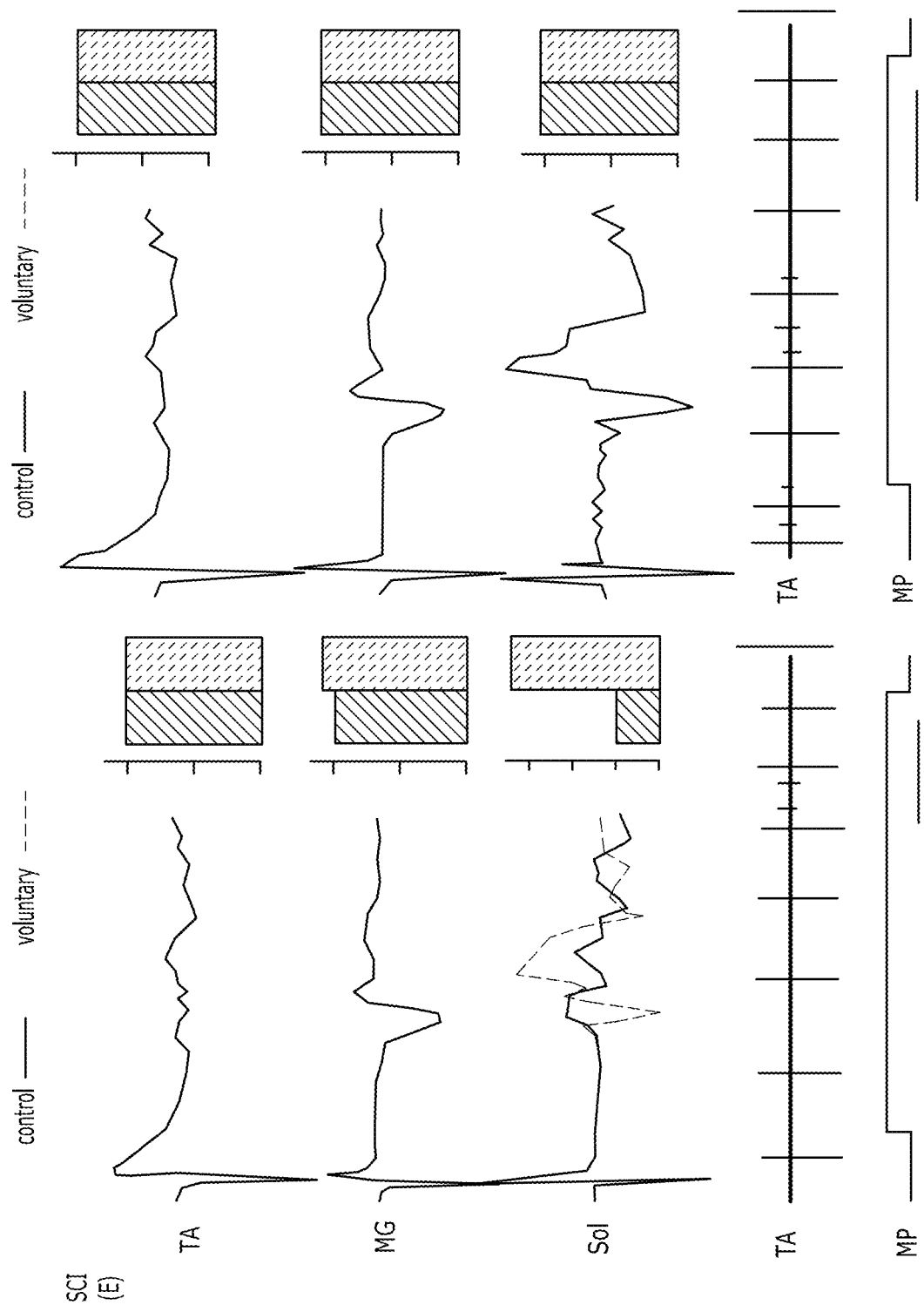

Additionally, the ability to control the leg muscles voluntarily was tested in all subjects while in a supine position. Flexor (TA) EMG was recorded during dorsiflexion and extensor (MG and soleus) EMG during plantarflexion and evoked potentials were recorded in the leg muscles in response to pcEmc at T11-T12 during attempts to maximally dorsiflex or plantarflex. In uninjured subjects, the amplitudes of the muscle evoked potentials were higher with a voluntary contraction compared to those recorded at rest (FIG. 21A). In all SCI subjects there was minimal EMG activity during these attempts and the amplitude of the evoked potentials were similar to those recorded at rest (FIGS. 21B-21F). In two subjects (S2 and S5) the intent to dorsiflex surprisingly led to an increase in the amplitude of the evoked potentials in the extensor, but not the flexor, muscles (FIGS. 21C and 21F), indicating aberrant neuronal (or neuromuscular) connections. These electrophysiological results indicate that voluntary control of the leg muscles was absent in these patients. These electrophysiological assessments are consistent with the morphological assessments derived from MRI (FIG. 20).

Assessment of voluntary movements. The ability to facilitate voluntarily generated locomotor-like movements during spinal cord pcEmc when the legs were placed in a gravity-neutral position was determined. After instructing each subject to oscillate the limbs as if stepping, the subject was asked to relax for a period of 15-20 sec before we initiated pcEmc with the cathode at the T11 and/or Co1 vertebral level. Then, the subject was asked to attempt to voluntarily oscillate the legs in the presence at T11, Co1, or T11+Co1. In the first Pre-Train session without pcEmc, initially none of the subjects could voluntarily initiate or influence rhythmic locomotor-like limb movements and rhythmic EMG activity of the leg muscles. After treatment with buspirone (Post-Drug), all subjects improved in generating oscillatory, locomotor-like movements with only a voluntary effort and the robustness of the movement was similar when voluntary effort was combined with pcEmc at T11+Co1 (FIG. 15C).

Statistical analyses. All statistics were performed in SPSS v.19 (IBM) with base, regression, advanced models, and categories packages. Non-linear PCA (NL-PCA) was implemented using the CATPCA command with appropriate link functions to accommodate non-linear and non-normal distributional features for each variable. PC (object) scores were extracted across all endpoints, subjects, and levels of the repeated measures. PC retention was determined by the eigenvalue >1 rule, and the face validity of PC loading patterns. PC1 scores then were carried forward as the principal outcomes for assessing the impact of the experimental manipulations by 3-way repeated measures ANOVA (GLM command), with each subject serving as their own control. Significant interactions were followed up by interaction graphing with assessment specific differences by one-way ANOVA and Tukey's post-hoc. Significance was assessed at P<0.05.

Figure 14B:
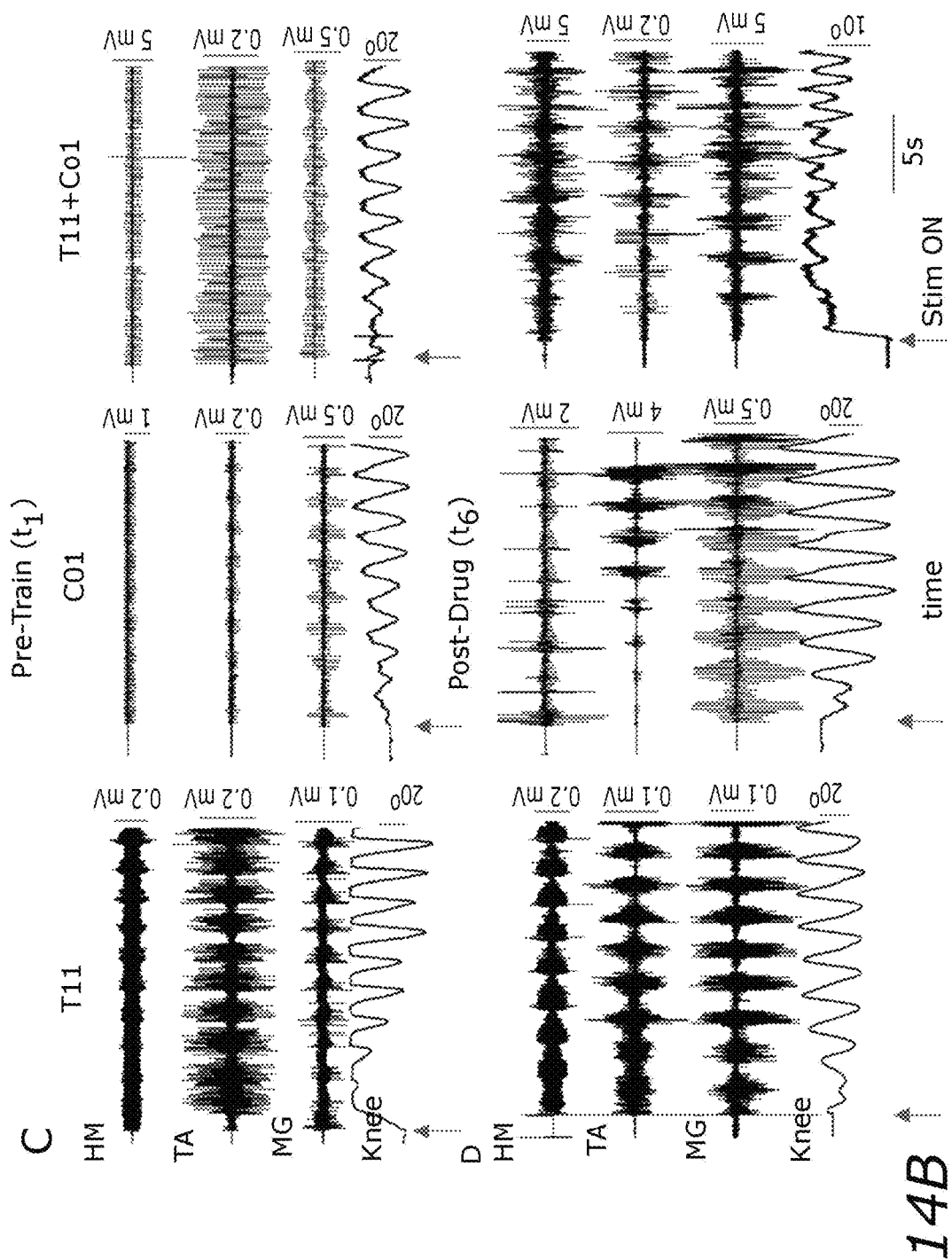

PcEmc activation of locomotor neuronal networks was assessed. During the first testing session ($t_1$) some rhythmic hip and knee movements and corresponding EMG activity were induced during pcEmc without any voluntary effort when the legs were placed in a gravity-neutral position (FIG. 14A). Examples of the relative effects of spinal cord stimulation with the electrodes placed at T11 (30 Hz) or Co1 (5 Hz) vertebral levels and the combination of stimulation from both sites simultaneously on these leg movements in the same subject during Pre-Train ($t_1$) and Post-Drug ($t_6$) are illustrated in FIG. 14C and FIG. 14D (same subject at $t_1$ and $t_6$ under each stimulation condition), respectively. The mean amplitudes of the angular movements at the hip and knee joints during voluntary efforts with and without stimulation were generally greater Post-Drug than Pre-Train (FIG. 14B). In addition, the EMG bursts were generally more robust Post-Drug than Pre-Train (FIG. 14C vs. FIG. 14D).

Also, voluntary control of leg movements enabled by pcEmc and training was assessed. Initially ($t_1$) none of the subjects could voluntarily initiate rhythmic locomotor-like limb movements with any detectable rhythmic EMG activity of the leg muscles (FIG. 15A). On the first day of testing ($t_1$), there was more than a two-fold increase (P<0.05) in the knee angle oscillatory range with a combination of voluntary effort and pcEmc compared to a voluntary effort alone or pcEmc alone (FIG. 15B; $t_1$). Some movement occurred at $t_1$ with voluntary effort alone, but this was without any EMG oscillatory responses and occurred due to the subjects mechanically transferring trunk and hip motion to the lower limbs. At the end of the four weeks of training with pcEmc ($t_2$), the subjects had not recovered a significant level of knee movement during a voluntary effort with or without stimulation (FIG. 15B).

Figure 16A:
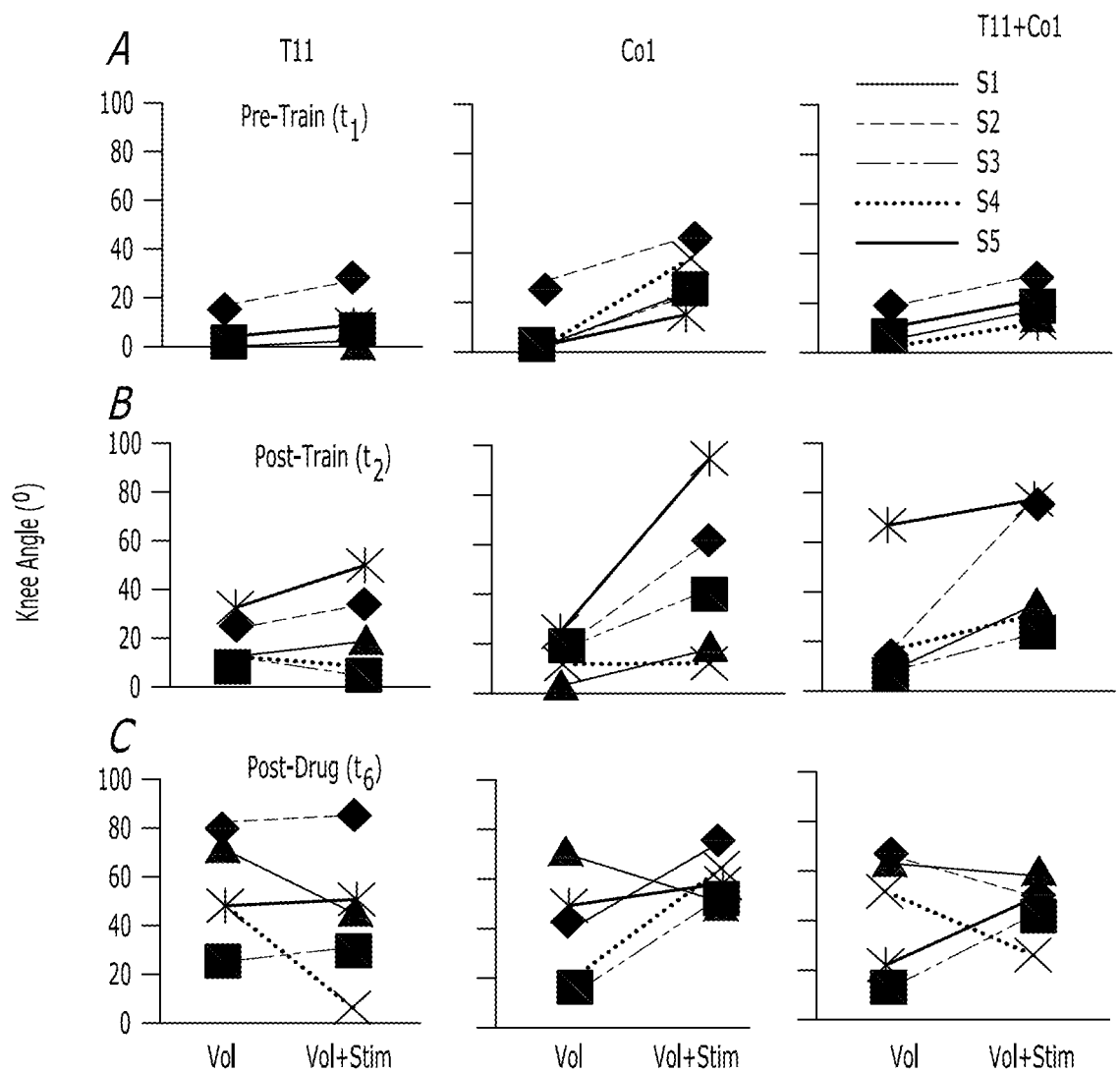
FIGS. 16A-16C illustrate subject specific kinematics responses and non-linear principal component analyses. Mean angular displacements of the knee at the (FIG. 16A) Pre-Train, Post-Train, and Post-Drug phases for each subject during Vol and Vol+Stim. S1-S5, subjects 1-5.
Figure 16B:
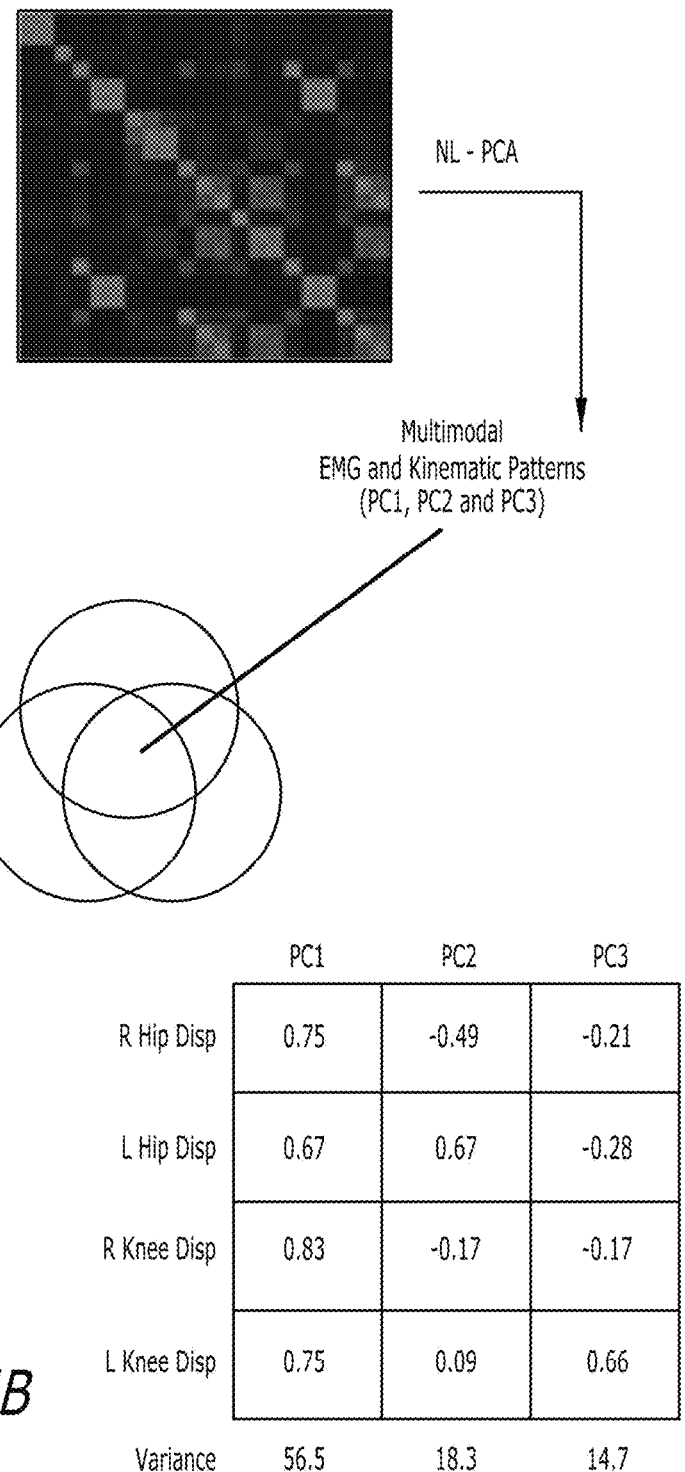
Figure 16C:
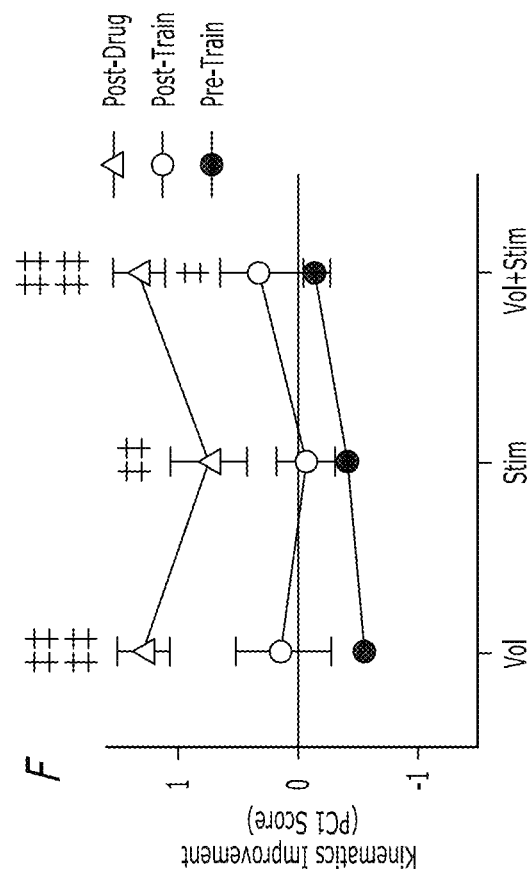
Figure 16C:
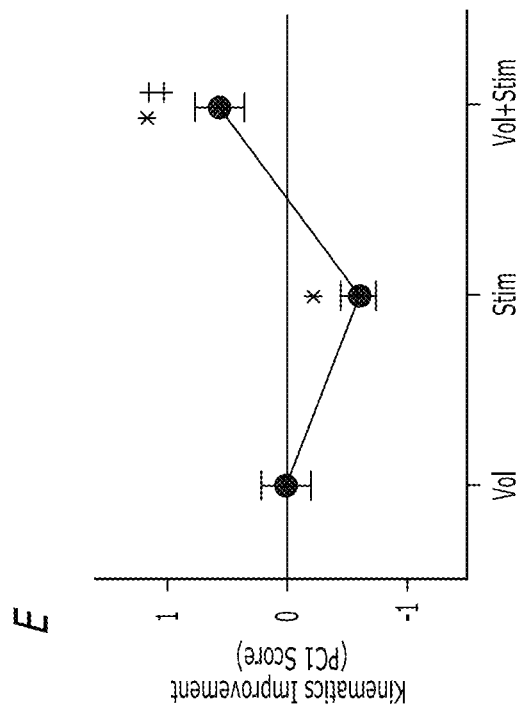

Relative effectiveness of voluntary effort compared to voluntary effort plus pcEmc changed at the Post-Drug phase ($t_6$). At the end of the drug phase, the overall performance during voluntary effort alone was as effective as voluntary effort plus stimulation (FIG. 15B). The average range of voluntary movement at the knee Post-Drug ($t_6$) was two-fold greater than Pre-Drug ($t_2$) and six-fold greater than at the initial test ($t_1$) (FIG. 15B). These mean differences (FIG. 15B) are even more impressive when considering the variation in the responsiveness to pcEmc as a function of subject specificity and the site of pcEmc in the response to fEmc treatment (FIGS. 16A-16C). For example, the angular displacement for 51 was lower Post-Drug ($t_6$) with the combination of voluntary effort plus stimulation at T11 vs. voluntary effort alone. This occurred at each of the stimulation sites for this subject. This also occurred with subject 4 with the stimulation sites involving T11 and T11 plus Co1.

Although the effects of pcEmc at different spinal levels and at different phases of the interventions varied among subjects, non-linear principal component analysis (NL-PCA) revealed a consistent linkage pattern between the hip and knee angular displacements (FIGS. 16B-16C). Based on PC1 there was an emergence of organized oscillations in response to pcEmc, fEmc, and training.

Figure 17A:
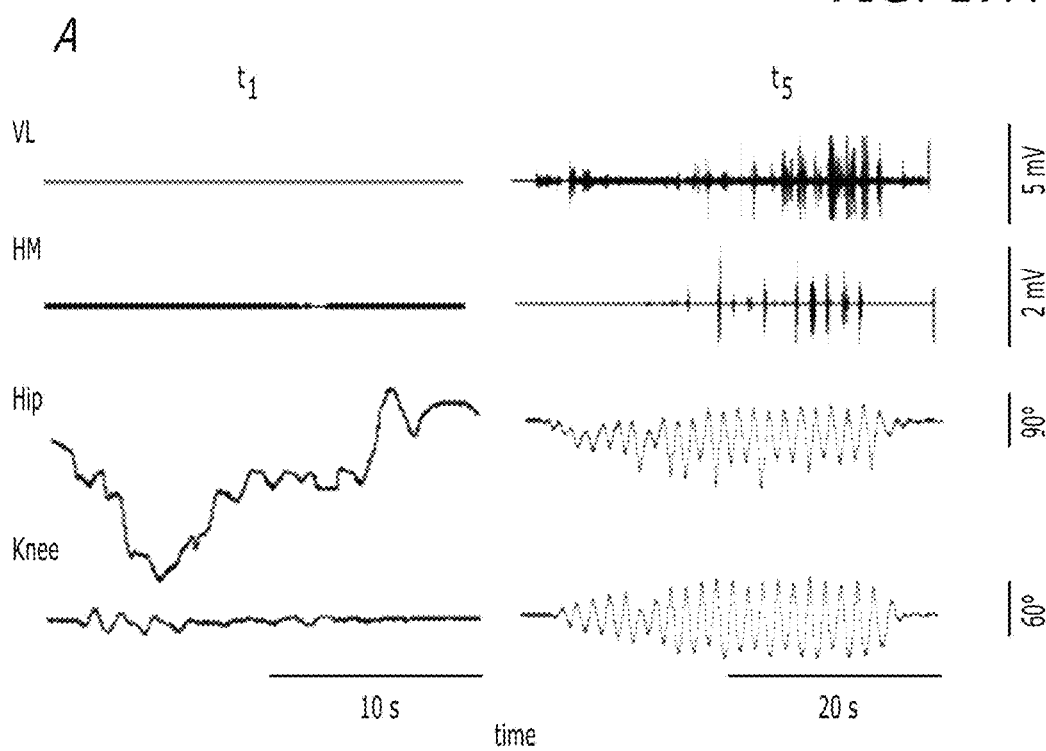
Figure 17B:
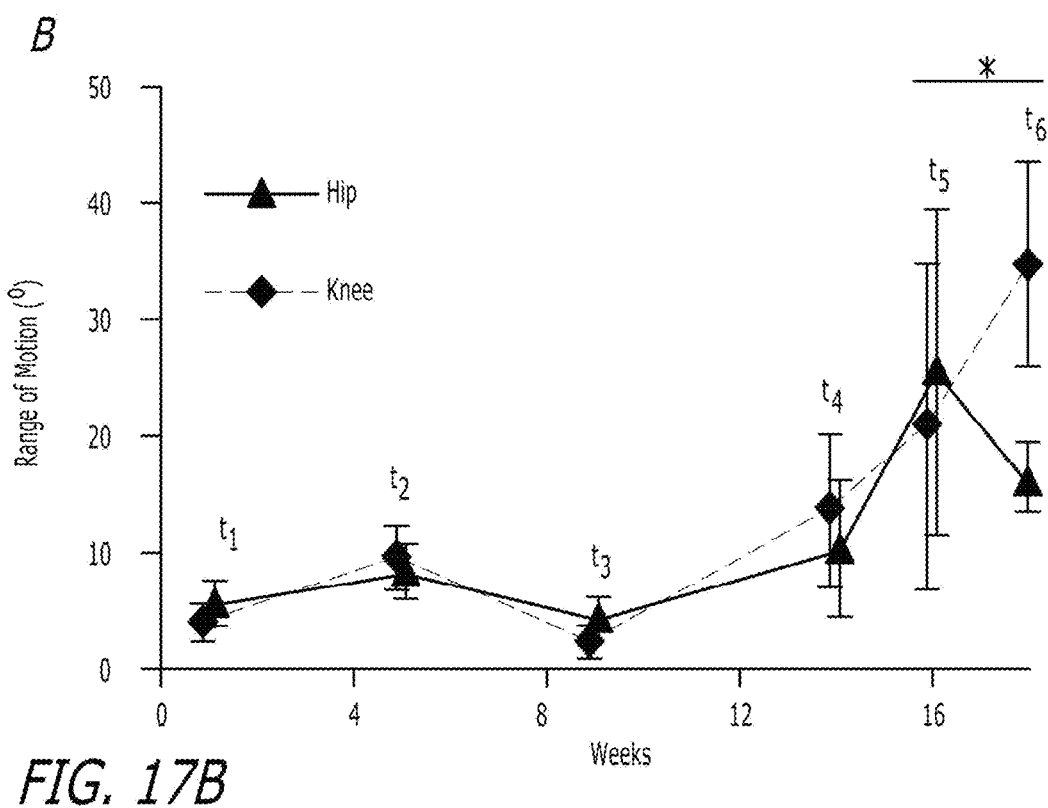
FIG. 17B illustrates mean±SEM (n=5 subjects) range of oscillations of the hip and knee at the six test recording time points ($t_1$-$t_6$).

To determine whether there was an additive effect of fEmc to that observed with pcEmc and training further test were performed. An example of one subject's hip and knee displacements and the EMG of selected muscles at $t_1$ vs. $t_5$ is shown in FIG. 17A. Clear rhythmic EMG bursting and oscillatory movement of the hip and knee at is was compared to $t_1$. After two weeks of pcEmc+fEmc treatment (FIG. 17B; $t_5$), a significant facilitation in the mean voluntary performance (without pcEmc) of locomotor-like movements and this effect continued after two more weeks of pcEmc plus fEmc treatment (FIG. 17B; $t_6$) was observed. These statistical comparisons suggest that 1) the magnitude of the range in knee oscillations was increased with voluntary effort plus pcEmc at $t_1$ even within the first test session (FIG. 15B and FIG. 16C), 2) there was a further increase in the range of these oscillations after four weeks of fEmc ($t_6$) (FIG. 15B and FIG. 16C), and 3) there was notable subject-specificity for the stimulation site that evoked the greatest responses to the interventions at all phases (FIGS. 16A-16C).

Figure 17C:
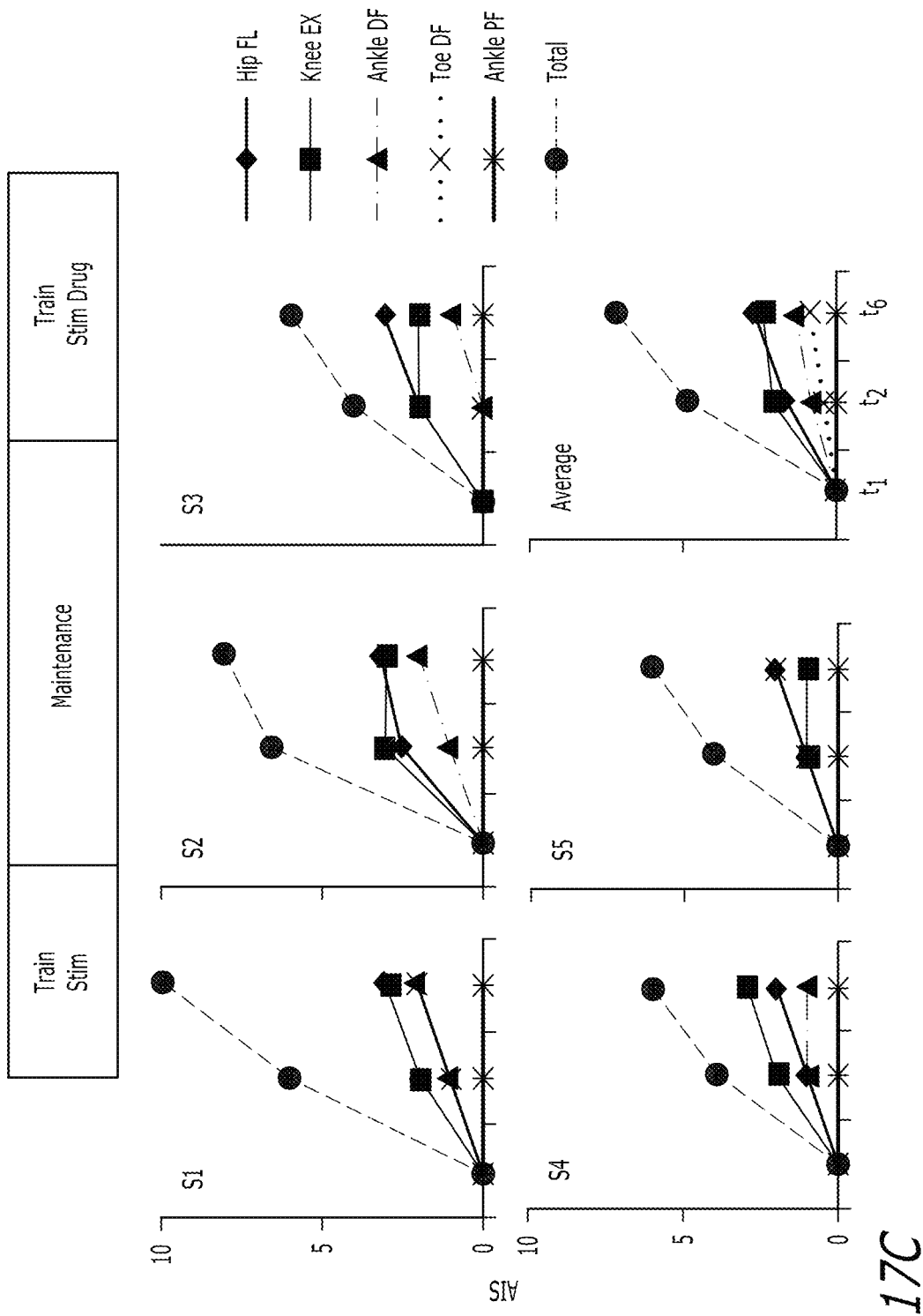
FIG. 17C illustrates AIS motor scores at $t_1$, $t_2$, and $t_6$ for individual subjects (S1-S5) and the average for all subjects. An "*" represents a significant difference between $t_5$-$t_6$ vs. $t_1$-$t_4$. FL, flexion; EX, extension; DF, dorsiflexion; PF, plantarflexion.

Clinical assessment according to the ASIA impairment scale (AIS) is consistent with improvement of motor function after pcEmc+fEmc treatment in all five subjects (FIG. 17C). No clinical movement (score of 0) was observed in any of the lower extremity joints at the Pre-Train phase ($t_1$). An average improvement of 7 points was observed in this cohort during the Post-Drug ($t_6$) condition. In the presence of these interventions this would be equivalent to the subjects being reclassified from AIS B to C.

Figure 18A:
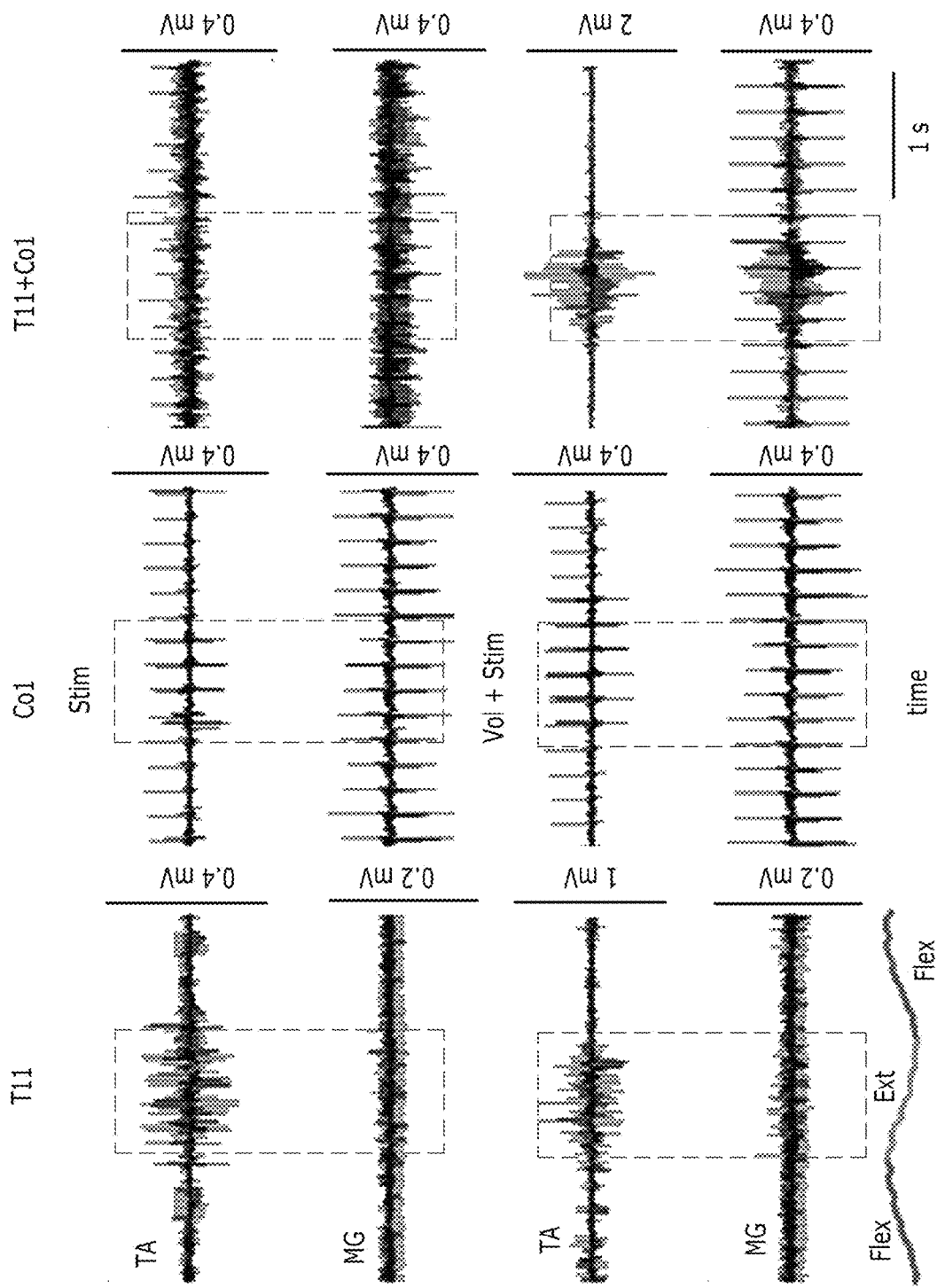
FIGS. 18A-18D illustrate modulation of evoked potentials with and without voluntary effort.

Further, modulation of evoked potentials during voluntary efforts was assessed. While monitoring varying physiological states of the spinal circuits in vivo while performing motor tasks in animals and human subjects, we demonstrated electrophysiological evidence of supraspinally mediated neuromodulation of the spinal circuitry in the present subjects. To assess these interactions we recorded spinally evoked potentials generated in the TA and MG muscles when the subject was lying in the gravity-neutral apparatus. We asked the subject to swing the leg forward (flex) and backward (extend; shaded areas in FIG. 18A) and then forward again in the presence of continuous stimulation.

Figure 18B:
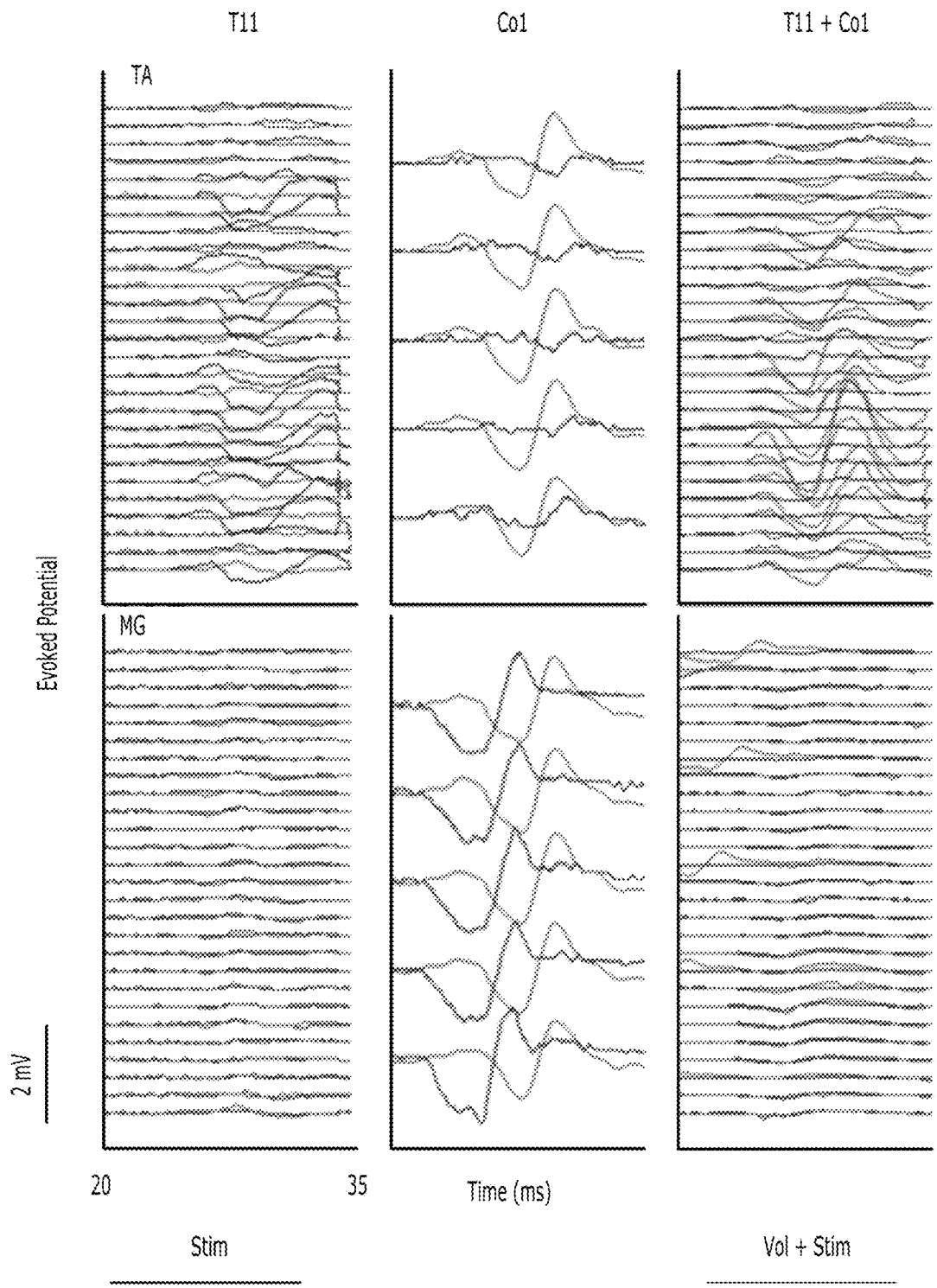
Figure 18C:
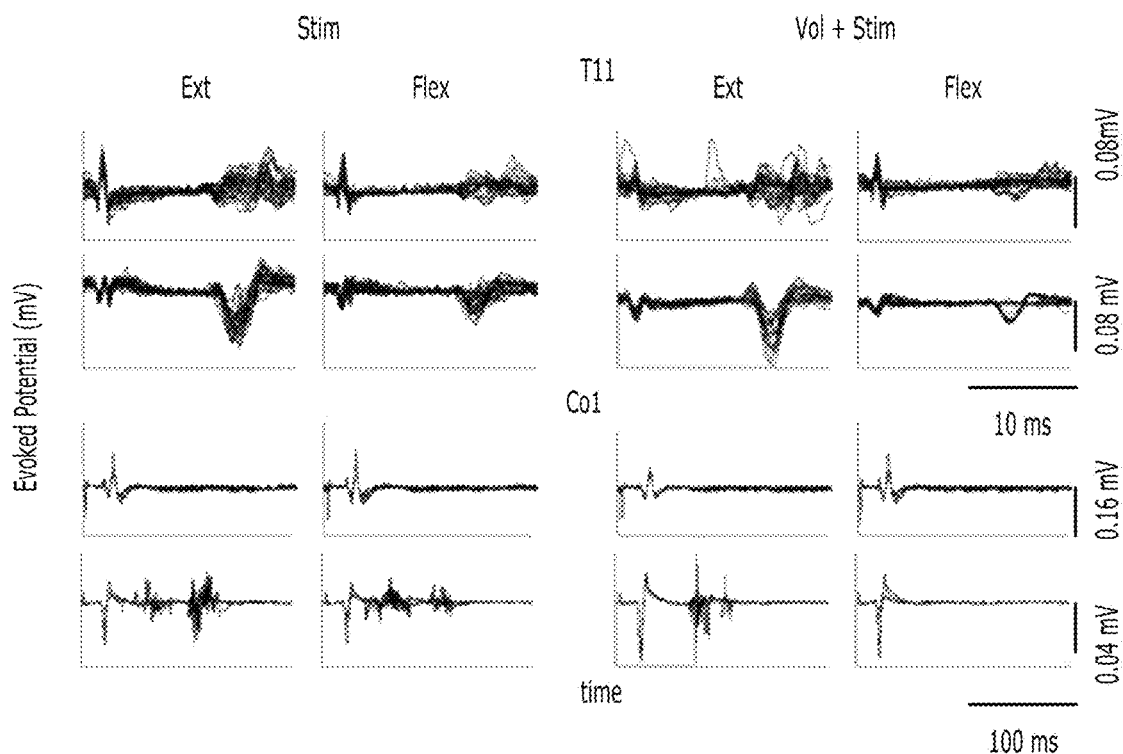

FIGS. 18B and 18C show examples of the malleability of the brain-to-muscle connections in response to different pcEmc stimuli in the presence and absence of voluntary efforts to flex or extend the lower limbs. Also, by testing this brain-spinal connectivity when stimulating at the level of Co1 and/or T11, we observed clear inhibitory and excitatory patterns of responses in the TA and MG motor pools depending on the stimulation site. When stimulating at Co1 we observed a clear facilitation of the TA motor pool mediated by voluntary effort, whereas the MG motor pool was slightly suppressed with voluntary effort.

Figure 18D:
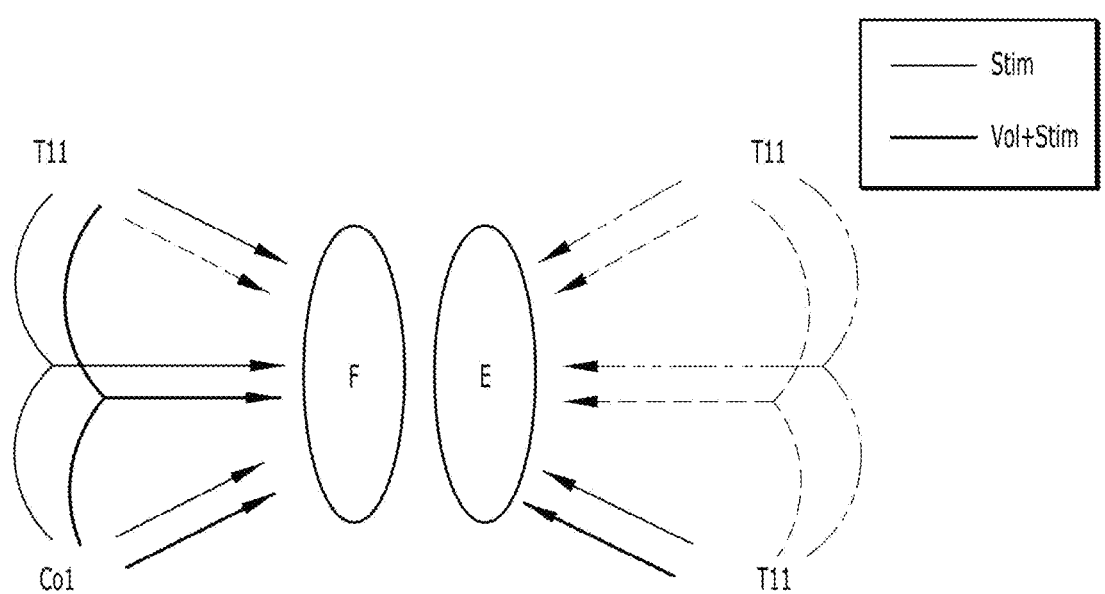

In some embodiments, a consistent delay of the response of approximately 2 ms in the MG was observed when there was a voluntary effort to extend the lower limb (FIG. 18B). The complexity of the functional brain-spinal connectivity is illustrated further by the suppression of any response in the MG when T11 and Co1 were stimulated simultaneously with or without voluntary effort and an evoked potential only occurring in the TA when there was a voluntary effort to extend (FIG. 18B). These interactive effects of stimulation at different sites with and without voluntary efforts are summarized graphically in FIG. 18D.

In other embodiments, a combination of pcEmc, fEmc, and training can open new functional connections among brain-spinal cord networks and that these functional connections are highly dynamic and interactive. Given that significant improvements in motor function can continue to emerge three years after the implantation of epidural electrodes and the responses of individual motor pools to the newly emerged descending voluntary input to the spinal circuitry to pcEmc at different frequencies and at different sites along the spinal cord, interactions of each of these modulatory components are highly interdependent.

Further still, proprioceptive conditioning effects on voluntary leg movements were assessed. To show that the properties of these brain-spinal cord networks (e.g., circuitry plasticity over a period of weeks) could be modulated more acutely, at $t_6$ we tested whether the proprioceptive-induced conditioning treatment within a single training session could facilitate the ability to generate knee oscillations with a voluntary effort alone or with a voluntary effort plus stimulation. The conditioning treatment consisted of imposing passive, continuous, anterior-posterior limb movements in an oscillatory step-like pattern (about 20 cycles/min) for three minutes without stimulation followed by three minutes with stimulation either at T11, Co1, or T11+Co1 with the subject's legs in a gravity-neutral apparatus.

Changes in the EMG and kinematics output over the progression of a single three-minute conditioning session without pcEmc and then with pcEmc at T11 were followed. When we compared the EMG and kinematics responses during the first 30 seconds and the final 30 seconds of the three-minute conditioning bout, a gradual increase in EMG amplitude during the initial 30 seconds and remained elevated up to the final 30 seconds with little or no change in the kinematics with and without pcEmc (FIG. 19A) was observed. An important difference was that the level of neuromodulation during conditioning combined with pcEmc was significantly greater than conditioning without pcEmc. Improved coordination of the motor pools for the knee and ankle flexors and extensors over these different 30-second time periods under each condition noted above also were evident (FIG. 19B).

Figure 19A:
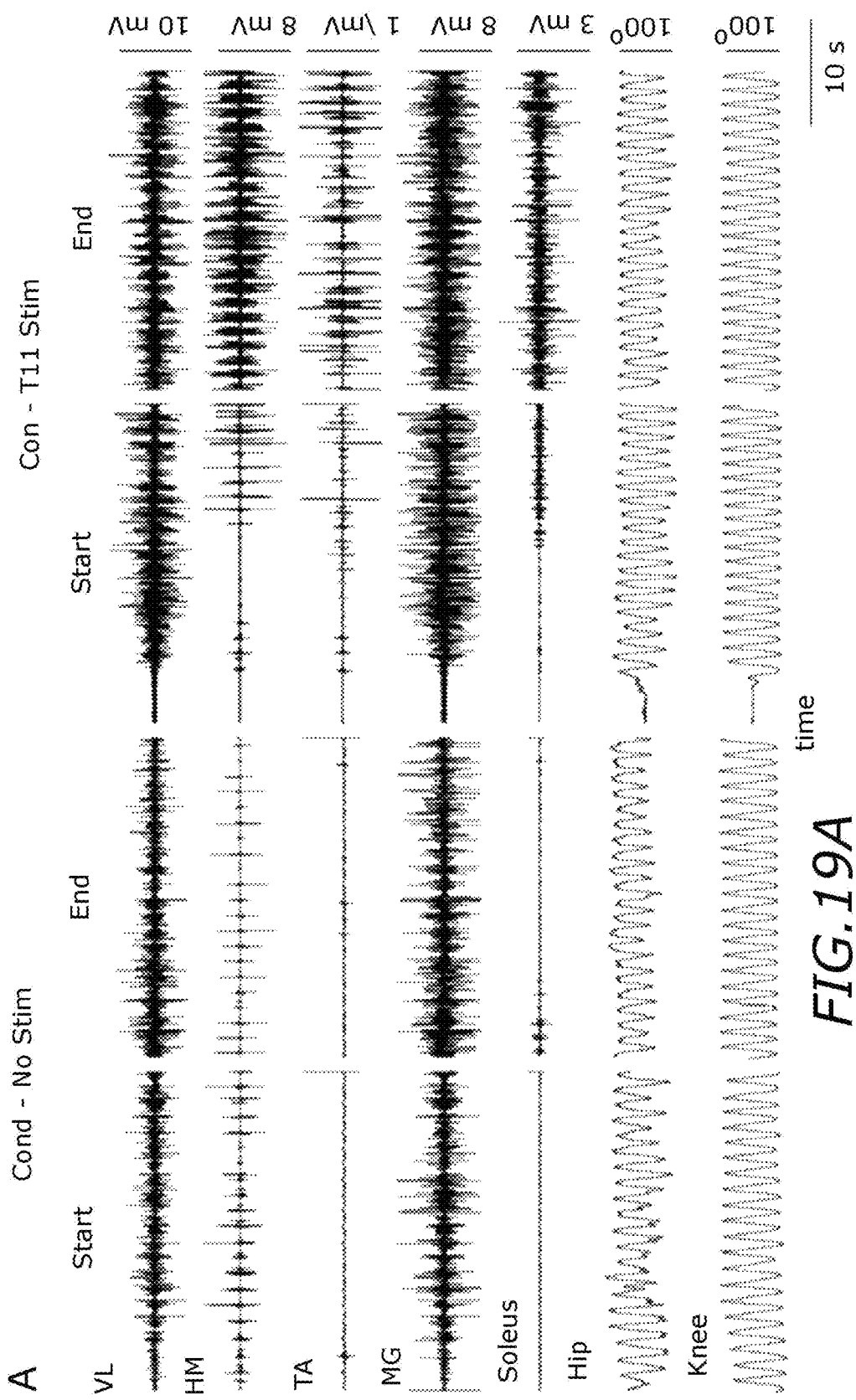
FIGS. 19A-19D illustrate effects of proprioceptive conditioning on voluntary leg movements.
Figure 19B:
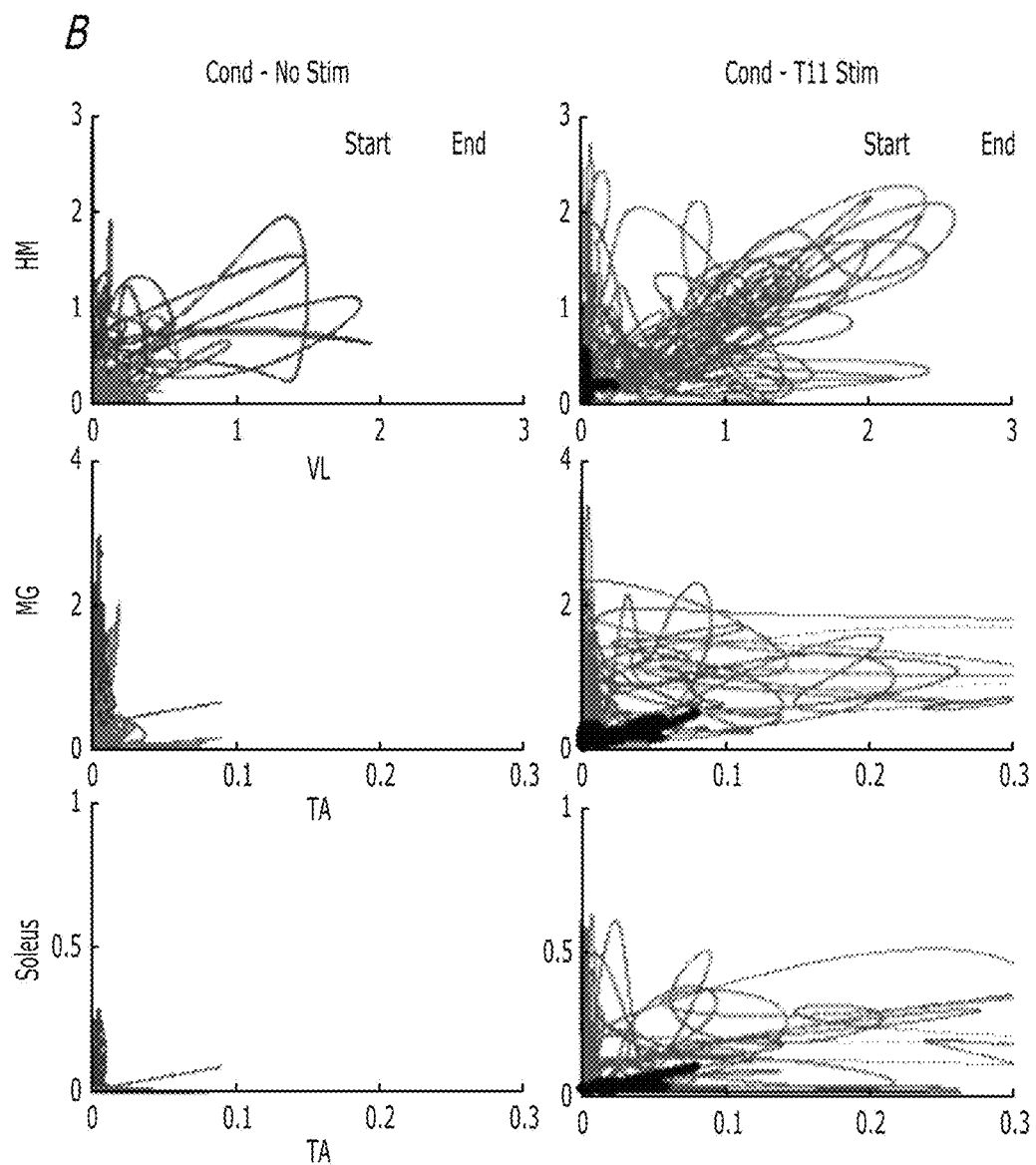
Figure 19C:
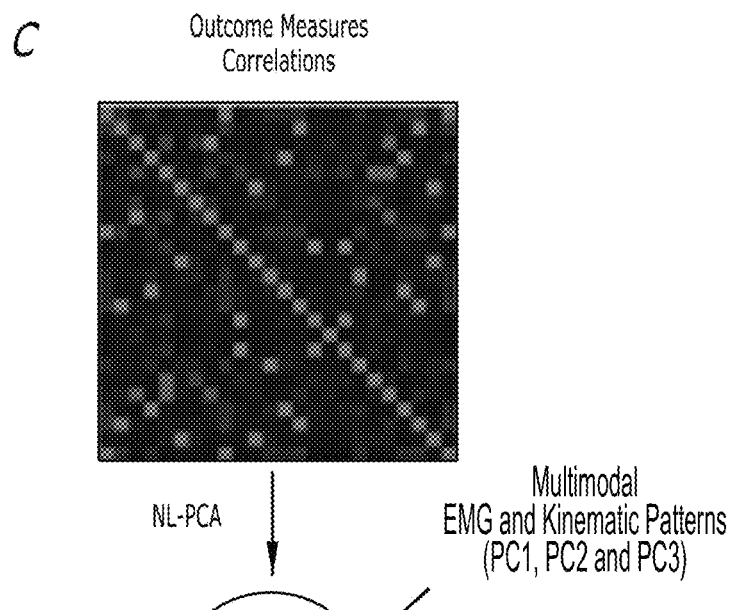
Figure 19C:
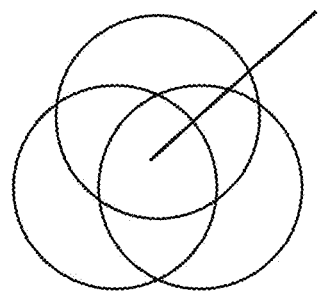
Figure 19D:
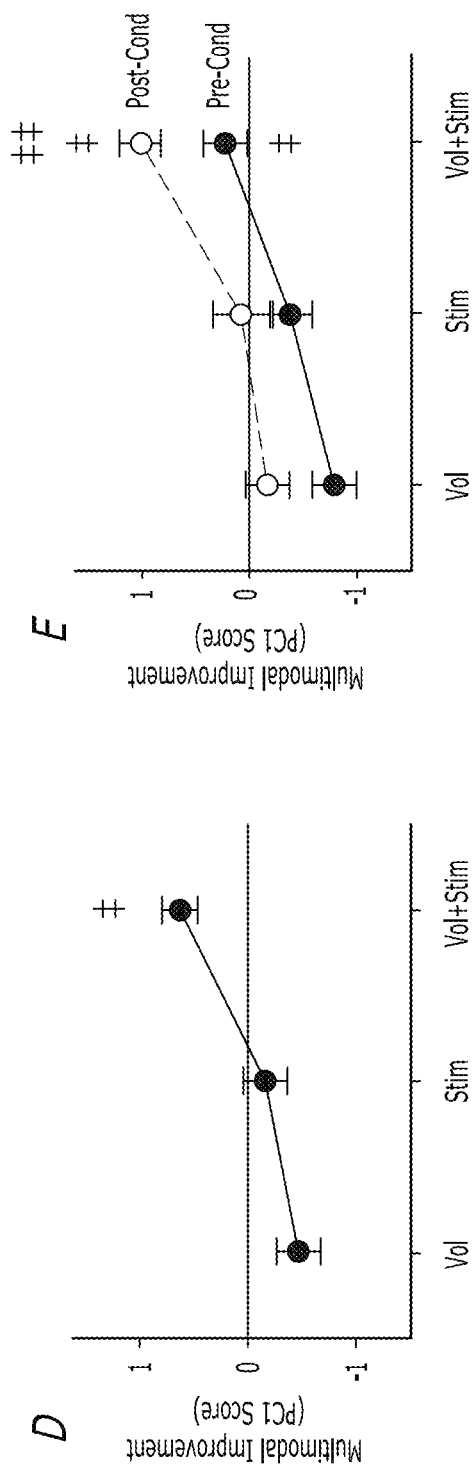

In some embodiments, the systems and methods described herein can after the completion of a three-minute conditioning period combined with T11 pcEmc increase the level of activation of the motor pools associated with the flexor and extensor muscles at the hip, knee, and ankle and the hip and knee displacement increased, e.g., significantly, with voluntary effort alone and with voluntary effort plus pcEmc beyond that observed prior to the procedure (FIGS. 19C-D). This effect was greater, e.g., significantly, with voluntary effort plus pcEmc than with voluntary effort alone (FIG. 19D). Further, levels, e.g., significant, of reciprocal modulation in concert with elevated EMG amplitudes were observed in the presence of stimulation (FIG. 19B).

The preceding disclosures are illustrative embodiments. It should be appreciated by those of skill in the art that the devices, techniques and methods disclosed herein elucidate representative embodiments that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention is claimed as follows:

1. A neuromodulation system comprising:
    a processor;
    a signal generator communicatively coupled to the processor; and
    a plurality of electrodes communicatively coupled to the signal generator, the plurality of electrodes comprising at least:
        a first electrode,
        a second electrode, and
        a third electrode,
    wherein the processor in cooperation with the signal generator, the first electrode, the second electrode, and the third electrode are configured to deliver a transcutaneous spinal cord stimulation to a user having a spinal cord injury, the transcutaneous spinal cord stimulation configured by the processor for inducing voluntary movement in the user,
    wherein the first electrode, the second electrode, and the third electrode are positioned transcutaneously on the user's neck, at least one electrode positioned below the spinal cord injury,
    wherein the first electrode is positioned over a cervical portion of the user's spinal cord, and
    wherein the second electrode and the third electrode are placed higher on the neck than the first electrode, and laterally offset on either side of the first electrode, on or over at least one of the spinal cord and/or the spinal cord dorsal roots, a muscle, or a nerve.

2. The neuromodulation system of claim 1, wherein the first electrode has a larger footprint than the second electrode and the third electrode.

3. The neuromodulation system of claim 1, wherein the induced voluntary movement is of an arm, a hand, a finger, or a combination thereof.

4. The neuromodulation system of claim 1, wherein the induced voluntary movement comprises at least one of reaching, grasping, pulling and pushing, swallowing and chewing, breathing, and coughing.

5. The neuromodulation system of claim 1, wherein the processor is further configured to model a relationship between the transcutaneous spinal cord stimulation applied to the user and quantifiable results generated by the induced voluntary movement.

6. The neuromodulation system of claim 5, wherein the second electrode is a sensor or a recording electrode and configured to record the quantifiable results generated by the induced voluntary movement.

7. The neuromodulation system of claim 6, wherein the sensor or the recording electrode is an electromyography ("EMG") sensor, a joint angle sensor, or a flex sensor.

8. The neuromodulation system of claim 5, wherein the model is a machine learning method.

9. The neuromodulation system of claim 5, wherein the processor is further configured to select a second transcutaneous spinal cord stimulation using the model for subsequent delivery to the user.

10. The neuromodulation system of claim 9, wherein the model causes the second transcutaneous spinal cord stimulation to be more optimized for inducing voluntary movement compared to the voluntary movement induced by the transcutaneous spinal cord stimulation.

11. The neuromodulation system of claim 9, wherein the transcutaneous spinal cord stimulation and the second transcutaneous spinal cord stimulation are specified by at least one of a waveform shape, an amplitude, a frequency, or a relative phasing.

12. The neuromodulation system of claim 11, wherein the transcutaneous spinal cord stimulation and the second transcutaneous spinal cord stimulation have a frequency between 5-40 Hz with an overlapping filling frequency between 5 kHz and 10 kHz.

13. The neuromodulation system of claim 11, wherein the transcutaneous spinal cord stimulation and the second transcutaneous spinal cord stimulation are delivered between 1-120 mA, 20-100 mA, or 85-100 mA.

14. The neuromodulation system of claim 1, wherein the transcutaneous spinal cord stimulation and the second transcutaneous spinal cord stimulation include a bipolar rectangular stimulus with a pulse duration between 0.5 milliseconds ("ms") to 3.0 ms that is filled with a carrier frequency between 5 kHz and 10 kHz.

15. The neuromodulation system of claim 1, wherein the transcutaneous spinal cord stimulation is delivered over multiple time periods such that:
    during a first time period, the transcutaneous spinal cord stimulation is applied to the user during physical conditioning of the user;
    during a second time period after the first time period, the transcutaneous spinal cord stimulation is applied to the user during reduced or no physical conditioning of the user; and
    during a third time period after the second time period, the transcutaneous spinal cord stimulation is applied to the user during the physical conditioning of the user,
    wherein the transcutaneous spinal cord stimulation applied during the first time period is used to establish a functional baseline of the user.

16. The neuromodulation system of claim 1, wherein the transcutaneous spinal cord stimulation is configured to be delivered after a neuropharmaceutical agent is administered to the user.

17. The neuromodulation system of claim 16, wherein the neuropharmaceutical agent includes at least one of a serotonergic drug, a dopaminergic drug, a noradrenergic drug, a monoaminergic drug, a GABAergic drug, or a glycinergic drug.

18. A neuromodulation system comprising:
    a processor;
    a signal generator communicatively coupled to the processor; and a plurality of electrodes communicatively coupled to the signal generator, the plurality of electrodes comprising at least:
a first electrode,
a second electrode, and
a third electrode,
wherein the processor in cooperation with the signal generator, the first electrode, the second electrode, and the third electrode are configured to deliver a transcutaneous spinal cord stimulation to a user having a spinal cord injury, the transcutaneous spinal cord stimulation configured by the processor for inducing voluntary movement in the user,
wherein the first electrode, the second electrode, and the third electrode are positioned transcutaneously on the user's neck, at least one electrode positioned below the spinal cord injury,
wherein the first electrode is positioned over a cervical portion of the user's spinal cord,
wherein the second electrode and the third electrode are offset with respect to the first electrode in the direction of the spinal cord, and laterally offset on either side of the first electrode, on or over at least one of the spinal cord and/or the spinal cord dorsal roots, a muscle, or a nerve, and
wherein the first electrode has a larger footprint than the second electrode and the third electrode.

19. The neuromodulation system of claim 18, wherein the processor is further configured to model a relationship between the transcutaneous spinal cord stimulation applied to the user and quantifiable results generated by the induced voluntary movement.

20. The neuromodulation system of claim 19, wherein the second electrode is a sensor or a recording electrode and configured to record the quantifiable results generated by the induced voluntary movement.

* * * * *